United States Patent
Traverse et al.

(10) Patent No.: US 11,505,522 B2
(45) Date of Patent: Nov. 22, 2022

(54) PROCESSES FOR THE PREPARATION OF (S)-TERT-BUTYL 4,5-DIAMINO-5-OXOPENTANOATE

(71) Applicant: Celgene Corporation, Summit, NJ (US)

(72) Inventors: John F. Traverse, Lebanon, NJ (US); Michael J. Zacuto, Jersey City, NJ (US); Weihong Zhang, Highland Park, NJ (US); Kirsten Faye Johnson, Morristown, NJ (US); Maryll E. Geherty, Pennington, NJ (US); Christopher Marton, Garwood, NJ (US)

(73) Assignee: CELGENE CORPORATION, Summit, NJ (US)

( * ) Notice: Subject to any disclaimer, the term of this patent is extended or adjusted under 35 U.S.C. 154(b) by 195 days.

(21) Appl. No.: 16/894,429

(22) Filed: Jun. 5, 2020

(65) Prior Publication Data
US 2020/0299228 A1    Sep. 24, 2020

Related U.S. Application Data

(62) Division of application No. 16/105,659, filed on Aug. 20, 2018, now Pat. No. 10,717,703.

(60) Provisional application No. 62/548,268, filed on Aug. 21, 2017.

(51) Int. Cl.
| | |
|---|---|
| C07C 231/18 | (2006.01) |
| C07C 231/12 | (2006.01) |
| C07C 237/06 | (2006.01) |
| C07D 209/46 | (2006.01) |
| C07C 275/70 | (2006.01) |
| C07C 237/12 | (2006.01) |
| C07C 273/18 | (2006.01) |
| C07C 275/24 | (2006.01) |
| C07C 67/313 | (2006.01) |
| C07C 231/02 | (2006.01) |

(52) U.S. Cl.
CPC .......... *C07C 231/18* (2013.01); *C07C 67/313* (2013.01); *C07C 231/02* (2013.01); *C07C 231/12* (2013.01); *C07C 237/06* (2013.01); *C07C 237/12* (2013.01); *C07C 273/1809* (2013.01); *C07C 275/24* (2013.01); *C07C 275/70* (2013.01); *C07D 209/46* (2013.01)

(58) Field of Classification Search
None
See application file for complete search history.

(56) References Cited

U.S. PATENT DOCUMENTS

| | | | |
|---|---|---|---|
| 3,989,812 A | 11/1976 | Barrett et al. | |
| 4,369,178 A | 1/1983 | Yamamura et al. | |
| 4,406,889 A | 9/1983 | Hartmann et al. | |
| 4,481,190 A | 11/1984 | Nestor et al. | |
| 4,610,983 A | 9/1986 | Takagawa et al. | |
| 4,690,916 A | 9/1987 | Nestor et al. | |
| 4,897,255 A | 1/1990 | Fritzberg et al. | |
| 4,988,496 A | 1/1991 | Fritzberg et al. | |
| 5,041,535 A | 8/1991 | Nyeki et al. | |
| 5,175,343 A | 12/1992 | Fritzberg et al. | |
| 5,210,072 A | 5/1993 | Dukor et al. | |
| 5,270,302 A | 12/1993 | Shiosaki et al. | |
| 5,556,982 A | 9/1996 | Fritzberg et al. | |
| 5,633,280 A | 5/1997 | Ayral-Kaloustian et al. | |
| 5,635,504 A | 6/1997 | Ryono et al. | |
| 5,710,129 A | 1/1998 | Lynch et al. | |
| 5,747,499 A | 5/1998 | Bavetsias et al. | |
| 6,043,278 A | 3/2000 | Schofield et al. | |
| 6,051,715 A | 4/2000 | Drauz et al. | |
| 6,117,896 A | 9/2000 | Kahn et al. | |
| 6,153,596 A | 11/2000 | Liotta et al. | |
| 6,410,576 B1 | 6/2002 | Nishimura et al. | |
| 7,169,919 B2 | 1/2007 | Albom et al. | |
| 7,173,107 B2 | 2/2007 | Blaszczak et al. | |
| 7,553,873 B2 | 6/2009 | Sum et al. | |
| 7,569,597 B2 | 8/2009 | Muller et al. | |
| 7,635,700 B2 | 12/2009 | Muller et al. | |
| 7,662,960 B2 | 2/2010 | Kahn et al. | |
| 8,168,756 B2 | 5/2012 | Valdez et al. | |
| 8,344,115 B2 | 1/2013 | Chang | |
| 8,518,972 B2 | 8/2013 | Man et al. | |
| 8,921,385 B2 | 12/2014 | Muller et al. | |
| 9,309,220 B2 | 4/2016 | Traverse et al. | |
| 2005/0187138 A1 | 8/2005 | Bartlett et al. | |
| 2005/0234065 A1 | 10/2005 | Hulin et al. | |

(Continued)

FOREIGN PATENT DOCUMENTS

| | | |
|---|---|---|
| CA | 1262400 A | 10/1989 |
| CN | 100522995 C | 8/2009 |

(Continued)

OTHER PUBLICATIONS

Filp et al. (Eur. J. Org. Chem., 2017, 5154, published Aug. 2, 2017). (Year: 2017).*
Adams et al., "An efficient route to the α-methyl ester of l-glutamic acid, and its conversion into cis-5-hydroxy-L-pipecolic acid," *Chem. Commun.*, 1996(3):349-350 (1996).
Adlercreutz et al., "Enzymic peptide synthesis in water-poor media," *Pept. 1990, 21st Proc. Eur. Pept. Symp.*, pp. 289-290 (1990).
Aebi et al., "Synthesis, conformation and immunosuppressive activity of a conformationally restricted cyclosporine lactam analogue," *J. Med. Chem.*, 31(9):1805-1815 (1988).

(Continued)

*Primary Examiner* — Sudhakar Katakam
*Assistant Examiner* — Jennifer C Sawyer
(74) *Attorney, Agent, or Firm* — Jones Day

(57) ABSTRACT

Provided are processes for the preparation of (S)-tert-butyl 4,5-diamino-5-oxopentanoate, or a salt, solvate, hydrate, enantiomer, mixture of enantiomers, or isotopologue thereof. Also provided are solid forms of various intermediates and products obtained from the processes.

20 Claims, 23 Drawing Sheets

(56) References Cited

U.S. PATENT DOCUMENTS

Figure 1:
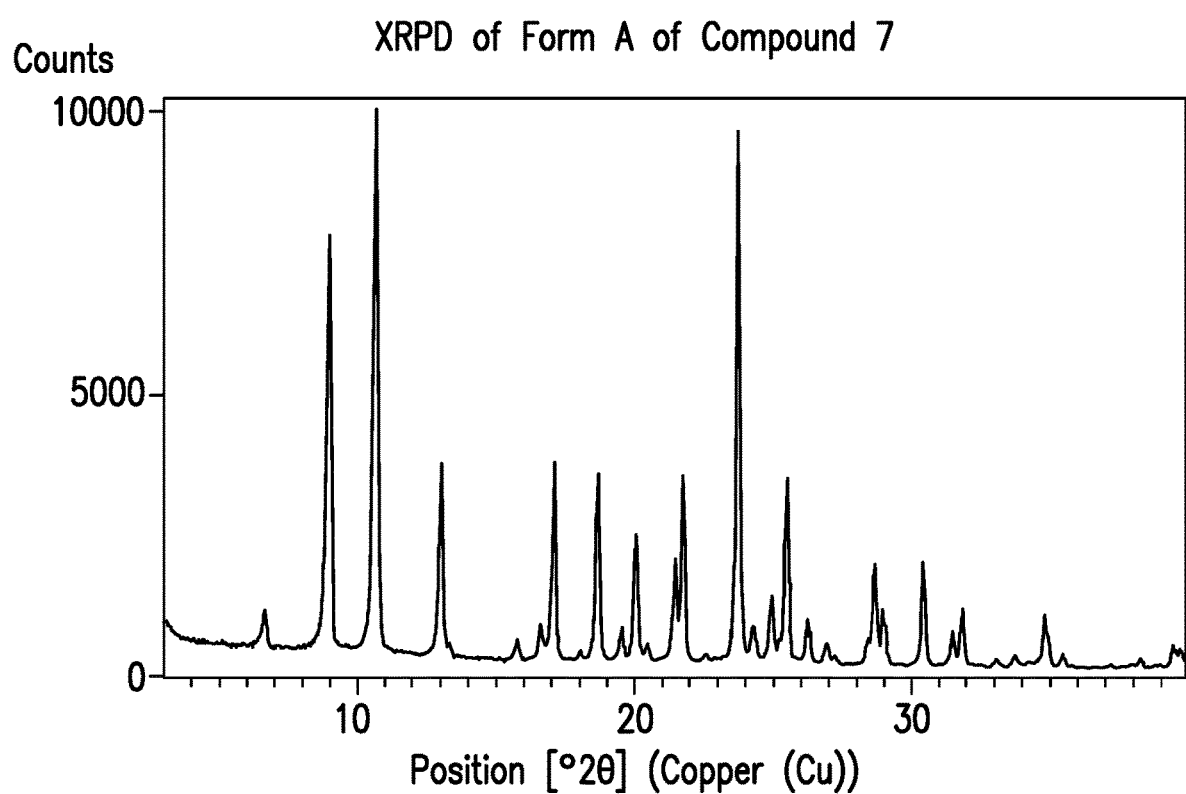

| | | | |
|---|---|---|---|
| 2005/0245432 | A1 | 11/2005 | Aurelio et al. |
| 2008/0275018 | A1 | 11/2008 | Endermann et al. |
| 2010/0280120 | A1 | 11/2010 | Datta |
| 2011/0196150 | A1 | 8/2011 | Man et al. |
| 2014/0046058 | A1 | 2/2014 | Traverse |
| 2015/0361066 | A1 | 12/2015 | Traverse |
| 2017/0283387 | A1 | 10/2017 | Manning et al. |

FOREIGN PATENT DOCUMENTS

| | | |
|---|---|---|
| CN | 1943341 B | 5/2012 |
| CN | 102731628 B | 5/2014 |
| CN | 104826544 B | 9/2016 |
| IN | 173794 B | 7/1994 |
| IN | 177680 B | 2/1997 |
| IN | 184769 B | 9/2000 |
| JP | 43-00213 B | 1/1968 |
| JP | 9-165370 A | 6/1997 |
| JP | 2000219663 A | 8/2000 |
| WO | WO 1995/018146 A1 | 7/1995 |
| WO | WO 1997/031016 A2 | 8/1997 |
| WO | WO 2001/079242 A2 | 10/2001 |
| WO | WO 2001/079268 A2 | 10/2001 |
| WO | WO 2008/156701 A2 | 12/2008 |
| WO | WO 2009/078040 A2 | 6/2009 |
| WO | WO 2010/065980 A1 | 6/2010 |
| WO | WO 2016/040527 A1 | 3/2016 |
| WO | WO 2016/065980 A1 | 5/2016 |

OTHER PUBLICATIONS

Ager et al., "The synthesis of the high-potency sweetener, NC-00637. Part 3: The glutamyl moiety and coupling reactions," *Org. Proc. Res. Dev.*, 8(1):72-85 (2004).

Alberg et al., "Structure-based design of a cyclophilin-calcineurin bridging ligand," *Science*, 262(5131):248-250 (1993).

Alexander et al., "Gamma-glutamyl hydrolase: kinetic characterization of isopeptide hydrolysis using fluorogenic sOostratss," *Biochemistry*, 47(4):1228-1239 (2008).

Allevi et al., "Facile and rapid regeneration of free amino acids from N-benzyloxycarbonyl-5-oxazolidinones and from N-benzyloxycarbonylamino derivatives by treatment with $BCl_3$ in dichloromethane," *Tetrahedron Letts.*, 45(30):5841-5843 (2004).

Al-Obeidi et al., "Synthesis of β- and γ-fluorenylmethyl esters of respectively $N^\alpha$-Boc-L-aspartic acid and $N^\alpha$-Boc-L-glutamic acid," *Int. J. Pept. Protein Res.*, 35(3):215-218 (1990).

Altman et al., "An improved synthesis of L-homohistidine," *Synthetic Comms.*, 19(11-12):2069-2076 (1989).

Amer, "Synthesis of new nicotinoyl amino acid derivatives" *Zagazig J. Pharm. Sci.*, 3(2):113-118 (1994) (Abstract only).

Antonjuk et al., "Synthesis of monoamides of methotrexate from L-glutamic acid monoamide tert-butyl esters," *J. Chem. Soc., Perkin Trans. I*, 9:1989-2003 (1984).

Armstrong et al., "A new method for the preparation of tertiary butyl ethers and esters," *Tetrahedron Letts.*, 29(20):2483-2486 (1988).

Aurelio et al., "A novel synthesis of N-methyl asparagine, arginine, histidine, and tryptophan," *Org. Lett.*, 4(21):3767-3769 (2002).

Aurelio et al., "An efficient synthesis of N-methyl amino acids by way of inteimediate 5-oxazolidinones," *J. Org. Chem.*, 68(7):2652-2667 (2003).

Aurelio et al., "The facile production of N-methyl amino acids via oxazolidonones," *Australian J. Chem.*, 53(5):425-433 (2000).

Bailey et al., "Chiral synthesis of 5-hydroxy-(L)-pipecolic acids from (L)-glutamic acid," *Tetrahedron*, 29(18):2231-2234 (1988).

Bandar et al., "Enantioselective bronsted base catalysis with chiral cyclopropenimines," *J. Am. Chem. Soc.*, 134:5552-5555 (2012).

Banner et al., "Stereoselective synthesis of the cis-275B decahydroquinoline ring system," *Tetrahedron Letts.*, 45(22):4411-4414 (2004).

Barnett et al., "Versatile synthesis of the signaling peptide glorin," *Beilstein J. Org. Chem.*, 13:247-250 (2017).

Barton et al., "Manipulation of the carboxyl groups of α-amino acids and peptides using radical chemistry based on esters of N-hydroxy-2-thiopyridone," *Tetrahedron*, 44(17):5479-5486 (1988).

Barton et al., "Reductive radical decarboxylation of amino acids and peptides," *J. Chem. Soc.*, 1984(19):1298-1299 (1984).

Barton et al., "The free radical chemistry of carboxylic esters of 2-selenopyridine-N-oxide; a convenient synthesis of (L)-vinylgylcine," *Tetrahedron*, 41(19):4347-4357 (1985).

Barton et al., "The invention of radical reactions. Part 39. The reaction of white phosphorus with carbon-centered radicals. An improved procedure for the synthesis of phosphonic acids and further mechanistic insights," *Tetrahedron*, 54(41):12475-12496 (1998).

Baumeister et al., "Rigid-rod β-barrels as lipocalin models: probing confined space by carotenoid encapsulation," *Chemistry*, 6(10):1739-1749 (2000).

Bavetsias et al., "Design and synthesis of cyclopenta[g]quinazoline-based antifolates as inhibitors of thymidylate synthase and potential antitumor agents," *J. Med. Chem.*, 43(10):1910-1926 (2000).

Bergmann et al., "A general process for the synthesis of peptides," *Berichte der Deutschen Chemischen Gesellschaft [Abteilung] B: Abhandlungen*, 65B:1192-1201 (1932). English abstact attached.

Bhosale et al., "Topologically matching supramolecular n/p-heterojunction architectures," *Angew. Chem. Int. Ed.*, 48(35):6461-6464 (2009).

Bloemhoff et al., "Polypeptides. XV. Syntesis of L- and D-homohistidine," *Recueil des Travaux Chimiques des Pays-Bas, J. Royal Netherlands Chem. Soc.*, 94(8):182-185 (1975).

Boekelheide et al., "Melanocytotoxicity and the mechanism of activation of γ-L-glutaminyl-4-hydroxybenzene," *J. Invest.*, 75(4):322-327 (1980).

Boekelheide et al., "The role of γ-glutamyl transpeptidase in the nephrotoxicity of an agaricus bisporus metabolite," *Am. J. Pathol.*, 100(3):651-662 (1980).

Bold et al., "Preparation of 'Semialdehyde' Derivatives of Aspartic and Glutamic Acid via the Rosenmund Reduction," *Helvetica*, 73(2):405-410 (1990), English abstact attached.

Bolos et al., "Asymmetric synthesis of pyrrolo[1,2-b][1,2]diazepine derivatives as potential antihypertensive drugs," *J. Org. Chem.*, 57(13):3535-3539 (1992).

Brown et al., "A single-bead decode strategy using electrospray ionization mass spectrometry and anewphotolabile linker: 3-amino-3-(2-nitrophenyl)propionic acid," *Mol. Div.*, 1(1):4-12 (1995).

Cai et al., "Convergent synthesis of novel muramyl dipeptide analogues: inhibition of porphyromonas gingivalis-induced pro-inflammatory effects by high doses of muramyl dipeptide," *J. Med. Chem.*, 59(14):6878-6890 (2016).

Chevallet et al., "Facile synthesis of tert-butyl ester of N-protected amino acids with tert-butyl bromide," *Tetrahedron Letts.*, 34(46):7409-7412 (1993).

Dekker et al., "Synthesis of peptides of methionine and their cleavage by proteolytic enzymes," *J. Biol. Chem.*, 180:155-173 (1949).

Ducrot et al., "Synthesis of tetrahydro-β-carbolines and studies of the Pictet-Spengler reaction," *Tetrahedron*, 56(17):2683-2692 (2000).

Duschmale et al., "Peptide catalysis in aqueous emulsions," *Chem. Commun.*, 50(6):8109-8112 (2014).

Esslinger et al., "Ngamma-aryl glutamine analogues as probes of the ASCT2 neutral amino acid transporter binding site," *Bioorg. Med. Chem.*, 13:1111-1118 (2005).

Etzkorn et al., "Cyclic hexapeptides and chimeric peptides as mimics of tendamistat," *J. Am. Chem. Soc.*, 116(23):10412-10425 (1994).

Forsch et al., "Synthesis of γ-[$^{15}$N]-L-glutamyl derivatives of 5,10-dideazatetrahydrofolate," *J. Labelled Compounds & Radiopharm.*, 42(11):1103-1117 (1999).

Fosker et al., "A dipeptide related to the active centers of certain enzymes," *Chemistry & Industry*, London, United Kingdom, pp. 569-570 (1964).

(56) References Cited

OTHER PUBLICATIONS

Fringuelli et al., "Synthesis and evaluation of anti-apoptotic activity of L-carnitine cyclic analogues and amino acid derivatives," *Il Farmaco*, 59(4):271-277 (2004).
Fruton et al., "Elongation of peptide chains in enzyme-catalyzed transamidation reactions," *J. Biol. Chem.*, 190:39-53 (1951).
Fruton, "Synthesis of l(+)-glutamine," *J. Biol. Chem.*, 165:333-337 (1946).
Fukuyama et al., "Total synthesis of (+)-porothramycin B," *Tetrahedron Letts.*, 34(16):2577-2580 (1993).
Gao et al., "Stereoselective synthesis of meso-2, 6-diaminopimelic acid and its selectively protected derivatives," *J. Org. Chem.*, 63(7):2133-2143 (1998).
Gibian et al., "Synthesis of peptides. I. Synthesis of glutamyl peptides with carbobenzyloxy-L-pyroglutamic acid," *Justus Liebigs Annalen der Chemie*, 640:145-156 (1961) (with English abstract).
Glass et al., "Enzymes as reagents in peptide synthesis: enzyme-labile protection for carboxyl groups," *Proc. Natl. Acad. Sci. USA*, 74(7):2739-2741 (1977).
Gregory et al., "Polypeptides. Part VII. Variations of the phenylalanyl position in the C-terminal tetrapeptide amide sequence of the gastrins," *J. Chem. Soc. C: Organic*, 1968:531-540 (1968).
Hammond et al., "β strand peptidomimetics as potent PDZ domain ligands," *Chem. Biol.*, 13(12):1247-1251 (2006).
Hanessian et al., "A novel and efficient synthesis of L-vinylglycine," *Tetrahedron Letts.*, 25(14):1425-1428 (1984).
Haq et al., "Synthesis and immunoadjuvant activity of MDP derivatives. Part I. Synthesis of N-substituted amides of MDP and their stimulatory effects on humoral immune response," *Indian J. Chem.*, 29B(3):263-267 (1990).
Harington et al., "Glutamic acid series," *J. Chem. Soc.*, 1940:706-712 (1940).
Hausch et al., "Design, synthesis, and evaluation of gluten peptide analogs as selective inhibitors of human tissue transglutaminase," *Chem. Biol.*, 10(3):225-231 (2003).
Henriksen et al., "Procedure for the semisyntheses of peptide amides having a glutamic or aspartic acid α-amide at the c-terminal," *Protein Peptide Letts.*, 5(3):141-146 (1998).
Hiebert et al., "Synthesis of a biologically active fluorescent muramyl didpeptide congener," *J. Med. Chem.*, 26(12):1729-1732 (1983).
Ho et al., "An asymmetric synthesis of cis-5-alkylproline derivatives," *J. Org. Chem.*, 51(13):2405-2408 (1986).
Ho et al., "Asymmetric synthesis of cis-5-alkylproline derivatives," *Pept.: Struct. Fund., Proc. Am. Pept. Symp.* 8th, Editor(s): Hruby, Victor J.; Rich, Daniel H. Publisher: Pierce Chem. Co., Rockford, IL, pp. 147-149 (1983).
Holcomb et al., "An asymmetric synthesis of differentially protected meso-2, 6-diaminopimelic acid," *Tetrahedron Letts.*, 35(38):7005-7008 (1994).
Holzapfel et al., "Antineoplastic agents. Par 108. Structural biochemistry. Part 23. Synthesis of the dolastatin thiazole amino acid component (gln)Thz," *J. Org. Chem.*, 50(13):2323-2327 (1985).
Hughes et al., "Effective methods for the synthesis of n-methyl β-amino acids from all twenty common α-amino acids using 1,3-oxazolidin-5-ones and 1,3-oxazinan-6-ones," *Helvetica*, 89(11):2611-2637 (2006).
Hughes et al., "Synthesis and structural characterization of N-methyl-DL-glutamic acid," *Australian J. Chem.*, 53(3):237-240 (2000).
Hughes et al., "Synthesis of new β-amino acids via 5-oxazolidinones and the arndt-eistert procedure," *Australian J. Chem.*, 58(II):778-784 (2005).
Itoh, "Peptides. I. Selective protection of α- or side-chain carboxyl groups of aspartic and glutamic acids. A facile synthesis of β-aspartyl and γ-glutamyl peptides," *Chem. Pharm. Bull.*, 17(8):1679-1686 (1969).
Iuchi et al., "Synthesis and effect on gastric secretion of several di- or tripeptides related to proglumide," *Chem. Pharm. Bull.*, 36(10):3961-3966 (1988).

Iuchi et al., "Synthesis of N-acyl-γ-D-glutamyl peptide derivatives containing a C-terminal small fragment of cholecystokinin and their effects on gastric secretion," *Chem. Pharm. Bull.*, 36(9):3433-3438 (1988).
Iyer et al., "Asymmetric catalysis of the strecker amino acid synthesis by a cyclic dipeptide," *J. Am. Chem. Soc.*, 118(20):4910-4911 (1996).
Izumi et al., "Catalytic asymmetric synthesis of anti-α,β-diamino acid derivatives," *Org. Lett.*, 18(4):696-699 (2016).
Jackson et al., "Synthesis of α-amino acids using amino acid γ-anion equivalents: synthesis of 5-oxo α-amino acids, homophenylalanine derivatives and pentenylglycines," *J. Chem. Soc. Perkin Trans.* 1, 1998(12):1903-1912 (1998).
Johannesson et al., "Angiotensin II analogs encompassing 5,9- and 5,10-fused thiazabicycloalkane tripeptide mimetics," *J. Med. Chem.*, 42(22):4524-4537 (1999).
Johnston et al., "Catalysis of transamidation reactions by proteolytic enzymes," *J. Biol. Chem.*, 185:629-641 (1950).
Jones et al., "Transamidation reactions catalyzed by cathepsin C," *J. Biol. Chem.*, 195:645-656 (1952).
Kapitannikov et al., "The c-terminal amidation of acyl amino acids and peptides by carboxypeptidase Y-catalykapzed," *Bioorganicheskaya Khimiya*, 14(6):797-801 (1988) (with English abstract).
Kasina et al., "Development and biologic evaluation of a kit for preformed chelate technetium-99m radiolabeling of an antibody Fab fragment using a diamide dimercaptide chelating agent," *J. Nucl. Med.*, 32(7):1445-1451 (1991).
Kawashima et al., "By-products in glutathione synthesis," *Report of Yamanouchi Central Res. Lab.*, 2:89-94 (1974) (with English abstract).
Keglevic et al., "Peptidoglycan-related disaccharide-dipeptides: differentiation between glutaminyl and isoglutaminyl residues by NMR spectroscopy," *J. Carbohydrate Chem.*, 11(2):119-136 (1992).
Keglevic et al., "Synthesis and reactions of O-acetylated benzyl α-glycosides of 6-O-(2-acetamido-2-deoxy-β-D-glucopyranosyl)-N-acetylmuramoyl-L- alanyl-D-isoglutamine esters: the base-catalysed isoglutamine in equilibrium glutamine rearrangement in peptidoglycan-related structures," *Carbohydrate Res.*, 186(1):63-75 (1989).
Kishore et al., "Ordered and oriented supramolecular n/p-heterojunction surface architectures: completion of the primary color collection," *J. Am. Chem. Soc.*, 131(31):11106-11116 (2009).
Klieger et al., "Peptide syntheses. X. Simplified preparation and reactions of carbobenzoxy-L-glutamic acid α-(half-esters)," *Justus Liebigs Annalen der Chemie*, 655:195-210 (1962) (with English abstract).
Klieger et al., "Peptides syntheses. IX. Preparation and reactions of carbobenzoxy-L-glutamic acid α-thioethyl ester," *Justus Liebigs Annalen der Chemie*, 651:194-205 (1962) (with English abstract).
Klieger et al., "Synthesis of peptides. II. Preparation and application of dicyclohexylammonium salts of acylated amino acids and peptides," *Justus Liebigs Annalen der Chemie*, 640:157-167 (1961) (with English abstract).
Kobayashi et al., "Synthesis and the adjuvant and tumor-suppressive activities of quinonyl muramyl dipeptides," *Bull. Chem. Soc. Jpn.*, 57(11):3182-3196 (1984).
Kokkala et al., "Optimization and structure-activity relationships of phosphinic pseudotripeptide inhibitors of aminopeptidases that generate antigenic peptides," *J. Med. Chem.*, 59:9107-9123 (2016).
Kokkala et al., "Optimization and structure-activity relationships of phosphinic pseudotripeptide inhibitors of aminopeptidases that generate antigenic peptides," supporting information, pp. S1-S9 (2016).
Kolasa et al., "1-Hydroxy-3-amino-2-piperidone (☐-N-hydroxycycloornithine) derivatives: key intermediates for the synthesis of hydroxamate-based siderophores," *J. Org. Chem.*, 55(6):1711-1721 (1990).
Kraml et al., "A synthesis of L-isoglutamine from γ-benzyl glutamate," *Can. J. Chem.*, 33:1630-1632 (1955).
Ksander et al., "Angiotensin converting enzyme inhibitors: N-substituted D-glutamic acid γ-dipeptides," *J. Med. Chem.*, 28(11):1606-1611 (1985).
Kubasch et al., "Synthesis of muramyl peptides containing meso-diaminopimelic acid," *Eur. J. Org. Chem.*, 2002(16):2710-2726 (2002).

(56) References Cited

OTHER PUBLICATIONS

Kusumoto et al., "Preparation of N-acetylmuramyl-L-[U-14C] alanyl-D-isoglutamine via a novel synthetic route," *Bull. Chem. Soc. Jpn.*, 52(4):1177-1181 (1979).

Kusumoto et al., "Synthesis of N-acetylmuramyl-L-[U-14C]alanyl-D-isoglutamine," *Tetrahedron Letts.*, 46:4055-4058 (1977).

Lalithamba et al., "Ultrasound mediated synthesis of 2-amino-1,3-selenazoles dervied from Fmoc/Boc/z-α-amio acids," ARKIVOC, (xi):77-90 (2010).

Lawandi et al., "Constrained peptidomimetics reveal detailed geometric requirements of covalent prolyl oligopeptidase inhibitors," *J. Med. Chem.*, 52(21):6672-6684 (2009).

Lawandi, "Development and application of chemical tools for the design and synthesis of bioactive molecules," *Dissertation Abstr. Int.*, Department of Chemistry, McGill University, Montreal, Canada, pp. 1-286 (2009).

Le Quesne et al., "Amino acids and peptides. I. An examination of the use of carbobenzyloxy-L-glutamic anhydride in the synthesis of glutamyl peptides," *J. Chem. Soc.*, 1950:1954-1959 (1950).

Lee et al., "Azacycle synthesis via radical cyclization of β-aminoacrylates," *Tetrahedron Letts.*, 36(3):417-420 (1995).

Lee et al., "Constituents of microbial iron chelators. The synthesis of optically active derivatives of δ-N-hydroxy-L-ornithine," *Tetrahedron Letts.*, 25(9):927-930 (1984).

Lee et al., "Regioselective amidation of aspartic and glutamic acid," *Synthesis*, 1991(11):935-936 (1991).

Lee et al., "Synthesis and anticonvulsant evaluation of A series of N-Cbz-α-aminoglutarimides," *Arch. Pharm. Res.*, 19(3):248-250 (1996).

Lee et al., "Synthesis of a δ-lactam analog of penemcarboxylate," *Bull. Kor. Chem. Soc.*, 11(5):361-362 (1990).

Lee et al., "The effect of N-substituted alkyl groups on anticonvulsant activities of N-Cbz-α-amino-N-alkylglutarimides," *Arch. Pharmacol Res.*, 22(5):491-495 (1999).

Lista et al., "Mini-zippers: Detenuination of oligomer effects for the assembly of photoactive supramolecular rod/stack architectures on gold nanoparticles and gold electrodes," *Supramolecular Chem.*, 21(3&4):238-244 (2009).

Loffet et al., "Tert-butyl esters of N-protected amino acids with tert-butyl fluorocarbonate (Boc-F)," *Tetrahedron Letts.*, 30(49):6859-6860 (1989).

Lohr et al., "Modified trityl ester protecting groups in peptide synthesis," *Synlett*, 1999(7):1136-1138 (1999).

Luesch et al., "Biosynthesis of 4-methylproline in cyanobacteria: cloning of nosE and nosF genes and biochemical characterization of the encoded dehydrogenase and reductase activities.," *J. Org. Chem.*, 68(1):83-91 (2003).

Malachowski et al., "The chemistry of phosphapeptides: investigations on the synthesis of phosphonamidate, phosphonate, and Phosphinate Analogs of Glutamyl-γ-glutamate," *J. Org. Chem.*, 59(25):7625-7634 (1994).

Martinez et al., "Synthesis of 3-amino-1,2,3,4-tetrahydro-pyridin-2-ones as peptidomimetics," Peptides 2000, Proceedings of the European Peptide Symposium, 26th, Montpellier, France, Sep. 10-15, 2000 (2001), Meeting Date 2000, pp. 813-814.

Matsukawa et al., "Choline derivatives. II. Glutamylcholine 1," *Yakugaku Zasshi*, 73:397-400 (1953), with English summary.

Matsukawa et al., "Choline derivatives. II. Glutamylcholine 2," *Yakugaku Zasshi*, 73:400-402 (1953), with English summary.

Micheel et al., "Peptidsynthesen nach dem oxazolidonverfahren, II—Peptide der L-Glutaminsäure," *Chemische Berichte*, pp. 309-312 (1959) (with English translation).

Miyamoto et al., "Informative secondary chiroptics in binary molecular organogel systems for donor-acceptor energy transfer," *Tetrahedron Letters*, 52:4030-4035 (2011).

Mou et al., "Synthesis of (S)-2-amino-8-oxodecanoic acid (Aoda) and apicidin A," *Tetrahedron Letts.*, 42(37):6603-6606 (2001).

Noyes et al., "Masthead," *J. Am. Chem. Soc.*, 82(7):1641-1644 (1960).

Nuijens et al., "Enzymatic c-terminal amidation of amino acids and peptides," *Tetrahedron Letts.*, 53(29):3777-3779 (2012).

Okada et al., "Synthesis of N-decanoyl-α- and γ-glutamyl oligopeptide methyl esters," *Yakugaku Zasshi*, 96(8):1038-1043 (1976) (with English abstract).

Okayama et al., "Lactam-cohformationally restricted analogs of $N^\alpha$-arylsulfonyl arginine amide : design, synthesis and inhibitory activity toward thrombin and related enzymes," *Chem. Pharm. Bull.*, 43(10):1683-1691 (1995).

Paris et al., "Synthesis of N- and side chain protected aspartyl and glutamyl aldehyde derivatives. Reinvestigation of the reduction of Weinreb amides," *Tetrahedron Letts.*, 39(11):1341-1344 (1998).

Park et al., "Synthesis and anticonvulsant evaluation of a series of (R)- and (S)-N-Cbz-α-aminoglutarimide and succinimide," *Bioorg. Med. Chem. Letts.*, 6(12):1297-1302 (1996).

Pehere et al., "An improved large scale procedure for the preparation of N-Cbz amino acids," *Tetrahedron Letters*, 52:1493-1494 (2011).

Pellicciari et al., "L-α-Aminoadipic acid from L-glutamic acid," *Synthetic Communications*, 18(14):1707-1713 (1988).

Potterat et al., "Metabolic products of microorganisms. Part 269. 5-phenylpentadienoic-acid derivatives from *streptomyces* sp.," *Helvetica Chimica Acta*, 77(2):569-574 (1994).

Regnier et al., "New developments for the design, synthesis and biological evaluation of potent SARS-CoV $3CL^{Pro}$ inhibitors," *Bioorg. Med. Chem. Letts.*, 19(10):2722-2727 (2009).

Ressler et al., "The isoglutamine isomer of oxytocin: its synthesis and comparison with oxytocin," *J. Am. Chem. Soc.*, 79:4511-4515 (1957).

Ressler, "Convenient syntheses of L-isoglutamine and L-isoasparagine through derivatives commonly useful for peptide synthesis," *J. Am. Chem. Soc.*, 82(7):1641-1644 (1960).

Ribic et al., "Synthesis and immunostimulating properties of novel adamant-1-yl tripeptides," *Chemistry & Biodiversity*, 9(4):777-788 (2012).

Rolski et al., "New method of synthesis of glutamimide," *Roczniki Chemii*, 40(4):689-694 (1966), with English summary.

Sagara et al., "A mechano- and thermoresponsive luminescent cyclophane," *Chem. Commun.*, 52(33):13147-13150 (2016).

Sakai et al., "Zipper assembly of photoactive rigid-rod naphthalenediimide π-stack architectures on gold nanoparticles and gold electrodes," *J. Am. Chem. Soc.*, 129(51):15758-15759 (2007).

Samsel et al., "Synthesis and antiproliferative activity of conjugates of adenosine with muramyl dipeptide and nor-muramyl dipeptide derivatives," *Bioorg. Med. Chem. Letts.*, 24(15):3587-3591 (2014).

Sawayama et al., "Angiotensin-converting enzyme inhibitors: synthesis and structure-activity relationships of potent N-benzyloxycarbonyl tripeptide inhibitors," *Chem. Pharm. Bull.*, 37(9):2417-2422 (1989).

Schafer et al., "The synthesis and some biological properties of N-(6-purinyl) peptides," *Bio. Chem. Hoppe-Seyler*, 367(8):757-768 (1986).

Scholtz et al., "A convenient differential protection strategy for functional group manipulation of aspartic and glutamic acids," *Synthesis*, 1989(7):542-544 (1989).

Scholtz et al., "Synthesis and evaluation of inhibitors for *Escherichia coli* carbamyl phosphate synthetase," *Bioorg. Chem.*, 17(4):422-433 (1989).

Seebach et al., "Electrochemical decarboxylation of L-threonine and oligopeptide derivatives with foimation of N-Acyl-N, O-acetals: Preparation of oligopeptides with amide or phophonate C-terminus," *Helvetica*, 72(3):401-425 (1989).

Seide et al., "Improved synthesis of 7,5-fused bicyclic lactams for use as peptidomimetics," *Synthetic Commun.*, 35(7):995-1002 (2005).

Shealy et al., "Synthesis of D- and L-thalidomide and related studies," *J. Pharm. Sci.*, 57(5):757-764 (1968).

Shirude et al., "(2S,5R/2R,5S)-aminoethylpipecolyl aepip-aegPNA chimera: synthesis and duplex/triplex stability," *Tetrahedron*, 60(42):9485-9491 (2004).

Siedler et al., "Synthesis of neo-glycosylated L-alanyl-D-isoglutamine derivatives as potential immunoadjuvants," *Peptide Res.*, 5(1):39-47 (1992).

(56) References Cited

OTHER PUBLICATIONS

Silva et al., "Synthesis of N-[(3S)-2,6-Dioxo-1-(2-phenylethyl)-3-piperidinyl]-(2S)-2-methylbutanamide ((-)-Julocrotine),"*J. Nat. Prod.*, 74(6):1531-1534 (2011).

Siriwardena et al., "Synthesis and proinflammatory effects of peptidoglycan-derived neoglycopeptide polymers," *J. Am. Chem. Soc.*, 123(33):8145-8146 (2001).

Stanton et al., "A mild protocol for the conversion of simple esters to tert-butyl esters," *J. Org. Chem.*, 62(23):8240-8242 (1997).

Stofla et al., "Design, synthesis, and biological evaluation of 2-aminobenzanilide derivatives as potent and selective HDAC inhibitors," *Chem. Med. Chem.*, 7(7):1256-1266 (2012).

Straka et al., "Synthesis of isoglutamine, isoasparagine, and derivatives," *Collect. Czech. Chem. Commun.*, 42(2):560-563 (1977).

Sydnes et al., "Synthesis of glutamic acid and glutamine peptides possessing a trifluoromethyl ketone group as SARS-CoV 3CL protease inhibitors," *Tetrahedron Letts.*, 62(36):8601-8609 (2006).

Thompson et al., "Homochiral synthesis of an aza analog of S-adenosyl-L-methionine (AdoMet) and its binding to the *E. coli* methionine repressor protein (MetJ)," *Chem. Commun.*, 1996(6):791-792 (1996).

Thompson et al., Synthesis of an aza analog of S-adenosyl-L-methionine and its binding to the *E. coli* methionine repressor protein (MetJ), *Collection of Czechoslovak Chemical Communications*, 61:885-S87 (1996).

Thompson et al., "Synthesis of two stable nitrogen analogues of s-adenosyl-L-methionine,"*J. Org. Chem.*, 64(20)7467-7473 (1999).

Vakalopoulou et al., "Synthesis of substance P c-terminal analogs incorporating D-amino acids and studies of their antineoplastic properties in vitro," *Drug Discovery and Design: Medical Aspects*, 55:20-24 (2002).

Van Nguyen et al., "A novel synthesis of N-but-3-enyl-α- and β-amino acids," *Synthesis*, 12:1991-1998 (2009).

Wallen et al., "Confoimationally rigid N-acyl-5-alkyl-1-prolyl-pyrrolidines as prolyl oligopeptidase inhibitors," *Bioorg. Med. Chem.*, 11(17):3611-3619 (2003).

Walter et al., "Reaction of (trifluoromethyl)trimethylsilane with oxazolidin-5-ones: synthesis of peptidic and nonpeptidic trifluoromethyl ketones," *J. Org. Chem.*, 63(15):5179-5192 (1998).

Wang et al., "Synthesis of fluoro-containing muramyl dipeptide analogs," *Tetrahedron*, 54(41):12597-12608 (1998).

Wang et al., "Synthesis of muramyl dipeptide analogs by incorporation of 3, 3, 3-trifluoroalanine," *Chin. Chem. Letts.*, 11(4):297-300 (2000).

Wang et al., "Synthesis of ω-tert-butyl esters of aspartic acid and glutamic acid via b, b-difluoroboroxazolidones," *Chem. Pharm. Bull.*, 44(11):2189-2191 (1996).

Widmer et al., "Carboxypeptidase Y as a catalyst for peptide synthesis in aqueous phase with minimal protection," *Pept., 16th Proc. Eur. Pept. Symp.*, Copenhagen, Denamrk, pp. 46-55 (1981).

Widmer et al., "Influence of the structure of amine components on carboxypeptidase Y catalyzed amide bond foimation," *Carlsberg Res. Commun.*, 46(1-2):97-106 (1981).

Wieland et al., "N- (α-aminoacyl)sulfonamides,"*Chemische Berichte*, 93:1236-1246 (1960) (with English abstract).

Wieland et al., "Peptide syntheses. X. α- and γ-phenyl thioesters of N-acylglutamic acids,"*Justus Liebigs Annalen der Chemie*, 597:111-122 (1955) (with English abstract).

Williams et al., "Asymmetric synthesis of γ-D- and -L-glutamyl-L-meso-diaminopimelic acid dipeptide," *J. Org. Chem.*, 59:6190-6193 (1994).

Williamson et al., "Novel adenosine-derived inhibitors of 70 kDa heat shock protein, discovered through structure-based design," *J. Med. Chem.*, 52:1510-1513 (2009).

Xu et al., "Asymmetric synthesis of highly functionalized tetrahydropyran DPP-4 inhibitor," *Org. Lett.*, 16(20):5422-5425 (2014).

Yang et al., "A novel immunostimulator, N2-[α-O-Benzyl-N-(acetylmuramyl)-L-alanyl-D-isoglutaminyl]-N6-trans-(m-nitrocinnamoyl)-L-lysine, and its adjuvancy on the hepatitis B surface antigen," *J. Med. Chem.*, 48(16):5112-5122 (2005).

Zabriskie et al., "Mechanism-based inactivation of peptidylglycine α-hydroxylating monooxygenase (PHM) by a substrate analog, D-phenylalanyl-L-phenylalanyl-D-vinylglycine: inhibition of formation of peptide C-terminal amides,"*J. Am. Chem. Soc.*, 114(6):2270-2272 (1992).

Zhang et al., ""Meshed-bag gathered-bunch" method for solid-phase synthesis of small molecular diverse compounds," *J. Comb. Chem.*, 4(2):131-137 (2002).

Zhang et al., "An inexpensive fluorescent labeling protocol for bioactive natural products utilizing Cu(I)-catalyzed huisgen reaction," *Tetrahedron*, 63(29):6813-6821 (2007).

* cited by examiner

PROCESSES FOR THE PREPARATION OF (S)-TERT-BUTYL 4,5-DIAMINO-5-OXOPENTANOATE

This application is a divisional application of U.S. application Ser. No. 16/105,659, filed Aug. 20, 2018, which claims priority to U.S. Provisional Application No. 62/548,268, filed Aug. 21, 2017, the entireties of which are incorporated herein by reference.

1. FIELD

Provided herein are processes for the preparation of (S)-tert-butyl 4,5-diamino-5-oxopentanoate, or a salt, solvate, hydrate, enantiomer, mixture of enantiomers, or isotopologue thereof. The compound can be used in making pharmaceutically active compounds that contain an (S)-2-aminoglutarimide moiety, for example, (S)-3-(4-((4-(morpholinomethyl)benzyl)oxy)-1-oxoisoindolin-2-yl)piperidine-2,6-dione.

2. BACKGROUND

Certain compounds containing a glutarimide moiety have been reported to show pharmaceutical properties suitable for clinical development. One example is (S)-3-(4-((4-(morpholinomethyl)benzyl)oxy)-1-oxoisoindolin-2-yl)piperidine-2,6-dione. The compound is described in U.S. Patent Publication No. 2011/0196150, which is incorporated herein by reference in its entirety.

Processes for synthesizing enantiomerically enriched or enantiomerically pure 3-(4-((4-(morpholinomethyl)benzyl)oxy)-1-oxoisoindolin-2-yl)piperidine-2,6-dione have been previously described in U.S. Patent Publication No. 2014/0046058, which is incorporated herein by reference in its entirety. The processes utilize (S)-tert-butyl 4,5-diamino-5-oxopentanoate hydrochloride as a key starting material for the construction of the (S)-2-aminoglutarimide moiety.

The synthesis of (S)-tert-butyl 4,5-diamino-5-oxopentanoate hydrochloride has been previous reported. For example, one recent report describes synthesis of (S)-tert-butyl 4,5-diamino-5-oxopentanoate hydrochloride from Cbz-(L)-Glu(tBu)-OH. *J. Med. Chem.* 2016, 59(19), 9107-9123 (supporting information).

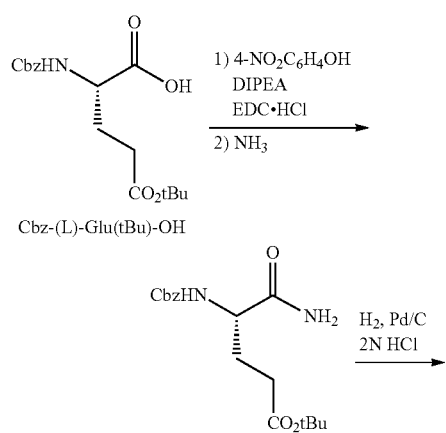

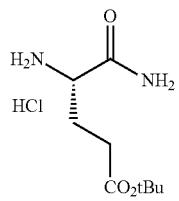

This reported method, however, is not suitable for scale up. It describes removing solvent to dryness, which leads to an uncontrolled precipitation (which in turn can lead to variable purity). It also describes the use of high volumes (up to 56 volumes, i.e., 56 mL per gram), which is inefficient on large scales. Additionally, the process does not describe control of the stereogenic (chiral) center. There is no literature about the chiral purity of the products.

(S)-tert-Butyl 4,5-diamino-5-oxopentanoate hydrochloride is commercially available, normally only at gram quantities. The price normally ranges from $300 to $800 per 100 g of the product, which could be costly for large scale preparation of glutarimide-containing compounds. The delivery normally takes several weeks (e.g., about 12 weeks), and the chemical purity of the commercial product is normally reported to be about 95-98%. The analytical data for the chiral purity is often not well defined.

Despite of its current availability, a need still exists for the development of alternative synthetic processes for (S)-tert-butyl 4,5-diamino-5-oxopentanoate hydrochloride.

3. SUMMARY

Provided herein are processes for the preparation of a compound of Formula (I):

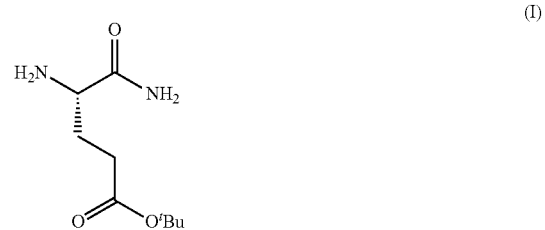 [SMILES: CC(C)(C)OC(=O)CC[C@H](N)C(N)=O]

or a salt, solvate, hydrate, enantiomer, mixture of enantiomers, or isotopologue thereof. A compound of Formula (I) has a chemical name of (S)-tert-butyl 4,5-diamino-5-oxopentanoate. The processes comprise an optional step of preparing a salt of the compound.

In one embodiment, provided herein are processes for the preparation of a compound of Formula (I), or a solvate, hydrate, enantiomer, mixture of enantiomers, or isotopologue thereof, comprising a ring-opening reaction of a N-protected oxazolidin-5-one moiety with ammonia or a protected amine.

In one embodiment, provided herein are processes for the preparation of a compound of Formula (I), or a solvate, hydrate, enantiomer, mixture of enantiomers, or isotopologue thereof, comprising a ring-opening reaction of an oxazolidine-2,5-dione moiety with ammonia.

In one embodiment, provided herein are processes for the preparation of a compound of Formula (I), or a solvate, hydrate, enantiomer, mixture of enantiomers, or isotopologue thereof, comprising a ring-opening reaction of a N-protected pyrrolidin-2-one moiety with a tert-butoxide nucleophile.

In one embodiment, provided herein are processes for the preparation of a compound of Formula (I), or a solvate, hydrate, enantiomer, mixture of enantiomers, or isotopologue thereof, comprising a Michael addition reaction of 2-((diphenylmethylene)amino)acetonitrile, 2-((diphenylmethylene)amino)acetamide, or 2-((diphenylmethylene)amino)acetate ester to tert-butyl acrylate.

In one embodiment, provided herein are processes for the preparation of a compound of Formula (I), or a solvate, hydrate, enantiomer, mixture of enantiomers, or isotopologue thereof, comprising a Michael addition reaction of 2-phenyloxazol-5(4H)-one to tert-butyl acrylate.

Also provided herein are processes for the preparation of a compound of Formula (XIV):

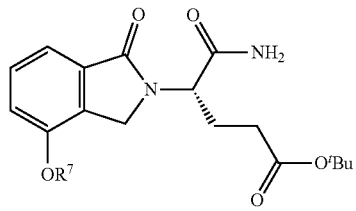

(XIV)

or a salt, solvate, hydrate, enantiomer, mixture of enantiomers, or isotopologue thereof. The processes utilize a compound of Formula (I) as one of the starting material.

Also provided herein are processes for the preparation of a compound of Formula (XV):

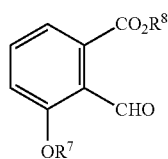

(XV)

or a salt, solvate, hydrate, enantiomer, mixture of enantiomers, or isotopologue thereof. The compound of Formula (XV) can be used as another starting material for the preparation of a compound of Formula (XIV).

In one embodiment, provided herein are intermediate compounds used in or product compounds prepared by the processes provided herein, including solid forms (e.g., crystalline forms) thereof.

In one embodiment, provided herein are solid forms (e.g., Form A) comprising Compound 7 of the formula:

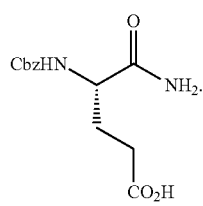

7

In one embodiment, provided herein are solid forms (e.g., Form A) comprising racemic Compound 7 of the formula:

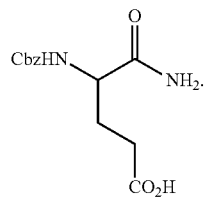

rac-7

In one embodiment, provided herein are solid forms (e.g., Form A) comprising Compound 8 of the formula:

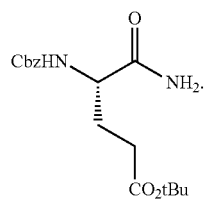

8

In one embodiment, provided herein are solid forms (e.g., Form A) comprising racemic Compound 8 of the formula:

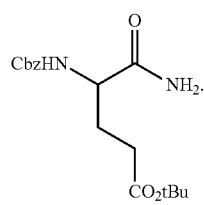

rac-8

In one embodiment, provided herein are solid forms (e.g., Form A and Form B) comprising Compound 1 of the formula:

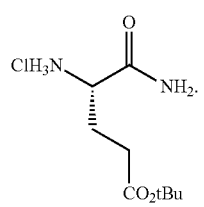

1

In one embodiment, provided herein are solid forms (e.g., Form A) comprising racemic Compound 1 of the formula:

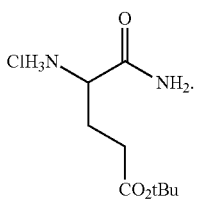

rac-1

In one embodiment, provided herein are solid forms (e.g., Form A) comprising Compound 35 of the formula:

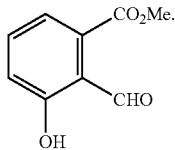

In one embodiment, provided herein are solid forms (e.g., Form 1) comprising Compound 37 of the formula:

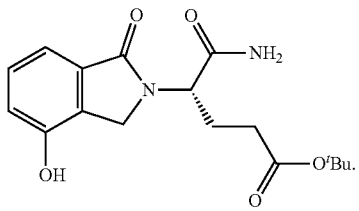

In one embodiment, provided herein are solid forms (e.g., Form 1) comprising racemic Compound 37 of the formula:

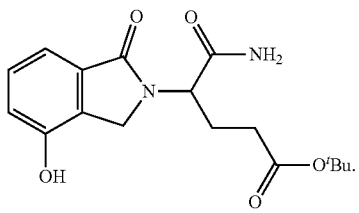

5. BRIEF DESCRIPTION OF THE FIGURES

FIG. 1 provides a representative X-ray powder diffraction (XRPD) pattern of Form A of Compound 7.

Figure 2:
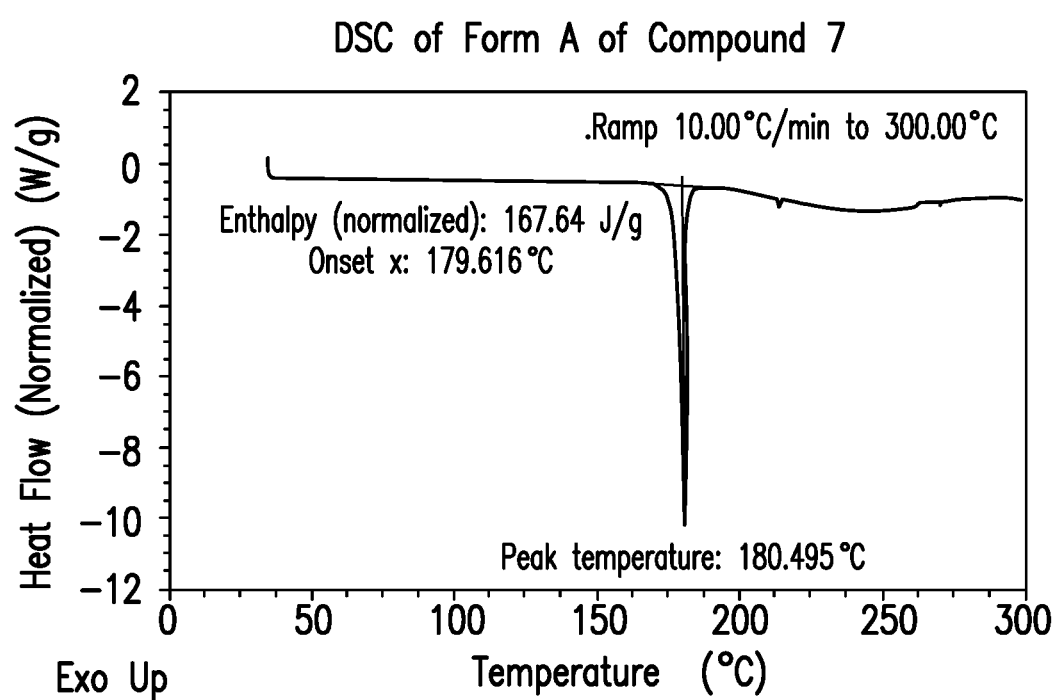

FIG. 2 provides a representative differential scanning calorimetric (DSC) thermogram of Form A of Compound 7.

Figure 3:
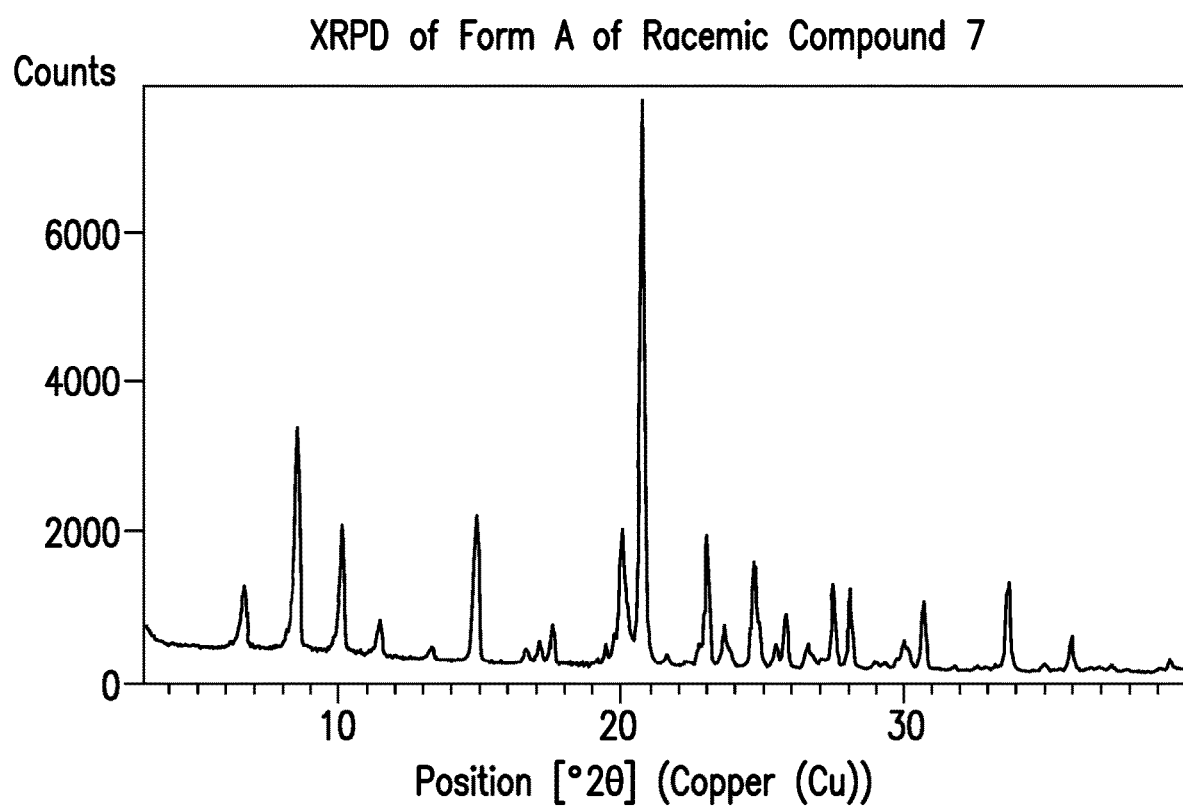

FIG. 3 provides a representative XRPD pattern of Form A of racemic Compound 7.

Figure 4:
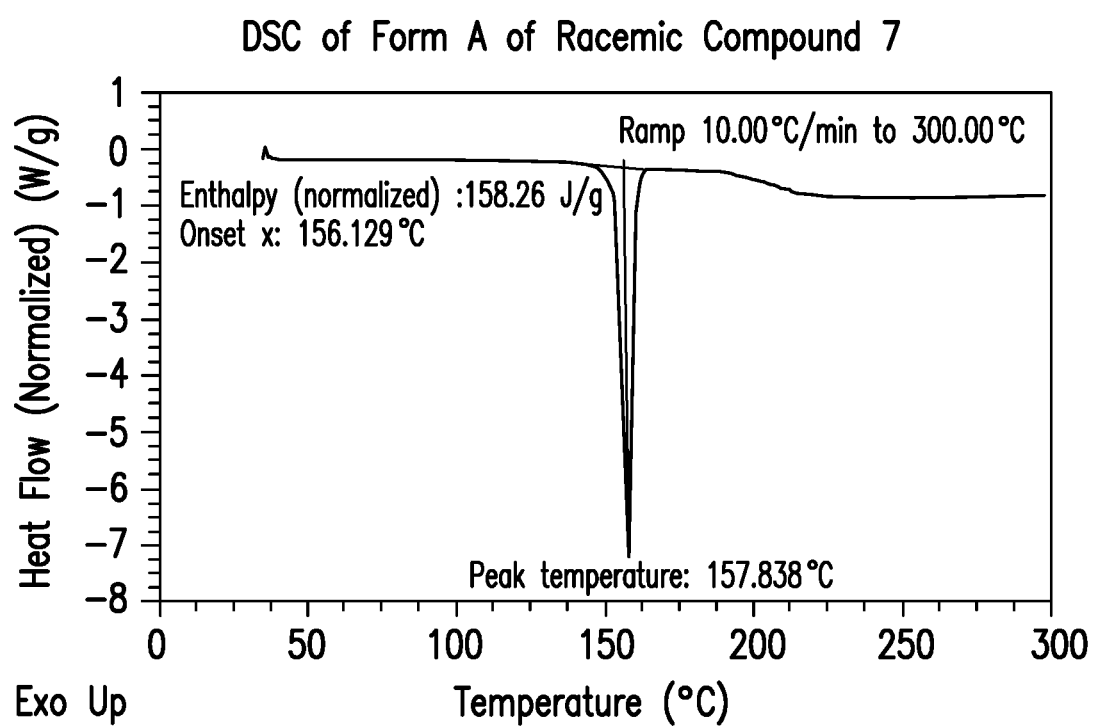

FIG. 4 provides a representative DSC thermogram of Form A of racemic Compound 7.

Figure 5:
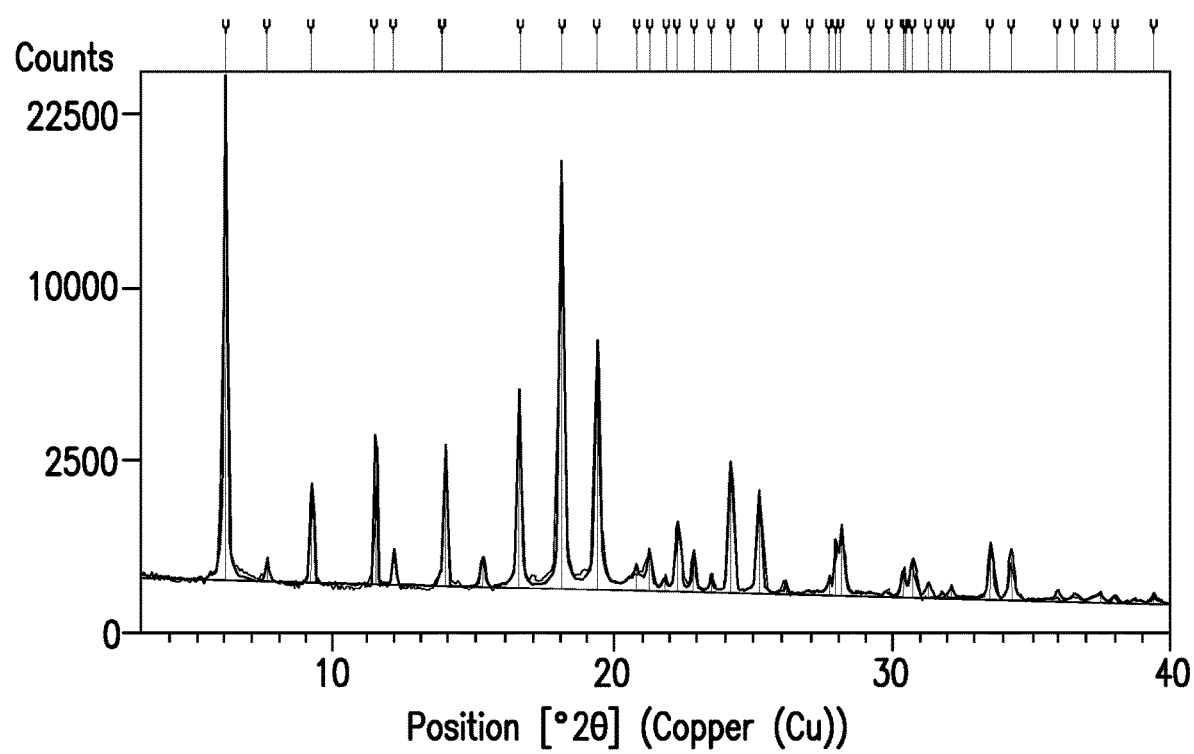

FIG. 5 provides a representative XRPD pattern of Form A of Compound 8.

Figure 6:
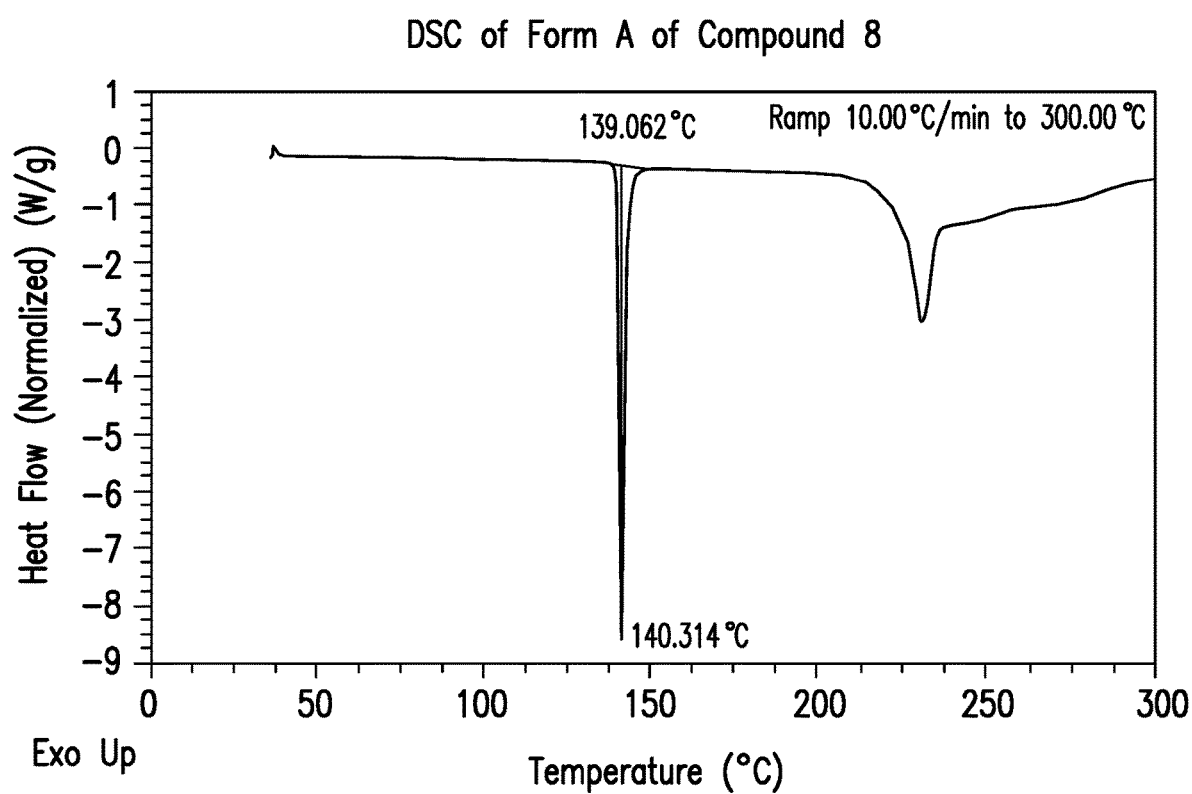

FIG. 6 provides a representative DSC thermogram of Form A of Compound 8.

Figure 7:
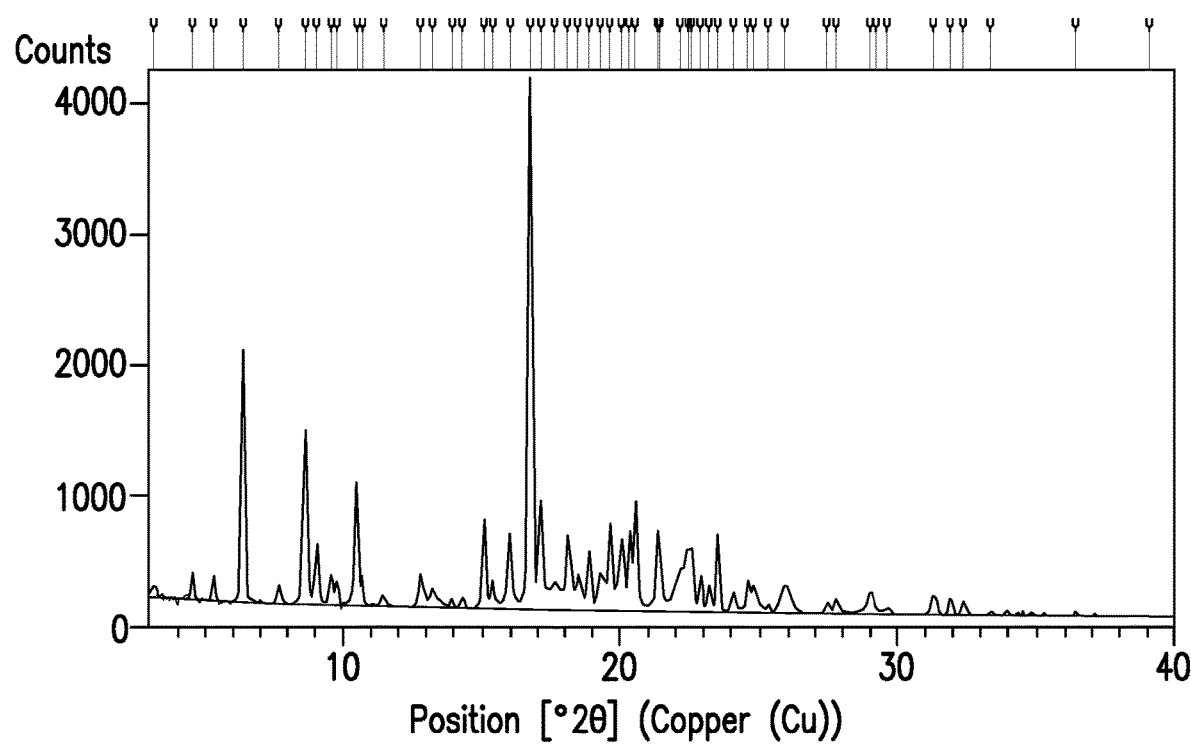

FIG. 7 provides a representative XRPD pattern of Form A of racemic Compound 8.

Figure 8:
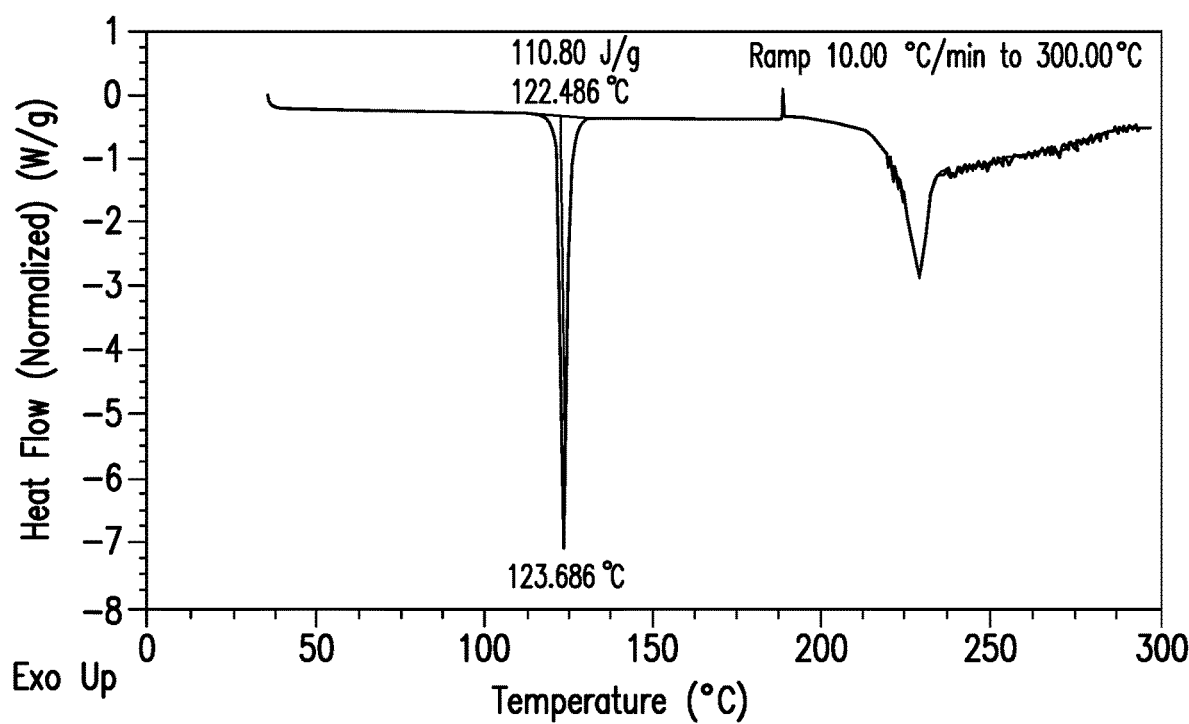

FIG. 8 provides a representative DSC thermogram of Form A of racemic Compound 8.

Figure 9:
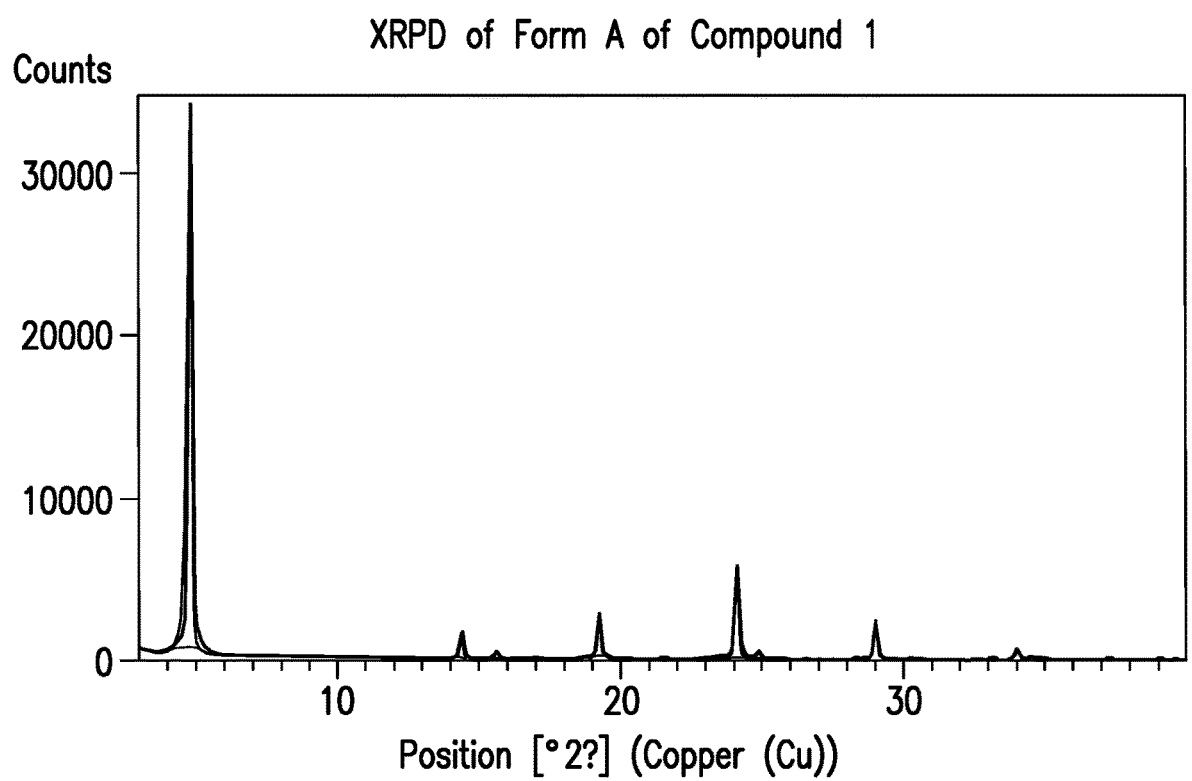

FIG. 9 provides a representative XRPD pattern of Form A of Compound 1.

Figure 10:
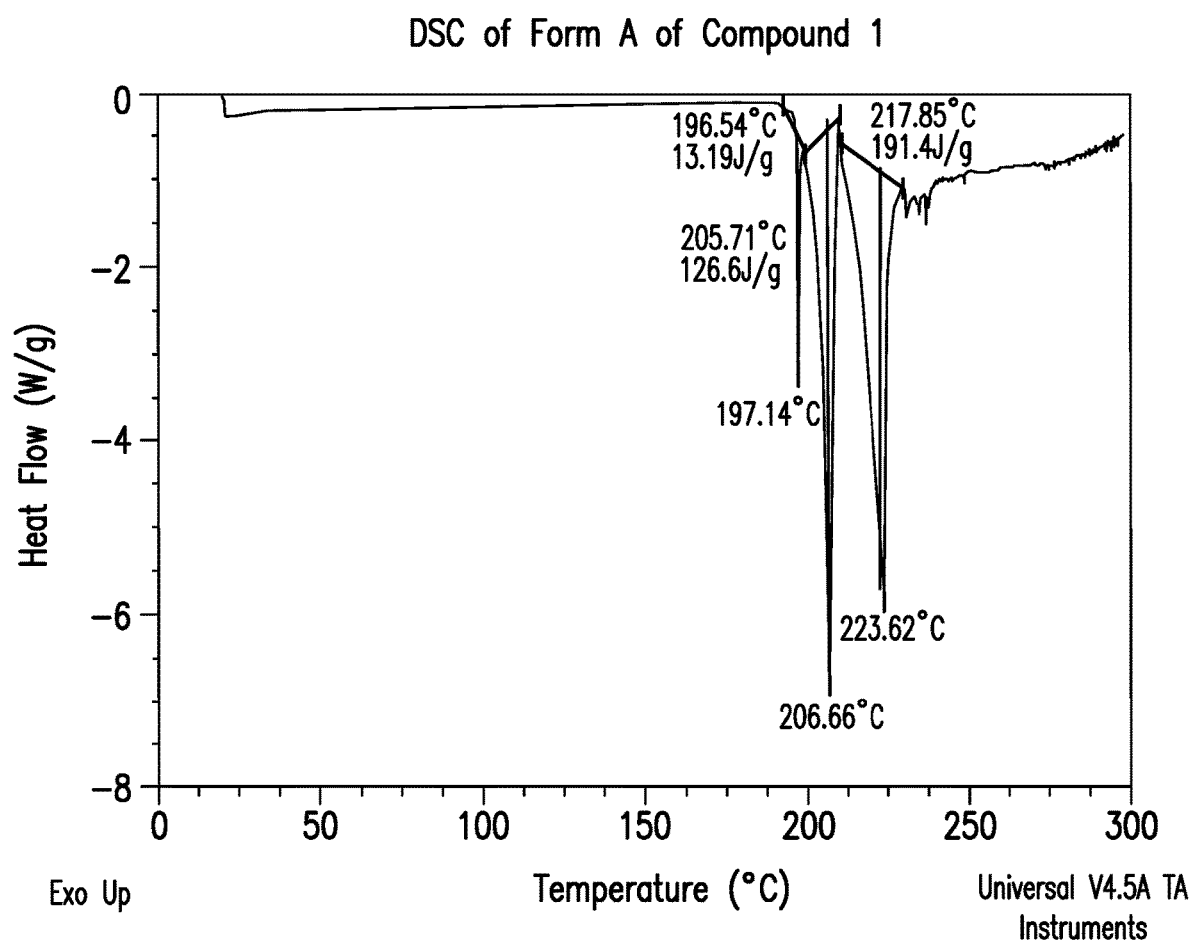

FIG. 10 provides a representative DSC thermogram of Form A of Compound 1.

Figure 11:
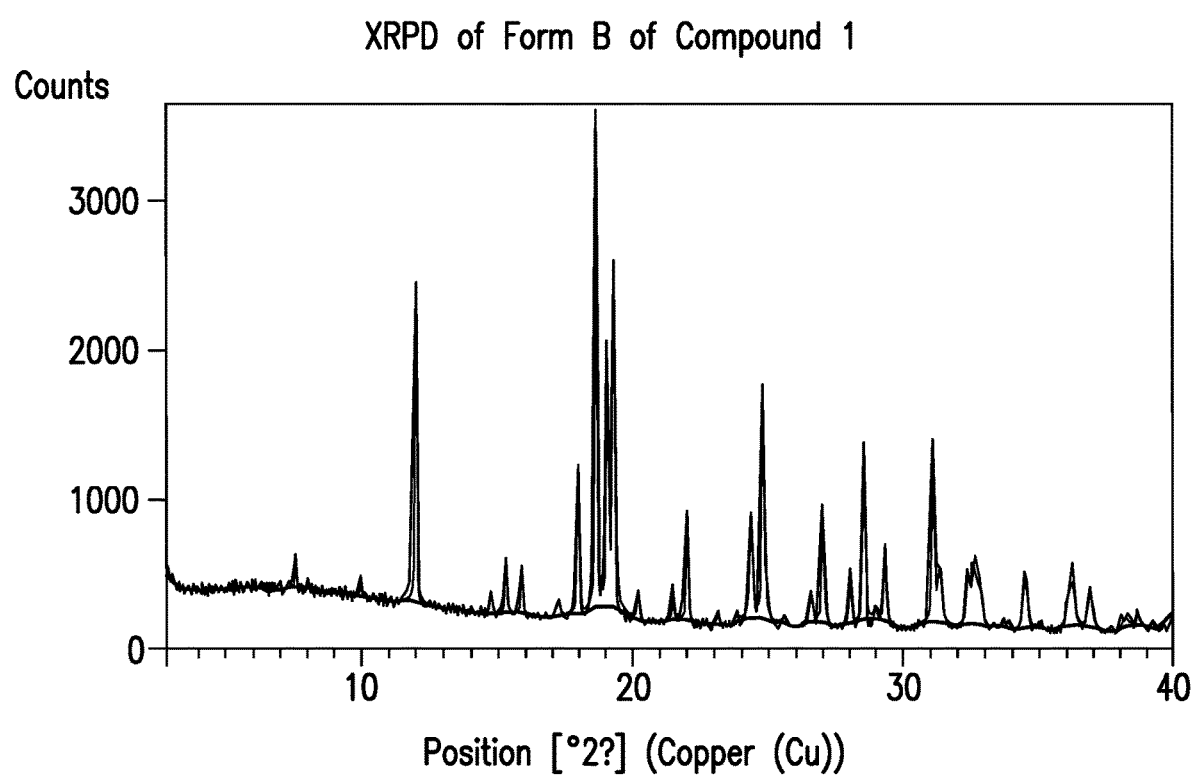

FIG. 11 provides a representative XRPD pattern of Form B of Compound 1.

Figure 12:
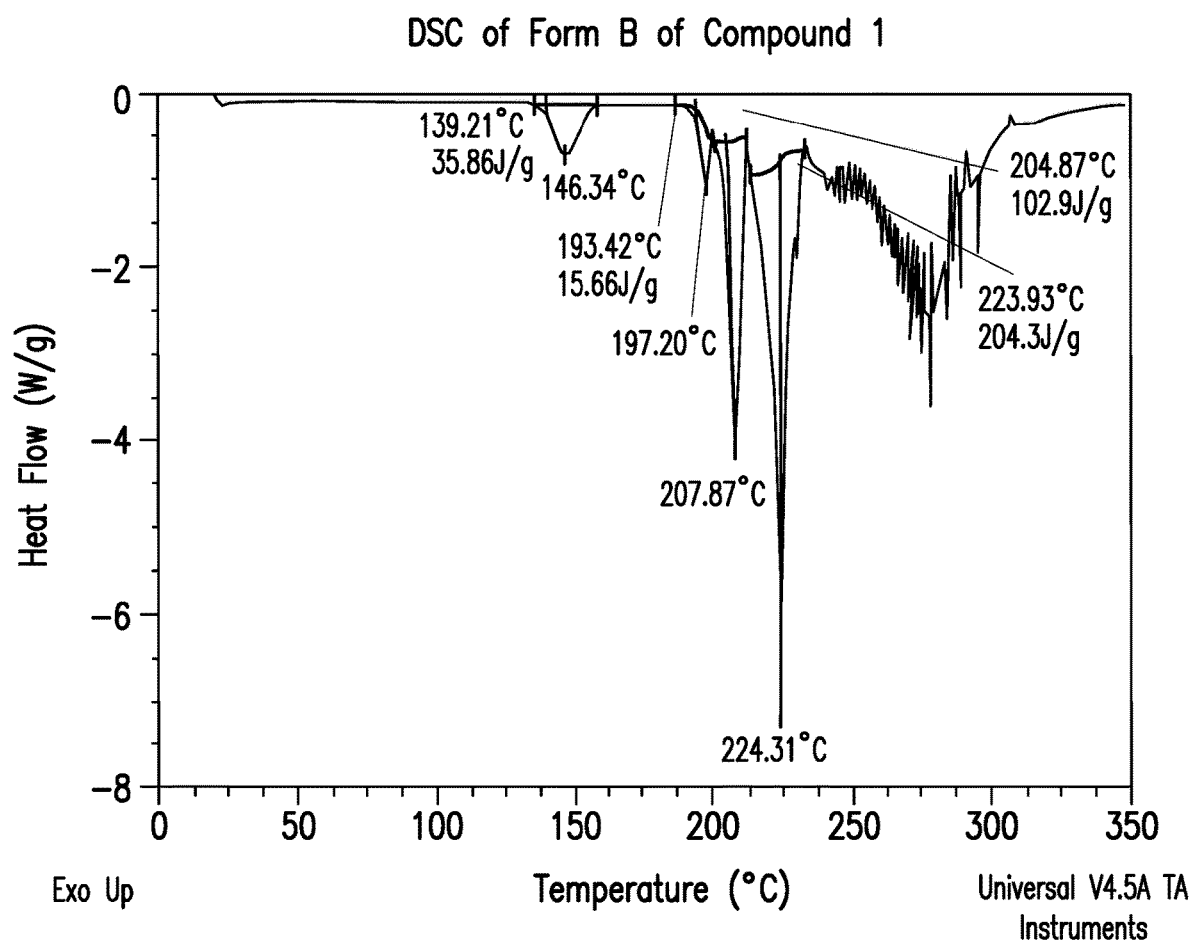

FIG. 12 provides a representative DSC thermogram of Form B of Compound 1.

Figure 13:
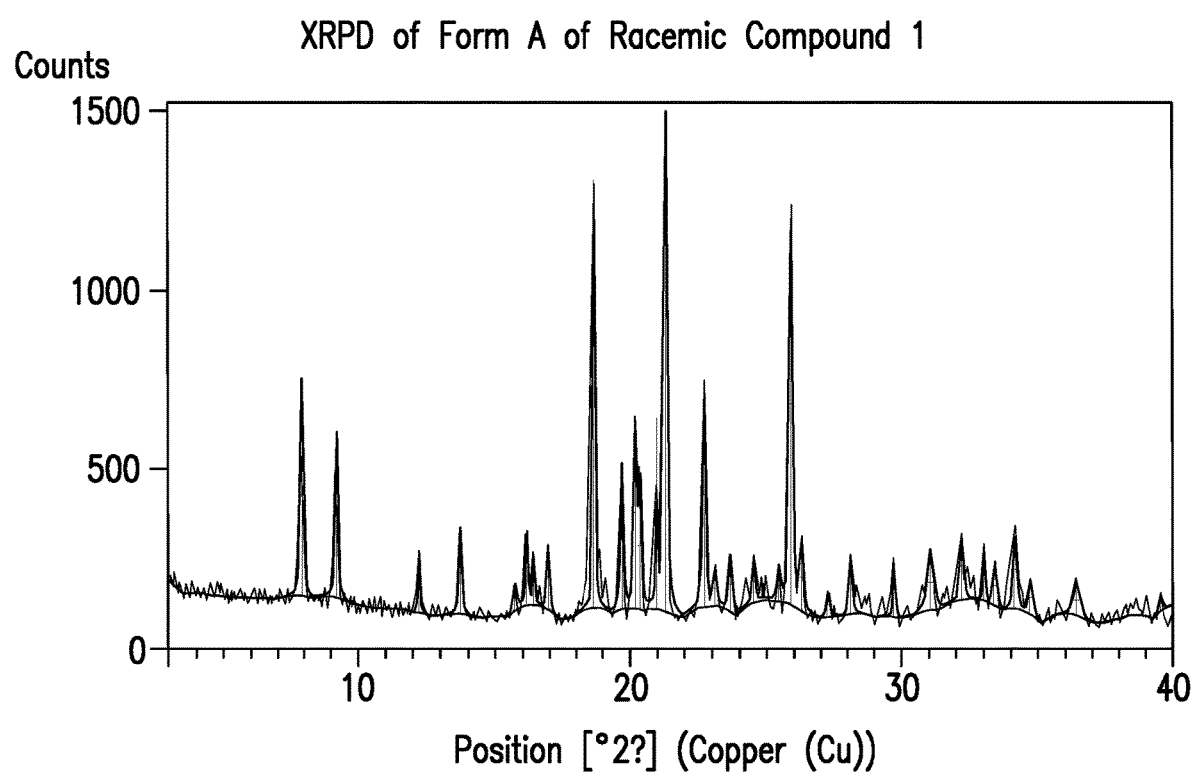

FIG. 13 provides a representative XRPD pattern of Form A of racemic Compound 1.

Figure 14:
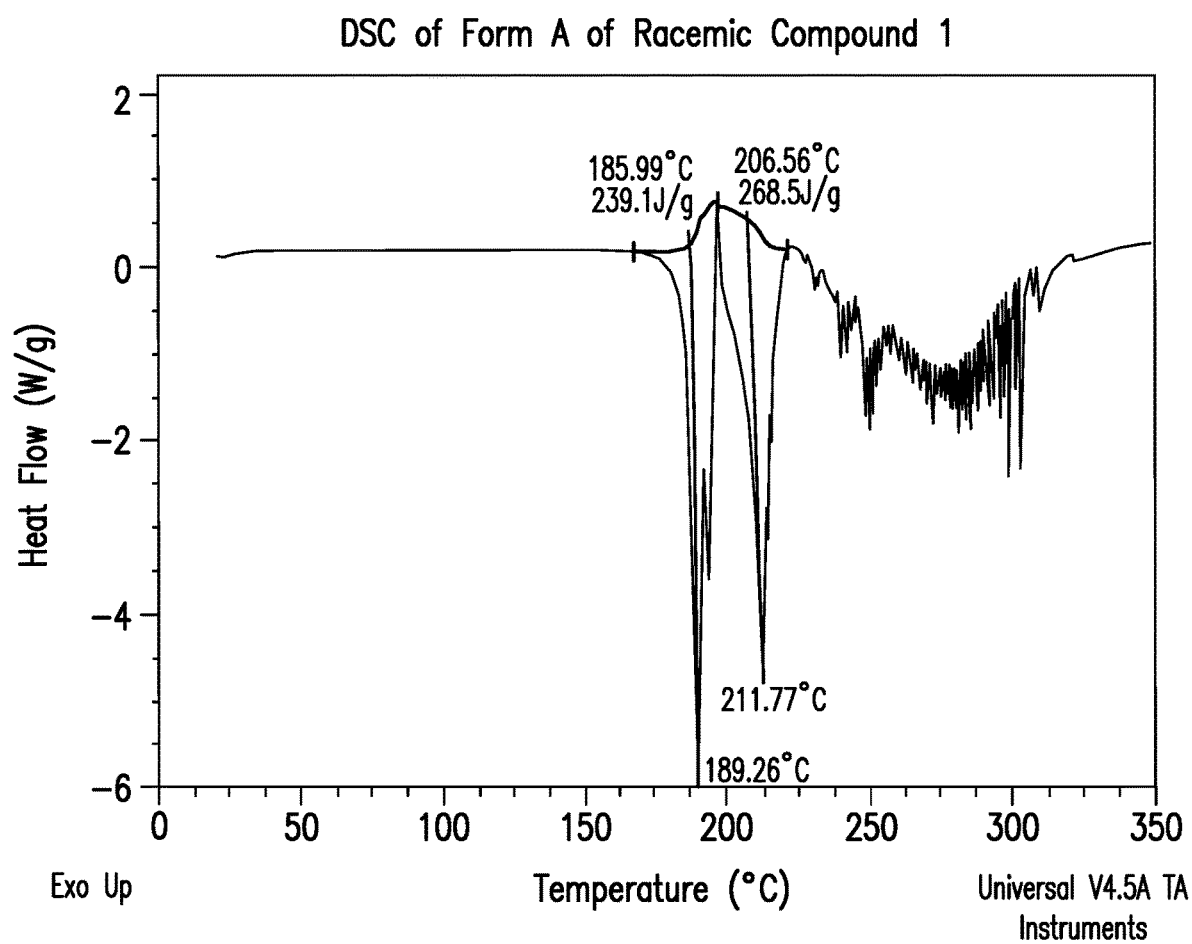

FIG. 14 provides a representative DSC thermogram of Form A of racemic Compound 1.

Figure 15:
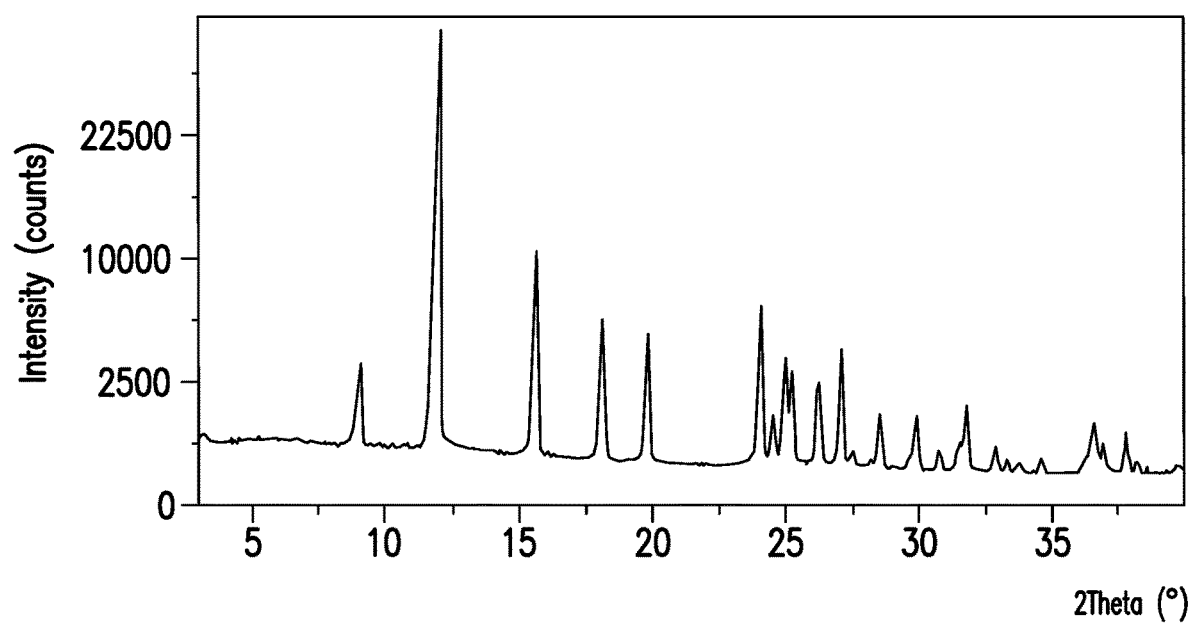

FIG. 15 provides a representative XRPD pattern of Form A of Compound 35.

Figure 16:
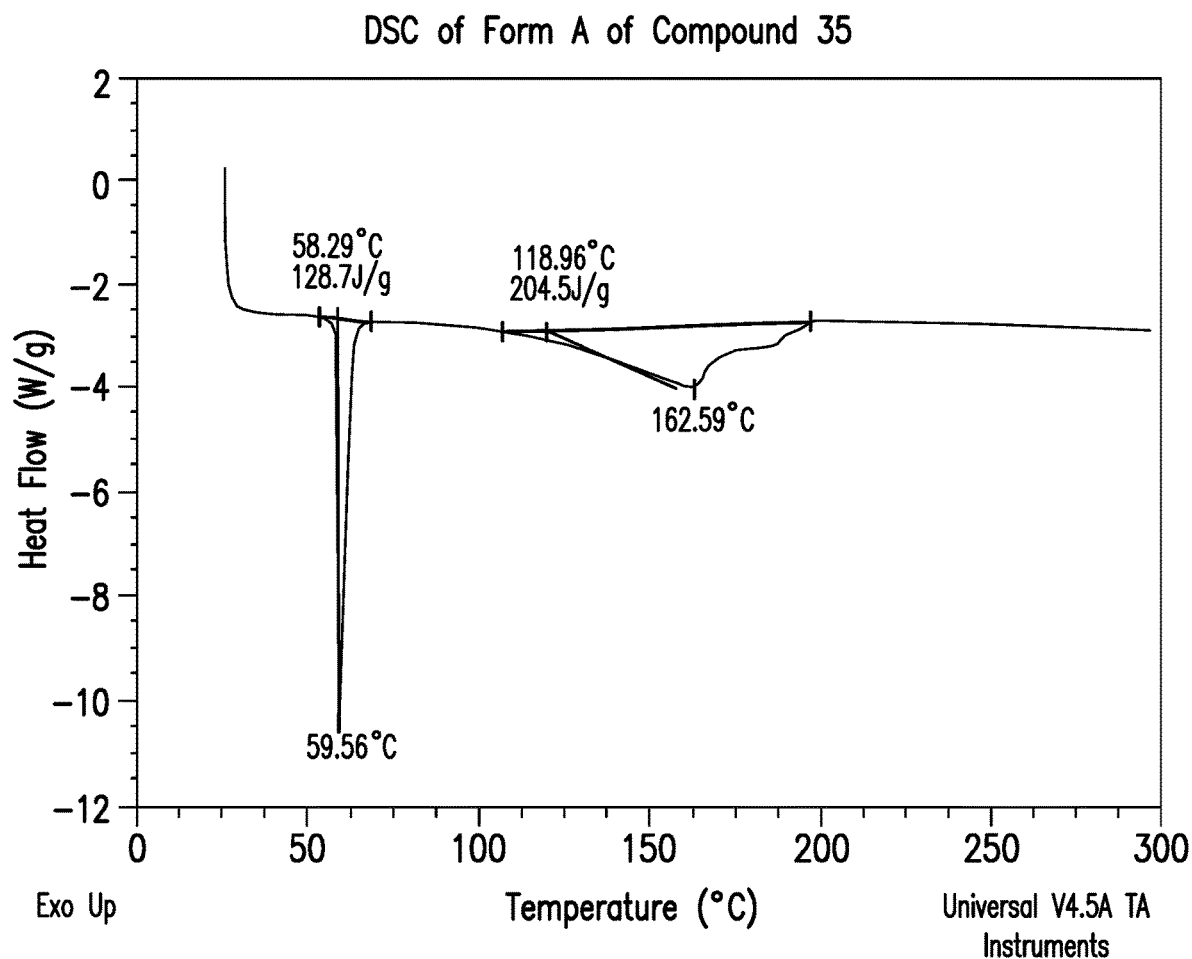

FIG. 16 provides a representative DSC thermogram of Form A of Compound 35.

Figure 17:
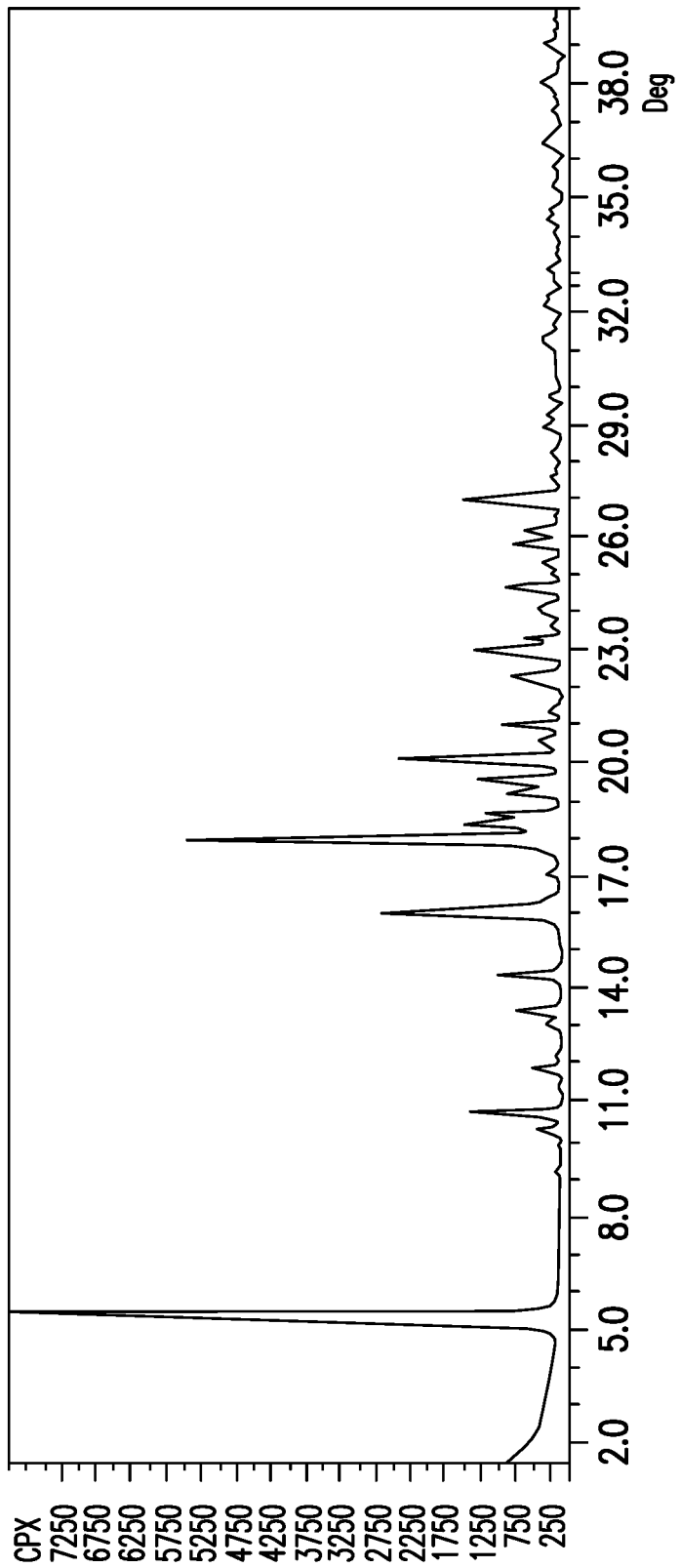

FIG. 17 provides a representative XRPD pattern of Form 1 of Compound 37.

Figure 18:
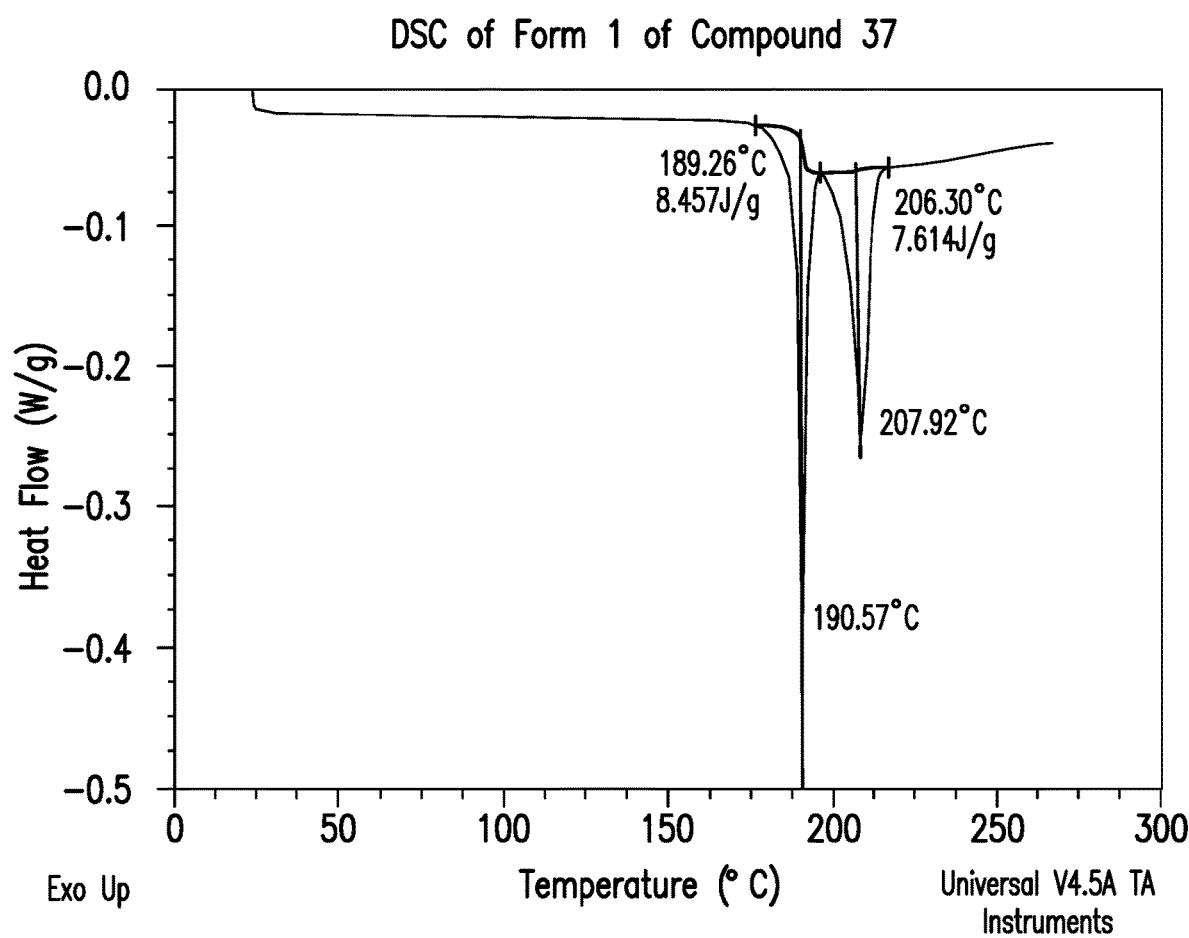

FIG. 18 provides a representative DSC thermogram of Form 1 of Compound 37.

Figure 19A:
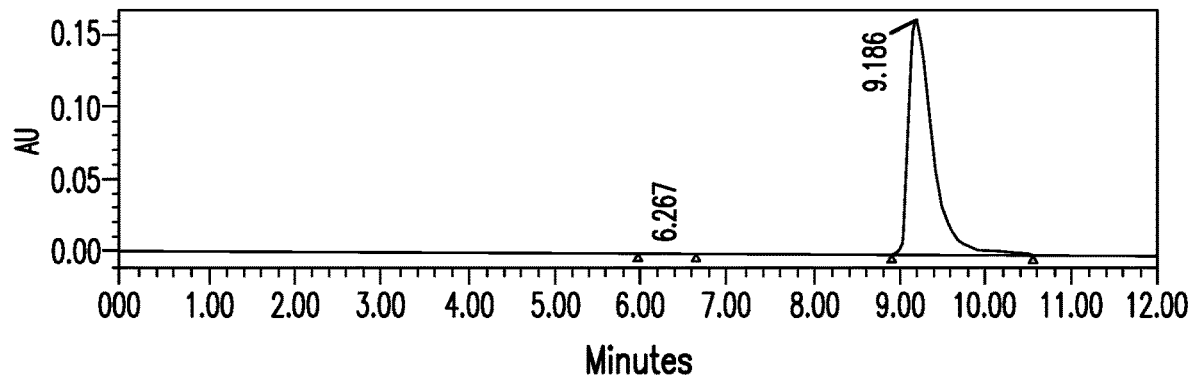

FIG. 19A provides a chiral HPLC chromatogram from a typical reaction of preparing Compound 37 from Compound 35.

Figure 19B:
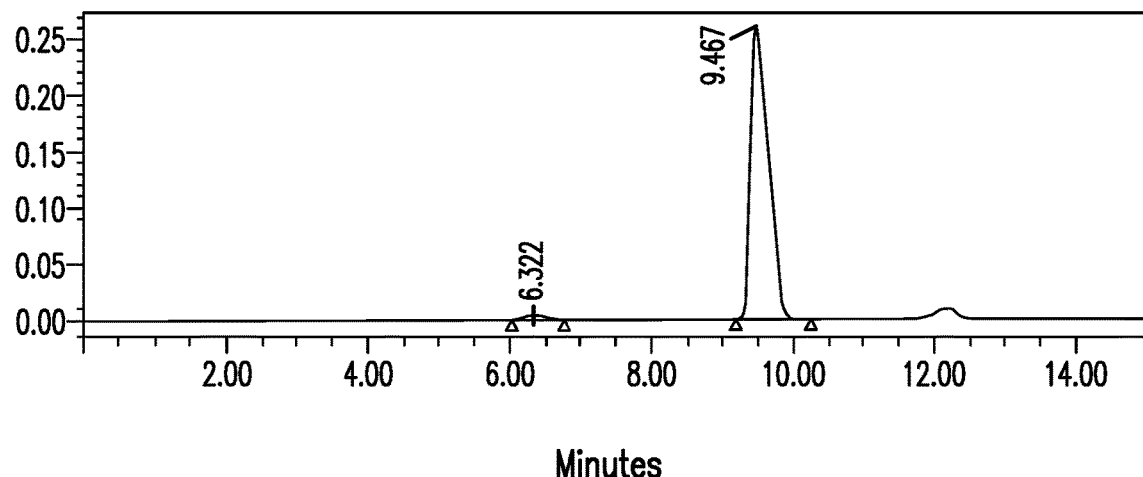

FIG. 19B provides a chiral HPLC chromatogram from an a typical reaction of preparing Compound 37 from Compound 35.

Figure 20:
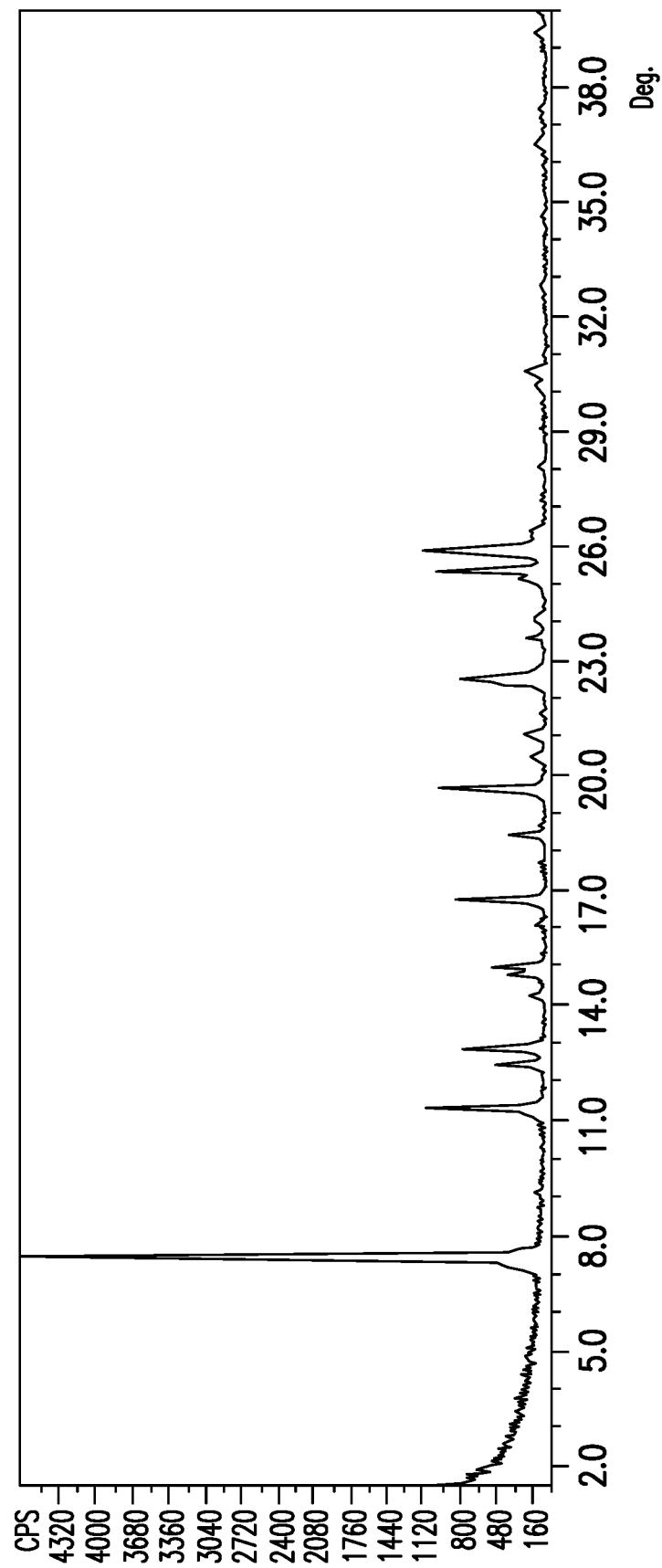

FIG. 20 provides a representative XRPD pattern of Form 1 of racemic Compound 37.

Figure 21:
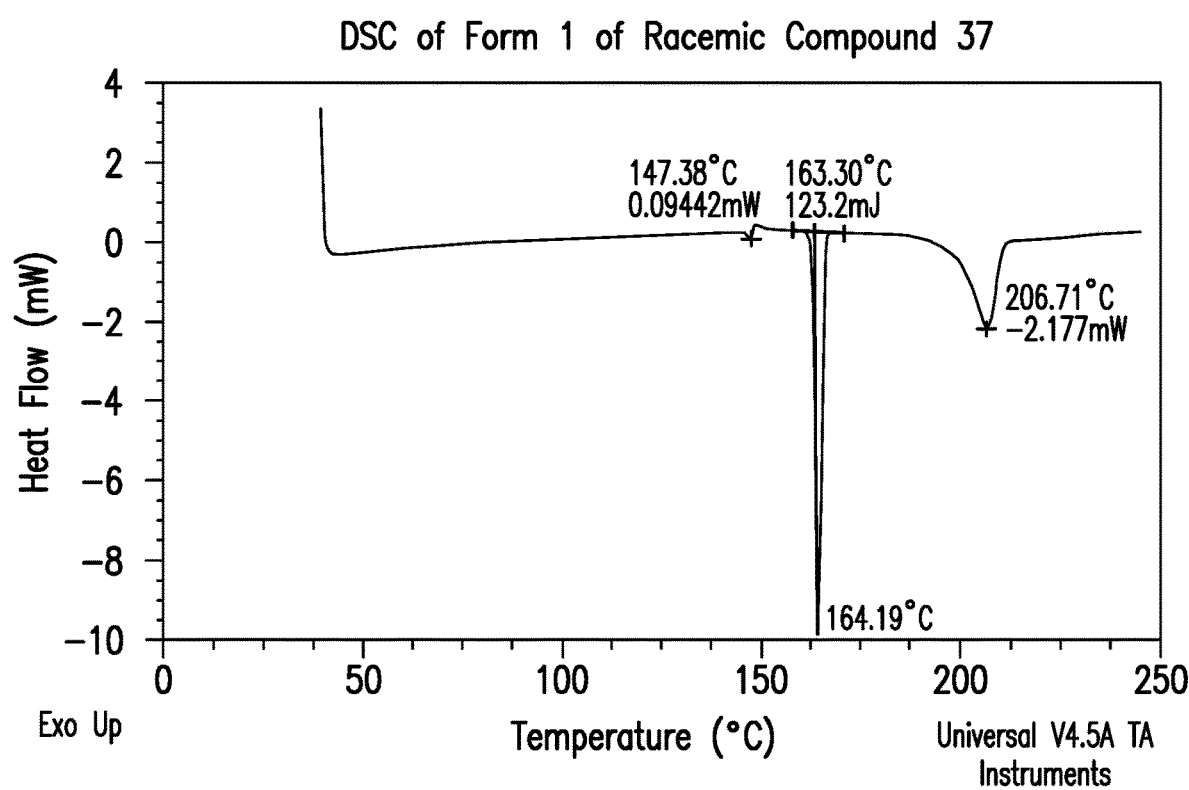

FIG. 21 provides a representative DSC thermogram of Form 1 of racemic Compound 37.

Figure 22:
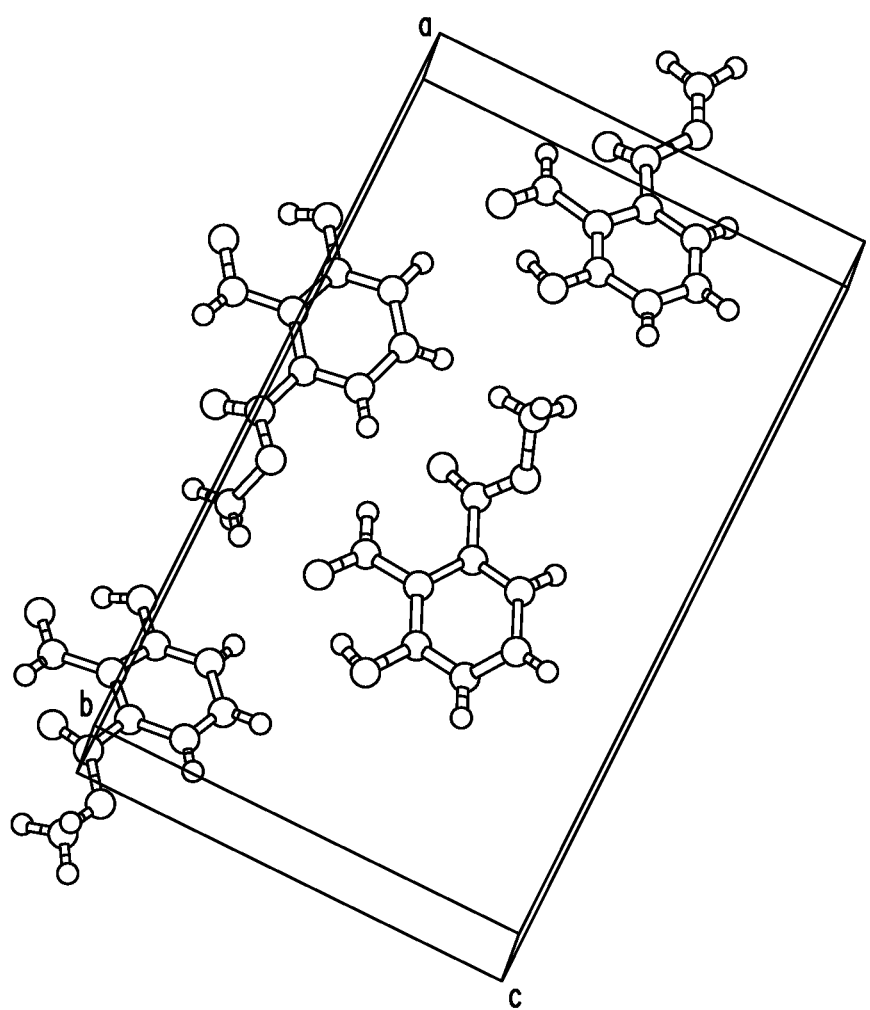

FIG. 22 provides a representative crystal molecular structure of Form A of Compound 35.

Figure 23:
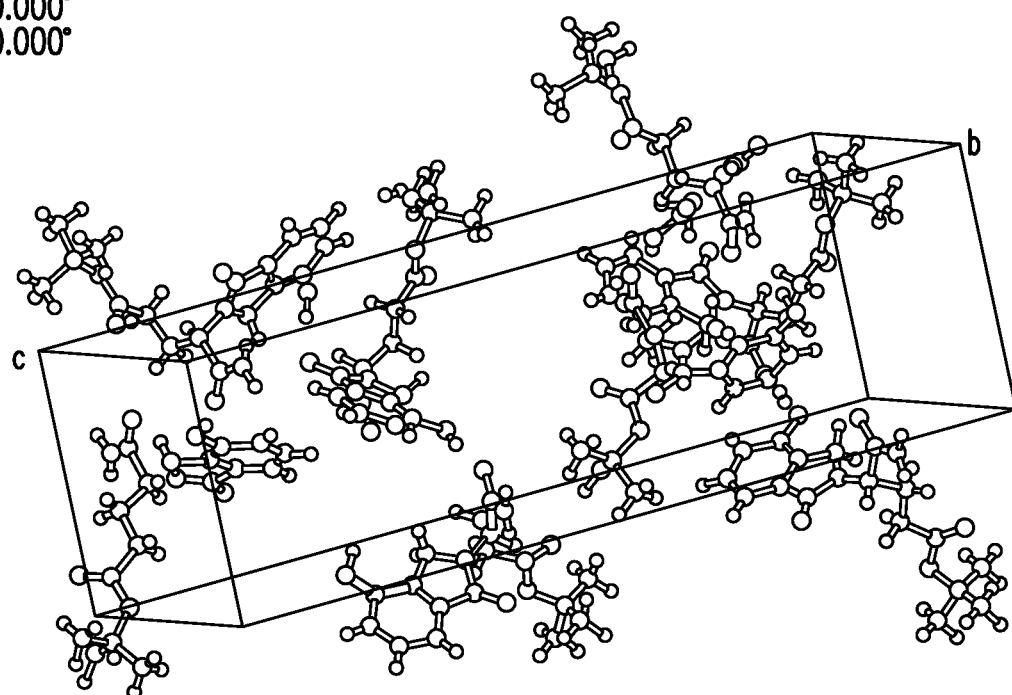

FIG. 23 provides a representative crystal molecular structure of Form 1 of Compound 37.

5. DETAILED DESCRIPTION

5.1 Definition

As used herein and unless otherwise indicated, the term "process(es)" provided herein refers to the methods provided herein which are useful for preparing a compound provided herein. Modifications to the methods provided herein (e.g., starting materials, reagents, protecting groups, solvents, temperatures, reaction times, purification) are also encompassed by the present disclosure. In general, the technical teaching of one embodiment provided herein can be combined with that disclosed in any other embodiments provided herein.

The use of the word "a" or "an" when used in conjunction with the term "comprising" in the claims and/or the specification can mean "one", but it is also consistent with the meaning of "one or more", "at least one" and "one or more than one."

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the terms "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein, and unless otherwise indicated, the term "transforming" refers to subjecting the compound at hand to reaction conditions suitable to effect the formation of the desired compound at hand.

As used herein, and unless otherwise indicated, the term "salt" includes, but is not limited to, salts of acidic or basic groups that may be present in the compounds provided herein. Compounds that are basic in nature are capable of forming a wide variety of salts with various inorganic and organic acids. The acids that may be used to prepare salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

If the stereochemistry of a structure or a portion thereof is not indicated, e.g., with bold or dashed lines, the structure or portion thereof is to be interpreted as encompassing all enantiomerically pure, enantiomerically enriched, diastereomerically pure, diastereomerically enriched, and racemic mixtures of the compounds.

Unless otherwise indicated, the terms "enantiomerically enriched" and "enantiomerically pure," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, and even such as at least 80% by weight. In some embodiments, the enrichment can be much greater than 80% by weight, providing a "substantially optically enriched," "substantially enantiomerically enriched," "substantially enantiomerically pure" or a "substantially non-racemic" preparation, which refers to preparations of compositions which have at least 85% by weight of one enantiomer relative to other enantiomer, such as at least 90% by weight, and such as at least 95% by weight. In one embodiment, the compositions have about 99% by weight of one enantiomer relative to other enantiomer. In one embodiment, the compositions have greater than at least 99% by weight of one enantiomer relative to other enantiomer. In some embodiments, the enantiomerically enriched composition has a higher potency with respect to therapeutic utility per unit mass than does the racemic mixture of that composition.

As used herein and unless otherwise specified, the terms "solid form" and related terms refer to a physical form which is not predominantly in a liquid or a gaseous state. As used herein, the terms "solid form" and "solid forms" encompass semi-solids. Solid forms may be crystalline, amorphous, partially crystalline, partially amorphous, or mixtures of forms.

The solid forms provided herein may have varying degrees of crystallinity or lattice order. The solid forms provided herein are not limited by any particular degree of crystallinity or lattice order, and may be 0-100% crystalline. Methods of determining the degree of crystallinity are known to those of ordinary skill in the, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms provided herein are about 0, 5, 10, 15, 20, 25, 30, 35, 40, 45, 50, 55, 60, 65, 70, 75, 80, 85, 90, 95 or 100% crystalline.

As used herein and unless otherwise specified, the term "crystalline" and related terms used herein, when used to describe a substance, component, product, or form, mean that the substance, component, product, or form is substantially crystalline, for example, as determined by X-ray diffraction. See, e.g., *Remington: The Science and Practice of Pharmacy*, $21^{st}$ edition, Lippincott, Williams and Wilkins, Baltimore, Md. (2005); *The United States Pharmacopeia*, $23^{rd}$ edition, 1843-1844 (1995).

As used herein and unless otherwise specified, the term "crystal form," "crystal forms," and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, co-crystals of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous form(s) and/or other crystal form(s) on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

Unless otherwise specified, the terms "polymorph," "polymorphic form," "polymorphs," "polymorphic forms," and related terms herein refer to two or more crystal forms that consist essentially of the same molecule, molecules or ions. Like different crystal forms, different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing (for example, one polymorph might be more likely to form solvates or might be difficult to filter and wash free of impurities, and particle shape and size distribution might be different between polymorphs).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. In certain embodiments, an amorphous form of a substance may comprise additional components or ingredients (for example, an additive, a polymer, or an excipient that may serve to further stabilize the amorphous form). In certain embodiments, amorphous form may be a solid solution.

Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

Solid forms may exhibit distinct physical characterization data that are unique to a particular solid form, such as the crystal forms provided herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms provided herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis variation.

As used herein, and unless otherwise indicated, the term "halo", "halogen", or the like means —F, —Cl, —Br, or —I.

As used herein, and unless otherwise indicated, the term "alkyl" means a saturated, monovalent, unbranched or branched hydrocarbon chain. Examples of alkyl groups include, but are not limited to, $(C_1$-$C_6)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl. Longer alkyl groups include heptyl, octyl, nonyl and decyl groups. An alkyl group can be unsubstituted or substituted with one or more suitable substituents. The alkyl groups may also be isotopologues of the natural abundance alkyl groups by being enriched in isotopes of carbon and/or hydrogen (i.e., deuterium or tritium). As used herein, and unless otherwise indicated, the term "alkenyl" means an unbranched or branched monovalent hydrocarbon chain, which contains one or more carbon-carbon double bonds. As used herein, and unless otherwise indicated, the term "alkynyl" means an unbranched or branched monovalent hydrocarbon chain, which contains one or more carbon-carbon triple bonds.

As used herein, and unless otherwise indicated, the term "alkoxy" means an alkyl group that is linked to another group via an oxygen atom (i.e., —O-alkyl). An alkoxy group can be unsubstituted or substituted with one or more suitable substituents. Examples of alkoxy groups include, but are not limited to, $(C_1-C_6)$alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, —O-2-ethyl-1-butyl, —O-butyl, —O-isobutyl, —O-pentyl, —O-isopentyl, —O-neopentyl and —O-hexyl. Longer alkoxy groups include —O-heptyl, —O-octyl, —O-nonyl and, —O-decyl groups. The alkoxy groups may also be isotopologues of the natural abundance alkoxy groups by being enriched in isotopes of carbon, oxygen and/or hydrogen (i.e., deuterium or tritium).

As used herein, and unless otherwise specified, the term "cycloalkyl" or "carbocyclyl" means a species of alkyl, which is cyclic and contains from 3 to 15, 3 to 9, 3 to 6, or 3 to 5 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more substituents. In some embodiments, a cycloalkyl may be a cycloalkyl fused with aryl or heteroaryl groups.

As used herein, and unless otherwise specified, the term "heterocycloalkyl" or "heterocyclyl" means a cycloalkyl in which one or more, in some embodiments, 1 to 3, carbon atoms are replaced by heteroatoms such as, but not limited to, N, S, and O. In some embodiments, a heterocycloalkyl group contains from 3 to 15, 3 to 9, 3 to 6, or 3 to 5 carbon and hetero atoms. In some embodiments, a heterocycloalkyl may be a heterocycloalkyl fused with aryl or heteroaryl groups. When a prefix such as $C_{3-6}$ is used to refer to a heterocycloalkyl group, the number of carbons (3-6, in this example) is meant to include the heteroatoms as well. For example, a $C_{3-6}$ heterocycloalkyl group is meant to include, for example, tetrahydropyranyl (five carbon atoms and one heteroatom replacing a carbon atom).

As used herein, and unless otherwise specified, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Specifically, the aryl group may be a mono-, bi-, or tricyclic ring. Representative aryl groups include phenyl, anthracenyl, fluorenyl, indenyl, azulenyl, phenanthrenyl and naphthyl.

As used herein, and unless otherwise specified, the term "heteroaryl" refers to a monocyclic or multicyclic aromatic ring system, in certain embodiments, of about 5 to about 15 members where one or more, in some embodiments, 1 to 3, of the atoms in the ring system is a heteroatom, that is, an element other than carbon, including but not limited to, N, O or S. The heteroaryl group may be optionally fused to a benzene ring. Heteroaryl groups include, but are not limited to, furyl, imidazolyl, indolinyl, pyrrolidinyl, pyrimidinyl, tetrazolyl, thienyl, pyridyl, pyrrolyl, N-methylpyrrolyl, quinolinyl and isoquinolinyl.

As used herein, and unless otherwise indicated, the term "alcohol" means any compound substituted with an —OH group. The alcohol group may also be isotopologues of the natural abundance alcohol groups by being enriched in isotopes of oxygen and/or hydrogen (i.e., deuterium or tritium).

As used herein, and unless otherwise indicated, the term "amino" or "amino group" means a monovalent group of the formula —$NH_2$, —NH(alkyl), —NH(aryl), —N(alkyl)$_2$, —N(aryl)$_2$ or —N(alkyl)(aryl). The amino groups may also be isotopologues of the natural abundance amino groups by being enriched in isotopes of carbon, nitrogen and/or hydrogen (i.e., deuterium or tritium).

Unless otherwise indicated, the compounds provided herein, including intermediates useful for the preparation of the compounds provided herein, which contain reactive functional groups (such as, without limitation, carboxy, hydroxy, and amino moieties) also include protected derivatives thereof. "Protected derivatives" are those compounds in which a reactive site or sites are blocked with one or more protecting groups (also known as blocking groups). Suitable protecting groups for carboxy moieties include benzyl, t-butyl, and the like as well as isotopologues of the like. Suitable protecting groups for amino and amido groups include acetyl, trifluoroacetyl, t-butyloxycarbonyl, benzyloxycarbonyl, and the like. Suitable protecting groups for hydroxy include benzyl and the like. Other suitable protecting groups are well known to those of ordinary skill in the art. The choice and use of protecting groups and the reaction conditions to install and remove protecting groups are described in *Greene's Protective Groups in Organic Synthesis,* 4th edition, John Wiley & Sons, New York, 2007, which is incorporated herein by reference in its entirety.

Amino protecting groups known in the art include those described in detail in T W. Green, *Protective Groups in Organic Synthesis.* Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl groups), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups; wherein each instance of R$^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)

OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups.

each instance of R$^{ee}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups.

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S.

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$X, —NH(C$_{1-6}$ alkyl)$_2$X, —NH$_2$(C$_{1-6}$ alkyl)X, —NH$_3$X, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S;

wherein X$^-$ is a counterion.

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like) and carboxylate ions (e.g., acetate, ethanoate, propanoate, benzoate, glycerate, lactate, tartrate, glycolate, and the like). Counterions also include chrial counterions, some of which may be useful for chiral resolution of racemic mixtures. Exemplary chiral counterions include (S)-(+) mandelic acid, (D)-(+) tartaric acid, (+) 2,3-dibenzoyl-D-tartaric acid, N-Acetyl-L-leucine, and N-Acetyl-L-phenylalanine.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethyl silylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromo-ethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methyl sulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1(p-phenylazophenyl)ethyl carbamate, 1-methyl-1-phenylethyl carbamate, 1-methyl-1(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethyl silyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrob enzenesulfenamide, pentachlorobenzenesulfenamide, 2-nitro-4-methoxybenzenesulfenamide, triphenylmethylsulfenamide and 3-nitropyridinesulfenamide (Npys).

As used herein, and unless otherwise indicated, the term "hydroxyl protecting group" refers to a protecting group suitable for preventing undesired reactions at a hydroxyl group. Examples of hydroxyl protecting groups include, but are not limited to, allyl, methyl, 2-methoxyethoxymethyl (MEM), methoxymethyl (MOM), methoxythiomethyl, t-butoxymethyl, tri-isopropylsilyloxymethyl (TOM), ethyl, 1-ethoxyehtyl, isopropyl, t-butyl, benzyl, trityl (Tr), dimethoxytrityl (DMT), monomethoxytrityl (MMT), p-methoxybenzyl (PMB), acetyl, chloroacetyl, trichloroacetyl, trifluoroacetyl, pivaloyl (Piv), benzoyl, p-phenylbenzoyl, trimethylsilyl (TMS), triisopropylsilyl (TIPS), t-butyldimethylsilyl (TBDMS), and tetrahydropyranyl. Additional examples of hydroxyl protecting groups are described in *Greene's Protective Groups in Organic Synthesis*, 4th edition, John Wiley & Sons, New York, 2007, which is incorporated herein by reference in its entirety.

As used herein, and unless otherwise indicated, acronyms or symbols for groups or reagents have the following definition: HPLC=high performance liquid chromatography; THF=tetrahydrofuran; CH$_3$CN=acetonitrile; HOAc= acetic acid; DCM=dichloromethane.

As used herein, and unless otherwise indicated, the term "substituted" or "substitution," when used to describe a chemical structure or moiety, refers to a derivative of that structure or moiety wherein one or more of its hydrogen atoms is replaced with a substituent such as, but not limited to: alkyl, alkenyl, alkynyl, and cycloalkyl; alkoxyalkyl; aroyl; halo; haloalkyl (e.g., trifluoromethyl); heterocycloalkyl; haloalkoxy (e.g., trifluoromethoxy); hydroxy; alkoxy; cycloalkyloxy; heterocylooxy; oxo; alkanoyl; aryl; heteroaryl (e.g., indolyl, imidazolyl, furyl, thienyl, thiazolyl, pyrrolidyl, pyridyl, and pyrimidyl); arylalkyl; alkylaryl; heteroaryl; heteroarylalkyl; alkylheteroaryl; heterocyclo; heterocycloalkyl-alkyl; aryloxy, alkanoyloxy; amino; alkylamino; arylamino; arylalkylamino; cycloalkylamino; heterocycloamino; mono- and di-substituted amino; alkanoylamino; aroylamino; aralkanoylamino; aminoalkyl; carbamyl (e.g., CONH$_2$); substituted carbamyl (e.g., CONH-alkyl, CONH-aryl, CONH-arylalkyl or instances where there are two substituents on the nitrogen); carbonyl; alkoxycarbonyl; carboxy; cyano; ester; ether; guanidino; nitro; sulfonyl; alkylsulfonyl; arylsulfonyl; arylalkylsulfonyl; sulfonamido (e.g., SO$_2$NH$_2$); substituted sulfonamido;

thiol; alkylthio; arylthio; arylalkylthio; cycloalkylthio; heterocyclothio; alkylthiono; arylthiono; and arylalkylthiono. In some embodiments, a substituent itself may be substituted with one or more chemical moieties such as, but not limited to, those described herein.

As used herein, and unless otherwise indicated, the terms "about" and "approximately" are used to specify that the values given are approximate. For example, the term "about," where it is used in connection with reaction temperatures, denotes that the temperature deviations within 30%, 25%, 20%, 15%, 10%, or 5% are encompassed by the temperature indicated. Similarly, the term "about," where it is used in connection with reaction time, denotes that the time period deviations within 30%, 25%, 20%, 15%, 10%, or 5% are encompassed by the time period indicated.

As used herein, and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiment, the value of XRPD peak position may vary by up to ±0.2 degrees 2θ while still describing the particular XRPD peak. As used herein, a tilde (i.e.,"~") preceding a numerical value or range of values indicates "about" or "approximately."

As used herein, and unless otherwise indicated, the term "hydrogenation" refers to a chemical process that adds hydrogen atom to an unsaturated bond.

As used herein, and unless otherwise indicated, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom, and "natural isotopic composition" refers to the naturally occurring isotopic composition or abundance for a given atom.

The disclosure can be understood more fully by reference to the following detailed description and illustrative examples, which are intended to exemplify non-limiting embodiments.

Although most embodiments and examples provided herein are directed to the (S)-enantiomer of a compound, it is to be understood that the corresponding (R)-enantiomer of a compound can be prepared by the provided processes when the stereochemistry of chiral reactant, reagent, solvent, catalyst, ligand or the like is reversed.

5.2 Processes

Provided herein are processes for the preparation of a compound of Formula (I):

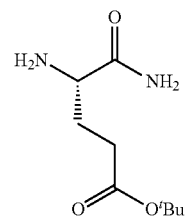

or a solvate, hydrate, enantiomer, mixture of enantiomers, or isotopologue thereof. A compound of Formula (I) has a chemical name of (S)-tert-butyl 4,5-diamino-5-oxopentanoate. The processes comprise an optional step of preparing a salt of the compound.

In certain embodiments, the processes provided herein result in improved chiral purity for one or more intermediates and/or products throughout the route.

Also provided herein are processes for the preparation of a compound of Formula (XIV):

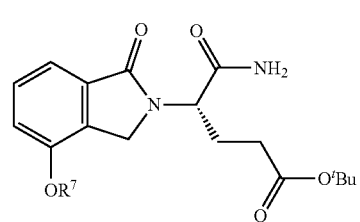

or a salt, solvate, hydrate, enantiomer, mixture of enantiomers, or isotopologue thereof. The processes utilize a compound of Formula (I) as one of the starting material. In one embodiment, the processes involve a reductive amination reaction between a compound of Formula (I) and a compound of Formula (XV) (or a synthetic equivalent thereof).

Also provided herein are processes for the preparation of a compound of Formula (XV):

or a salt, solvate, hydrate, enantiomer, mixture of enantiomers, or isotopologue thereof. The compound of Formula (XV) can be used as another starting material for the preparation of a compound of Formula (XIV). In one embodiment, the processes involve a formylation reaction of a compound of Formula (XVI).

5.2.1 Process 1 for the Preparation of a Compound of Formula (I)

In one embodiment, provided herein are processes for the preparation of a compound of Formula (I), or a solvate, hydrate, enantiomer, mixture of enantiomers, or isotopologue thereof, comprising a ring-opening reaction of a N-protected oxazolidin-5-one moiety with ammonia or a protected amine. The processes comprise an optional step of preparing a salt of the compound.

In one embodiment, provided herein is a process for preparing a compound of Formula (I):

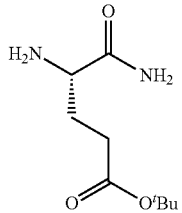
(I)

or a salt, solvate, hydrate, enantiomer, mixture of enantiomers, or isotopologue thereof, comprising
(a) contacting a compound of Formula (II):

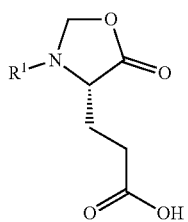
(II)

or a solvate, hydrate, enantiomer, mixture of enantiomers, or isotopologue thereof, wherein $R^1$ is a suitable amino protecting group, with $NH_2—R^2$ wherein $R^2$ is hydrogen or a suitable amino protecting group, to provide a compound of Formula (III):

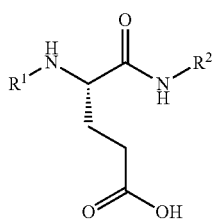
(III)

or a solvate, hydrate, enantiomer, mixture of enantiomers, or isotopologue thereof;
(b) transforming the compound of Formula (III), or a solvate, hydrate, enantiomer, mixture of enantiomers, or isotopologue thereof, to a compound of Formula (IV):

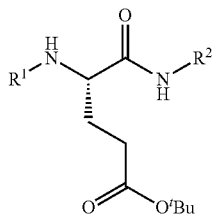
(IV)

or a solvate, hydrate, enantiomer, mixture of enantiomers, or isotopologue thereof;
(c) deprotecting the —NH—$R^1$ group and, when $R^2$ is a suitable amino protecting group, deprotecting the —NH—$R^2$ group to provide a compound of Formula (I), or a solvate, hydrate, enantiomer, mixture of enantiomers, or isotopologue thereof; and
(d) optionally converting the compound of Formula (I), or a solvate, hydrate, enantiomer, mixture of enantiomers, or isotopologue thereof, to a salt of the compound.

In one embodiment, provided herein is a process for preparing a compound of Formula (I):

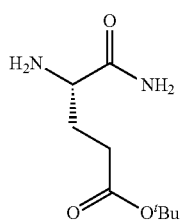
(I)

or a salt, solvate, hydrate, enantiomer, mixture of enantiomers, or isotopologue thereof, comprising
(c) deprotecting the —NH—$R^1$ group and, when $R^2$ is a suitable amino protecting group, deprotecting the —NH—$R^2$ group in a compound of Formula (IV):

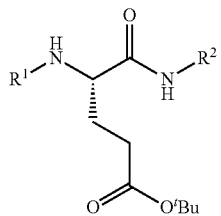
(IV)

or a solvate, hydrate, enantiomer, mixture of enantiomers, or isotopologue thereof, wherein $R^1$ is a suitable amino protecting group, and $R^2$ is hydrogen or a suitable amino protecting group, to provide a compound of Formula (I), or a solvate, hydrate, enantiomer, mixture of enantiomers, or isotopologue thereof; and
(d) optionally converting the compound of Formula (I), or a solvate, hydrate, enantiomer, mixture of enantiomers, or isotopologue thereof, to a salt of the compound.

In one embodiment, the compound of Formula (IV), or a solvate, hydrate, enantiomer, mixture of enantiomers, or isotopologue thereof, is prepared by a process comprising
(b) transforming a compound of Formula (III):

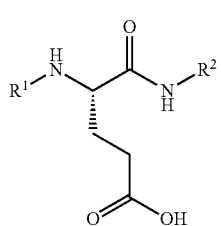
(III)

or a solvate, hydrate, enantiomer, mixture of enantiomers, or isotopologue thereof, to a compound of Formula (IV), or a solvate, hydrate, enantiomer, mixture of enantiomers, or isotopologue thereof.

In one embodiment, the compound of Formula (III), or a solvate, hydrate, enantiomer, mixture of enantiomers, or isotopologue thereof, is prepared by a process comprising (a) contacting a compound of Formula (II):

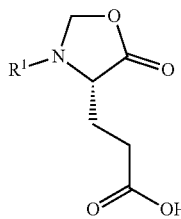

(II)

or a solvate, hydrate, enantiomer, mixture of enantiomers, or isotopologue thereof, with $NH_2$—$R^2$ to provide a compound of Formula (III), or a solvate, hydrate, enantiomer, mixture of enantiomers, or isotopologue thereof.

In one embodiment, $R^2$ is hydrogen, i.e., $NH_2$—$R^2$ is $NH_3$. In one embodiment, the $NH_3$ in step (a) is provided in the form of gaseous ammonia. In one embodiment, the $NH_3$ in step (a) is provided in the form of an ammonia solution. In one embodiment, the ammonia solution is an ammonia solution in water (e.g., $NH_4OH$). In one embodiment, the ammonia solution is an ammonia solution in an alcohol. In one embodiment, the alcohol is methanol, ethanol, n-propanol, or isopropanol, or a mixture thereof. In one embodiment, the ammonia solution is an ammonia solution in MeOH.

In one embodiment, the $NH_3$ in step (a) is provided in the form of ammonium salt. In one embodiment, the ammonium salt is $(NH_4)_2CO_3$, $NH_4HCO_3$, $NH_4OAc$, $NH_4H_2PO_4$, $(NH_4)_2HPO_4$, or $(NH_4)_3PO_4$. In one embodiment, the $NH_3$ in step (a) is provided in the form of $NH_4HCO_3$.

In one embodiment, $R^2$ is a suitable amino protecting group. In one embodiment, the deprotection of the —NH—$R^1$ group and the deprotection of the —NH—$R^2$ group in step (c) are conducted separately. In one embodiment, the deprotection of the —NH—$R^1$ group and the deprotection of the —NH—$R^2$ group in step (c) are conducted simultaneously.

In one embodiment, $R^2$ is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (Pf), bis(trimethylsilyl)methyl, t-butoxycarbonyl (Boc), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, $R^2$ is benzyl (Bn), 4-methoxybenzyl (PMB), or 3,4-dimethoxybenzyl (DMPM). In one embodiment, $R^2$ is 1-phenylethyl. In one embodiment, $R^2$ is (S)-1-phenylethyl. In one embodiment, $R^2$ is (R)-1-phenylethyl.

In one embodiment, $R^1$ is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (Pf), bis(trimethylsilyl)methyl, t-butoxycarbonyl (Boc), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, $R^1$ is benzyl (Bn), 4-methoxybenzyl (PMB), 3,4-dimethoxybenzyl (DMPM), benzyloxycarbonyl (Cbz), or p-methoxybenzyloxycarbonyl (Moz). In one embodiment, $R^1$ is benzyloxycarbonyl (Cbz).

In one embodiment, step (c) occurs under a hydrogenation condition. In one embodiment, the hydrogenation occurs in the presence of a Pd catalyst. In one embodiment, the Pd catalyst is Pd/C. In one embodiment, the hydrogenation occurs in the presence of a Palladium, Platinum, Rhodium, or Ruthenium catalyst on different supports that include carbons, alumina, alkaline earth carbonates, clays, ceramics, and celite. In one embodiment, the hydrogenation occurs in a solvent of MeOH. In one embodiment, the hydrogenation occurs in a solvent of ethanol, isopropanol, 1-propanol, butanol, THF, 2-MeTHF, MTBE, isopropyl acetate, ethyl acetate, DMF, DMAc, or NMP. In one embodiment, the hydrogenation occurs under a transfer hydrogenation condition. In one embodiment, the transfer hydrogenation condition includes cyclohexene, cyclohexadiene, formic acid, or ammonium formate.

In one embodiment, step (b) comprises reacting the compound of Formula (III), or a solvate, hydrate, enantiomer, mixture of enantiomers, or isotopologue thereof, with isobutylene or equivalent to provide a compound of Formula (IV), or a solvate, hydrate, enantiomer, mixture of enantiomers, or isotopologue thereof. In one embodiment, the isobutylene equivalent is t-butyl 2,2,2-trichloroacetimidate. In one embodiment, the isobutylene equivalent is O-t-Bu-DIC isourea

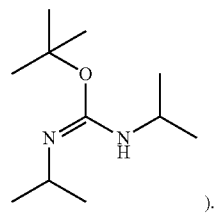

In one embodiment, the O-t-Bu-DIC isourea is formed by reacting diisopropylcarbodiimide (DIC) with t-butanol and a Cu(I) salt. In one embodiment, the O-t-Bu-DIC isourea is formed by reacting diisopropylcarbodiimide (DIC) with t-butanol and a Cu(I) salt in the presence of oxygen. In one embodiment, the oxygen is present in an amount of up to about 22% of the atmosphere. In one embodiment, the oxygen is present in an amount of from about 1% to about 10% of the atmosphere. In one embodiment, the oxygen is present in an amount of from about 2% to about 6% of the atmosphere. In one embodiment, the oxygen is present in an amount of about 4% of the atmosphere. In one embodiment, the Cu(I) salt is CuCl. In one embodiment, the Cu(I) salt is CuBr. In one embodiment, the Cu(I) salt is CuI. Other methods for transforming an acid to a t-butyl ester that are generally known to those of ordinary skill in the art can also be used in step (b).

Step (d) comprises optionally converting the compound of Formula (I), or a solvate, hydrate, enantiomer, mixture of enantiomers, or isotopologue thereof, to a salt of the compound. In one embodiment, the salt is a HCl, HBr, HOAc, or PhSO$_3$H salt. In one embodiment, the salt is a HCl salt. Methods for salt formation that are generally known to those of ordinary skill in the art can be used in step (d).

In one embodiment, the compound of Formula (II), or a solvate, hydrate, enantiomer, mixture of enantiomers, or isotopologue thereof, is prepared by a process comprising contacting a compound of the Formula:

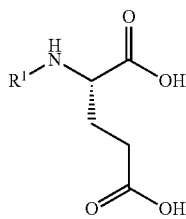

or a solvate, hydrate, enantiomer, mixture of enantiomers, or isotopologue thereof, with a formaldehyde source. In one embodiment, the formaldehyde source is paraformaldehyde. In one embodiment, the formaldehyde source is 1,3,5-trioxane. In one embodiment, the reaction occurs in the presence of an acid. In one embodiment, the acid is p-TsOH. In one embodiment, the acid is MsOH. In one embodiment, the acid is benzenesulfonic acid. In one embodiment, the acid is trifluoromethanesulfonic acid. In one embodiment, the acid is trifluoroacetic acid. In one embodiment, the acid is sulfuric acid. In one embodiment, the acid is trichloroacetic acid. In one embodiment, the acid is present in a catalytic amount. In one embodiment, the reaction occurs in a solvent of PhMe. In one embodiment, the reaction occurs in a solvent of acetonitrile.

In one embodiment, provided herein is a process for preparing a compound of Formula (I):

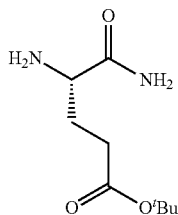

(I)

or a salt, solvate, hydrate, enantiomer, mixture of enantiomers, or isotopologue thereof, comprising (a) contacting Compound 4 of the Formula:

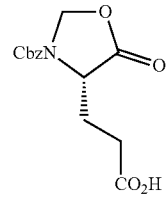

4 or a solvate, hydrate, enantiomer, mixture of enantiomers, or isotopologue thereof, with

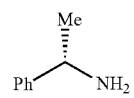

to provide Compound 5 of the Formula:

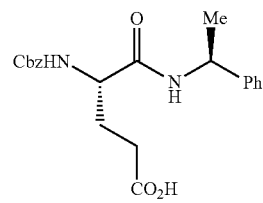

5 or a solvate, hydrate, enantiomer, mixture of enantiomers, or isotopologue thereof;

(b) transforming Compound 5, or a solvate, hydrate, enantiomer, mixture of enantiomers, or isotopologue thereof, to Compound 6 of the Formula:

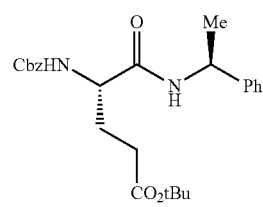

6 or a solvate, hydrate, enantiomer, mixture of enantiomers, or isotopologue thereof;

(c) deprotecting Compound 6, or a solvate, hydrate, enantiomer, mixture of enantiomers, or isotopologue thereof, to provide a compound of Formula (I), or a solvate, hydrate, enantiomer, mixture of enantiomers, or isotopologue thereof; and (d) optionally converting the compound of Formula (I), or a solvate, hydrate, enantiomer, mixture of enantiomers, or isotopologue thereof, to a HCl salt of the compound.

In one embodiment, provided herein is a process for preparing a compound of Formula (I):

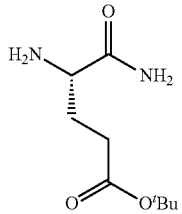

(I)

or a salt, solvate, hydrate, enantiomer, mixture of enantiomers, or isotopologue thereof, comprising (c) deprotecting Compound 6 of the Formula:

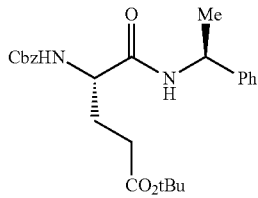

6 or a solvate, hydrate, enantiomer, mixture of enantiomers, or isotopologue thereof, to provide a compound of Formula (I), or a solvate, hydrate, enantiomer, mixture of enantiomers, or isotopologue thereof; and (d) optionally converting the compound of Formula (I), or a solvate, hydrate, enantiomer, mixture of enantiomers, or isotopologue thereof, to a HCl salt of the compound.

In one embodiment, Compound 6, or a solvate, hydrate, enantiomer, mixture of enantiomers, or isotopologue thereof, is prepared by a process comprising (b) transforming Compound 5 of the Formula:

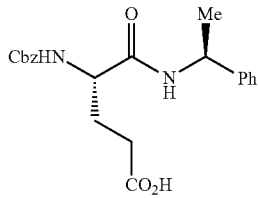

5 or a solvate, hydrate, enantiomer, mixture of enantiomers, or isotopologue thereof, to Compound 6, or a solvate, hydrate, enantiomer, mixture of enantiomers, or isotopologue thereof.

In one embodiment, Compound 5, or a solvate, hydrate, enantiomer, mixture of enantiomers, or isotopologue thereof, is prepared by a process comprising (a) contacting Compound 4 of the Formula:

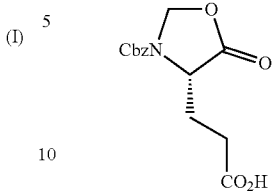

4 or a solvate, hydrate, enantiomer, mixture of enantiomers, or isotopologue thereof, with

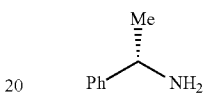

to provide Compound 5, or a solvate, hydrate, enantiomer, mixture of enantiomers, or isotopologue thereof.

In one embodiment, step (a) occurs in a solvent of MeOH.

In one embodiment, step (b) comprises reacting Compound 5, or a solvate, hydrate, enantiomer, mixture of enantiomers, or isotopologue thereof, with t-butyl 2,2,2-trichloroacetimidate. In one embodiment, the reaction occurs in the presence of $BF_3$ etherate. In one embodiment, the reaction occurs in a solvent of DCM.

In one embodiment, step (b) comprises reacting Compound 5, or a solvate, hydrate, enantiomer, mixture of enantiomers, or isotopologue thereof, with O-t-Bu-DIC isourea. In one embodiment, the O-t-Bu-DIC isourea is formed by reacting diisopropylcarbodiimide (DIC) with t-butanol and a Cu(I) salt. In one embodiment, the O-t-Bu-DIC isourea is formed by reacting diisopropylcarbodiimide (DIC) with t-butanol and a Cu(I) salt in the presence of oxygen. In one embodiment, the oxygen is present in an amount of up to about 22% of the atmosphere. In one embodiment, the oxygen is present in an amount of from about 1% to about 10% of the atmosphere. In one embodiment, the oxygen is present in an amount of from about 2% to about 6% of the atmosphere. In one embodiment, the oxygen is present in an amount of about 4% of the atmosphere. In one embodiment, the Cu(I) salt is CuCl. In one embodiment, the Cu(I) salt is CuBr. In one embodiment, the Cu(I) salt is CuI. In one embodiment, the reaction occurs in a solvent of 2-MeTHF. In one embodiment, the reaction occurs in a solvent of THF, DCM, MTBE, 1,4-dioxane, or $Et_2O$.

In one embodiment, step (c) occurs via hydrogenation in the presence of Pd/C. In one embodiment, the hydrogenation occurs in the presence of a Palladium, Platinum, Rhodium, or Ruthenium catalyst on different supports that include carbons, alumina, alkaline earth carbonates, clays, ceramics, and celite. In one embodiment, the hydrogenation occurs in a solvent of MeOH. In one embodiment, the hydrogenation occurs in a solvent of ethanol, isopropanol, 1-propanol, butanol, THF, 2-MeTHF, MTBE, isopropyl acetate, ethyl acetate, DMF, DMAc, or NMP. In one embodiment, the hydrogenation occurs under a transfer hydrogenation condition. In one embodiment, the transfer hydrogenation condition includes cyclohexene, cyclohexadiene, formic acid, or ammonium formate.

In one embodiment, provided herein is a process for preparing a compound of Formula (I):

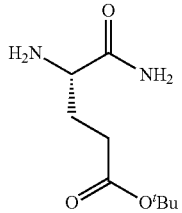
(I)

or a salt, solvate, hydrate, enantiomer, mixture of enantiomers, or isotopologue thereof, comprising
(a) contacting Compound 4 of the Formula:

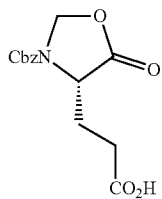
4 or a solvate, hydrate, enantiomer, mixture of enantiomers, or isotopologue thereof, with NH₃ to provide Compound 7 of the Formula:

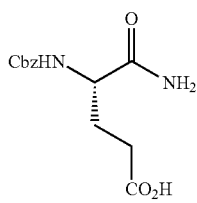
7 or a solvate, hydrate, enantiomer, mixture of enantiomers, or isotopologue thereof;
(b) transforming Compound 7, or a solvate, hydrate, enantiomer, mixture of enantiomers, or isotopologue thereof, to Compound 8 of the Formula:

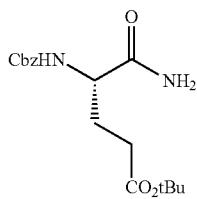
8 or a solvate, hydrate, enantiomer, mixture of enantiomers, or isotopologue thereof;
(c) deprotecting Compound 8, or a solvate, hydrate, enantiomer, mixture of enantiomers, or isotopologue thereof, to provide a compound of Formula (I), or a solvate, hydrate, enantiomer, mixture of enantiomers, or isotopologue thereof; and (d) optionally converting the compound of Formula (I), or a solvate, hydrate, enantiomer, mixture of enantiomers, or isotopologue thereof, to a HCl salt of the compound.

In one embodiment, provided herein is a process for preparing a compound of Formula (I):

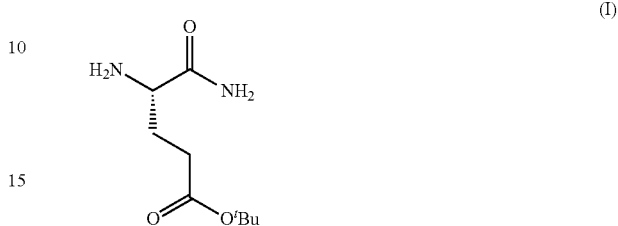
(I)

or a salt, solvate, hydrate, enantiomer, mixture of enantiomers, or isotopologue thereof, comprising
(c) deprotecting Compound 8 of the Formula:

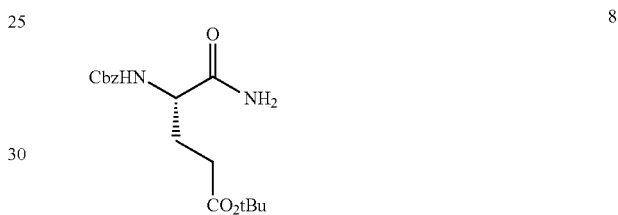
8 or a solvate, hydrate, enantiomer, mixture of enantiomers, or isotopologue thereof, to provide a compound of Formula (I), or a solvate, hydrate, enantiomer, mixture of enantiomers, or isotopologue thereof; and
(d) optionally converting the compound of Formula (I), or a solvate, hydrate, enantiomer, mixture of enantiomers, or isotopologue thereof, to a HCl salt of the compound.

In one embodiment, Compound 8, or a solvate, hydrate, enantiomer, mixture of enantiomers, or isotopologue thereof, is prepared by a process comprising
(b) transforming Compound 7 of the Formula:

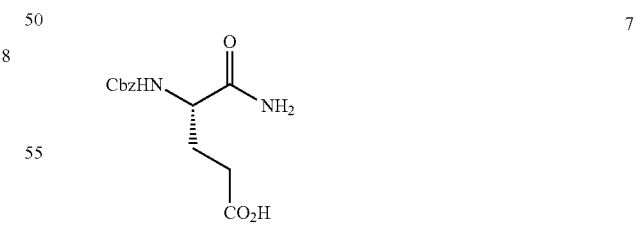
7 or a solvate, hydrate, enantiomer, mixture of enantiomers, or isotopologue thereof, to Compound 8, or a solvate, hydrate, enantiomer, mixture of enantiomers, or isotopologue thereof.

In one embodiment, Compound 7, or a solvate, hydrate, enantiomer, mixture of enantiomers, or isotopologue thereof, is prepared by a process comprising (a) contacting Compound 4 of the Formula:

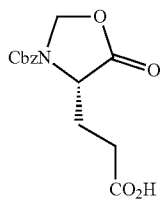

4 or a solvate, hydrate, enantiomer, mixture of enantiomers, or isotopologue thereof, with NH₃ to provide Compound 7 of the Formula:

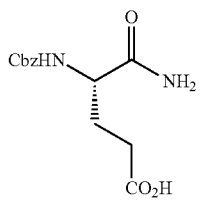

7 or a solvate, hydrate, enantiomer, mixture of enantiomers, or isotopologue thereof.

In one embodiment, NH₃ in step (a) is provided in the form of NH₄OH. In one embodiment, step (a) occurs in a solvent of MeOH.

In one embodiment, step (b) comprises reacting Compound 7, or a solvate, hydrate, enantiomer, mixture of enantiomers, or isotopologue thereof, with t-butyl 2,2,2-trichloroacetimidate. In one embodiment, the reaction occurs in the presence of BF₃ etherate. In one embodiment, the reaction occurs in a solvent of DCM.

In one embodiment, step (b) comprises reacting Compound 7, or a solvate, hydrate, enantiomer, mixture of enantiomers, or isotopologue thereof, with O-t-Bu-DIC isourea. In one embodiment, the O-t-Bu-DIC isourea is formed by reacting diisopropylcarbodiimide (DIC) with t-butanol and a Cu(I) salt. In one embodiment, the O-t-Bu-DIC isourea is formed by reacting diisopropylcarbodiimide (DIC) with t-butanol and a Cu(I) salt in the presence of oxygen. In one embodiment, the oxygen is present in an amount of up to about 22% of the atmosphere. In one embodiment, the oxygen is present in an amount of from about 1% to about 10% of the atmosphere. In one embodiment, the oxygen is present in an amount of from about 2% to about 6% of the atmosphere. In one embodiment, the oxygen is present in an amount of about 4% of the atmosphere. In one embodiment, the Cu(I) salt is CuCl. In one embodiment, the Cu(I) salt is CuBr. In one embodiment, the Cu(I) salt is CuI. In one embodiment, the reaction occurs in a solvent of 2-MeTHF. In one embodiment, the reaction occurs in a solvent of THF, DCM, MTBE, 1,4-dioxane, or Et₂O.

In one embodiment, step (c) occurs via hydrogenation in the presence of Pd/C. In one embodiment, the hydrogenation occurs in the presence of a Palladium, Platinum, Rhodium, or Ruthenium catalyst on different supports that include carbons, alumina, alkaline earth carbonates, clays, ceramics, and celite. In one embodiment, the hydrogenation occurs in a solvent of MeOH. In one embodiment, the hydrogenation occurs in a solvent of ethanol, isopropanol, 1-propanol, butanol, THF, 2-MeTHF, MTBE, isopropyl acetate, ethyl acetate, DMF, DMAc, or NMP. In one embodiment, the hydrogenation occurs under a transfer hydrogenation condition. In one embodiment, the transfer hydrogenation condition includes cyclohexene, cyclohexadiene, formic acid, or ammonium formate.

In one embodiment, Compound 4, or a solvate, hydrate, enantiomer, mixture of enantiomers, or isotopologue thereof, is prepared by a process comprising Compound 3 of the Formula:

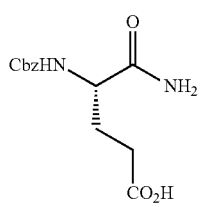

3 or a solvate, hydrate, enantiomer, mixture of enantiomers, or isotopologue thereof, with a formaldehyde source. In one embodiment, the formaldehyde source is paraformaldehyde. In one embodiment, the formaldehyde source is 1,3,5-trioxane. In one embodiment, the reaction occurs in the presence of an acid. In one embodiment, the acid is p-TsOH. In one embodiment, the acid is MsOH. In one embodiment, the acid is benzenesulfonic acid. In one embodiment, the acid is trifluoromethanesulfonic acid. In one embodiment, the acid is trifluoroacetic acid. In one embodiment, the acid is sulfuric acid. In one embodiment, the acid is trichloroacetic acid. In one embodiment, the acid is present in a catalytic amount. In one embodiment, the reaction occurs in a solvent of PhMe. In one embodiment, the reaction occurs in a solvent of acetonitrile.

In one embodiment, Compound 3, or a solvate, hydrate, enantiomer, mixture of enantiomers, or isotopologue thereof, is prepared by a process comprising protecting Compound 2 of the Formula:

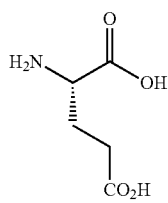

2 or a solvate, hydrate, enantiomer, mixture of enantiomers, or isotopologue thereof, with CbzCl. In one embodiment, the reaction occurs in the presence of an base. In one embodiment, the base is NaOH.

5.2.2 Process 2 for the Preparation of a Compound of Formula (I)

In one embodiment, provided herein are processes for the preparation of a compound of Formula (I), or a solvate, hydrate, enantiomer, mixture of enantiomers, or isotopologue thereof, comprising a ring-opening reaction of an oxazolidine-2,5-dione moiety with ammonia. The processes comprise an optional step of preparing a salt of the compound.

In one embodiment, provided herein is a process for preparing a compound of Formula (I):

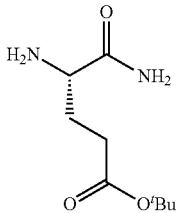

(I)

or a salt, solvate, hydrate, enantiomer, mixture of enantiomers, or isotopologue thereof, comprising
(a) contacting a compound of Formula (V):

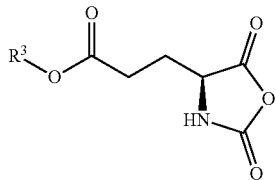

(V)

or a solvate, hydrate, enantiomer, mixture of enantiomers, or isotopologue thereof, wherein $R^3$ is a $C_{1-10}$ alkyl, with $NH_3$ to provide a compound of Formula (VI):

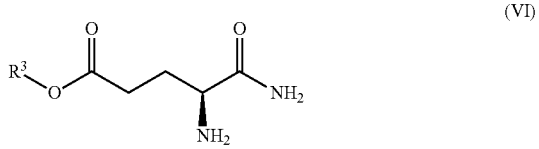

(VI)

or a solvate, hydrate, enantiomer, mixture of enantiomers, or isotopologue thereof;
(b) when $R^3$ is not tert-butyl, transforming the $R^3$ group to tert-butyl to provide a compound of Formula (I), or a solvate, hydrate, enantiomer, mixture of enantiomers, or isotopologue thereof, and
(c) optionally converting the compound of Formula (I), or a solvate, hydrate, enantiomer, mixture of enantiomers, or isotopologue thereof, to a salt of the compound.

In one embodiment, the $NH_3$ in step (a) is provided in the form of gaseous ammonia. In one embodiment, the $NH_3$ in step (a) is provided in the form of an ammonia solution. In one embodiment, the ammonia solution is an ammonia solution in water (e.g., $NH_4OH$). In one embodiment, the ammonia solution is an ammonia solution in an alcohol. In one embodiment, the alcohol is methanol, ethanol, n-propanol, or isopropanol, or a mixture thereof. In one embodiment, the ammonia solution is an ammonia solution in MeOH.

In one embodiment, the $NH_3$ in step (a) is provided in the form of ammonium salt. In one embodiment, the ammonium salt is $(NH_4)_2CO_3$, $NH_4HCO_3$, $NH_4OAc$, $NH_4H_2PO_4$, $(NH_4)_2HPO_4$, or $(NH_4)_3PO_4$. In one embodiment, the $NH_3$ in step (a) is provided in the form of $NH_4HCO_3$.

In one embodiment, $R^3$ is a $C_{1-5}$ alkyl. In one embodiment, $R^3$ is tert-butyl. In one embodiment, $R^3$ is methyl, ethyl, n-propyl, or isopropyl. In one embodiment, $R^3$ is methyl.

In one embodiment, step (b) comprises contacting the compound of Formula (VI), or a solvate, hydrate, enantiomer, mixture of enantiomers, or isotopologue thereof, with t-BuOH, optionally in the presence of a tert-butoxide salt. In one embodiment, the tert-butoxide salt in step (b) is LiO$^t$Bu, NaO$^t$Bu, or KO$^t$Bu. In one embodiment, the tert-butoxide salt in step (b) is KO$^t$Bu.

In one embodiment, the compound of Formula (V), or a solvate, hydrate, enantiomer, mixture of enantiomers, or isotopologue thereof, is prepared by a process comprising contacting a compound of Formula (VII):

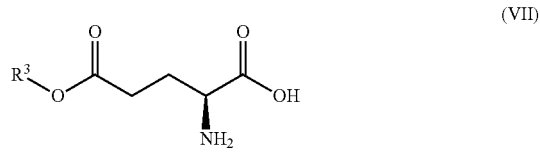

(VII)

or a solvate, hydrate, enantiomer, mixture of enantiomers, or isotopologue thereof, with a cyclization reagent.

In one embodiment, the cyclization reagent is thionyl chloride, sulfuryl chloride, 4-dimethylaminopyridine, phosgene, diphosgene, triphosgene, oxalyl chloride, a carbodiimide, an anhydride or a mixed anhydride. In one embodiment, the cyclization reagent is benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4(3H)-one (DEPBT), 1-ethyl-3-(3-dimethyllaminopropyl)carbodiimide (EDCI), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2,3-benzotriazine-3-yl)-N,N,N,N-tetramethyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt). In one embodiment, the cyclization reagent is triphosgene. In one embodiment, the cyclization reagent is N,N'-carbonyldiimidazole (CDI).

Step (c) comprises optionally converting the compound of Formula (I), or a solvate, hydrate, enantiomer, mixture of enantiomers, or isotopologue thereof, to a salt of the compound. In one embodiment, the salt is a HCl, HBr, HOAc, or PhSO$_3$H salt. In one embodiment, the salt is a HCl salt. Methods for salt formation that are generally known to those of ordinary skill in the art can be used in step (c).

In one embodiment, provided herein is a process for preparing a compound of Formula (I):

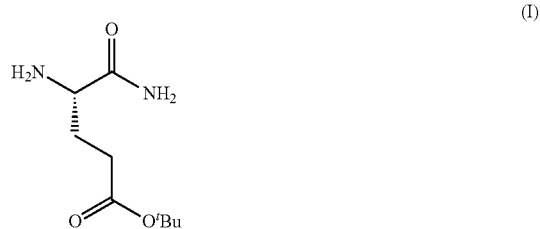 [SMILES: CC(C)(C)OC(=O)CC[C@H](N)C(N)=O]

(I)

or a salt, solvate, hydrate, enantiomer, mixture of enantiomers, or isotopologue thereof, comprising (a) contacting Compound 9 of the Formula:

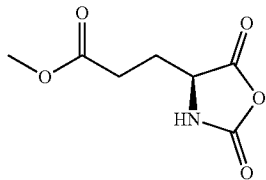

9 or a solvate, hydrate, enantiomer, mixture of enantiomers, or isotopologue thereof, with $NH_3$ to provide Compound 10 of the Formula:

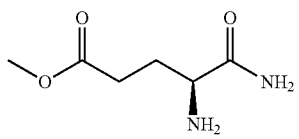

10 or a solvate, hydrate, enantiomer, mixture of enantiomers, or isotopologue thereof;

(b) transforming Compound 10, or a solvate, hydrate, enantiomer, mixture of enantiomers, or isotopologue thereof, to a compound of Formula (I), or a solvate, hydrate, enantiomer, mixture of enantiomers, or isotopologue thereof, and (c) optionally converting the compound of Formula (I), or a solvate, hydrate, enantiomer, mixture of enantiomers, or isotopologue thereof, to a HCl salt of the compound.

In one embodiment, provided herein is a process for preparing a compound of Formula (I):

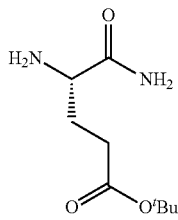

(I)

or a salt, solvate, hydrate, enantiomer, mixture of enantiomers, or isotopologue thereof, comprising (b) transforming Compound 10 of the Formula:

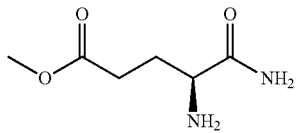

10 or a solvate, hydrate, enantiomer, mixture of enantiomers, or isotopologue thereof, to a compound of Formula (I), or a solvate, hydrate, enantiomer, mixture of enantiomers, or isotopologue thereof, and (c) optionally converting the compound of Formula (I), or a solvate, hydrate, enantiomer, mixture of enantiomers, or isotopologue thereof, to a HCl salt of the compound.

In one embodiment, Compound 10, or a solvate, hydrate, enantiomer, mixture of enantiomers, or isotopologue thereof, is prepared by a process comprising (a) contacting Compound 9 of the Formula:

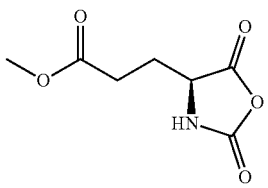

9 or a solvate, hydrate, enantiomer, mixture of enantiomers, or isotopologue thereof, with $NH_3$ to provide Compound 10, or a solvate, hydrate, enantiomer, mixture of enantiomers, or isotopologue thereof.

In one embodiment, $NH_3$ in step (a) is provided in the form of $NH_4OH$. In one embodiment, step (a) occurs in a solvent of MeOH.

In one embodiment, step (b) comprises contacting the compound of Formula (VI), or a solvate, hydrate, enantiomer, mixture of enantiomers, or isotopologue thereof, with t-BuOH, in the presence of $KO^tBu$.

In one embodiment, Compound 9, or a solvate, hydrate, enantiomer, mixture of enantiomers, or isotopologue thereof, is prepared by a process comprising contacting an amino acid compound of the Formula:

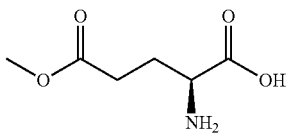

or a solvate, hydrate, enantiomer, mixture of enantiomers, or isotopologue thereof, with a cyclization reagent. In one embodiment, the cyclization reagent is triphosgene. In one embodiment, the cyclization reagent is N,N'-carbonyldiimidazole (CDI).

In one embodiment, the amino acid compound, or a solvate, hydrate, enantiomer, mixture of enantiomers, or isotopologue thereof, is prepared by a process comprising transforming Compound 2 of the Formula:

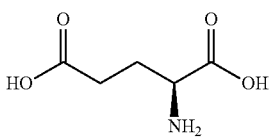

2 or a solvate, hydrate, enantiomer, mixture of enantiomers, or isotopologue thereof, to the amino acid compound, or a solvate, hydrate, enantiomer, mixture of enantiomers, or isotopologue thereof, under a condition suitable for ester formation. In one embodiment, the condition is reacting with MeOH in the presence of an acid. In one embodiment, the acid is HCl.

In one embodiment, provided herein is a process for preparing a compound of Formula (I):

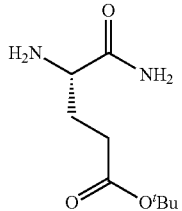

(I)

or a salt, solvate, hydrate, enantiomer, mixture of enantiomers, or isotopologue thereof, comprising (a) contacting Compound 12 of the Formula:

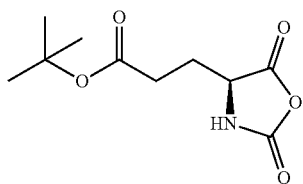

12 or a solvate, hydrate, enantiomer, mixture of enantiomers, or isotopologue thereof, with NH$_3$ to provide a compound of Formula (I), or a solvate, hydrate, enantiomer, mixture of enantiomers, or isotopologue thereof; and (c) optionally converting the compound of Formula (I), or a solvate, hydrate, enantiomer, mixture of enantiomers, or isotopologue thereof, to a HCl salt of the compound.

In one embodiment, the NH$_3$ in step (a) is provided in the form of NH$_4$HCO$_3$.

In one embodiment, Compound 12, or a solvate, hydrate, enantiomer, mixture of enantiomers, or isotopologue thereof, is prepared by a process comprising contacting Compound 11 of the Formula:

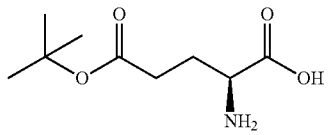

11 or a solvate, hydrate, enantiomer, mixture of enantiomers, or isotopologue thereof, with a cyclization reagent. In one embodiment, the cyclization reagent is triphosgene. In one embodiment, the cyclization reagent is N,N'-carbonyldiimidazole (CDI).

In one embodiment, Compound 11, or a solvate, hydrate, enantiomer, mixture of enantiomers, or isotopologue thereof, is prepared by a process comprising transforming Compound 2 of the Formula:

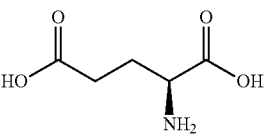

2 or a solvate, hydrate, enantiomer, mixture of enantiomers, or isotopologue thereof, to Compound 11, or a solvate, hydrate, enantiomer, mixture of enantiomers, or isotopologue thereof, under a condition suitable for ester formation. In one embodiment, the condition is reacting with isobutylene in the presence of BF$_3$·Et$_2$O.

5.2.3 Process 3 for the Preparation of a Compound of Formula (I)

In one embodiment, provided herein are processes for the preparation of a compound of Formula (I), or a solvate, hydrate, enantiomer, mixture of enantiomers, or isotopologue thereof, comprising a ring-opening reaction of a N-protected pyrrolidin-2-one moiety with a tert-butoxide nucleophile. The processes comprise an optional step of preparing a salt of the compound.

In one embodiment, provided herein is a process for preparing a compound of Formula (I):

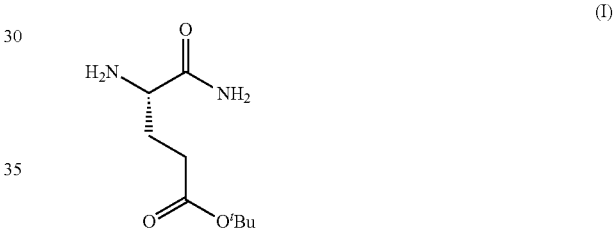

(I)

or a salt, solvate, hydrate, enantiomer, mixture of enantiomers, or isotopologue thereof, comprising (a) contacting a compound of Formula (VIII):

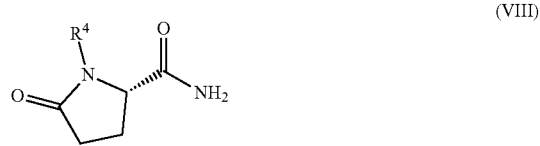

(VIII)

or a solvate, hydrate, enantiomer, mixture of enantiomers, or isotopologue thereof, wherein R$^4$ is a suitable amino protecting group, with a t-butoxide nucleophile to provide a compound of Formula (IX):

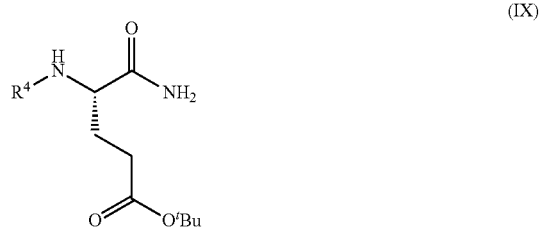

(IX)

or a solvate, hydrate, enantiomer, mixture of enantiomers, or isotopologue thereof;

(b) deprotecting the —NH—$R^4$ group to provide a compound of Formula (I), or a solvate, hydrate, enantiomer, mixture of enantiomers, or isotopologue thereof; and (c) optionally converting the compound of Formula (I), or a solvate, hydrate, enantiomer, mixture of enantiomers, or isotopologue thereof, to a salt of the compound.

In one embodiment, provided herein is a process for preparing a compound of Formula (I):

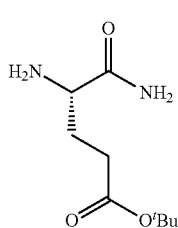
(I)

or a salt, solvate, hydrate, enantiomer, mixture of enantiomers, or isotopologue thereof, comprising (b) deprotecting the —NH—$R^4$ group in a compound of Formula (IX):

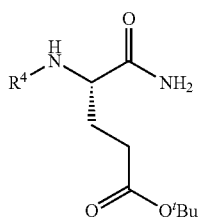
(IX)

or a solvate, hydrate, enantiomer, mixture of enantiomers, or isotopologue thereof, wherein $R^4$ is a suitable amino protecting group, to provide a compound of Formula (I), or a solvate, hydrate, enantiomer, mixture of enantiomers, or isotopologue thereof; and (c) optionally converting the compound of Formula (I), or a solvate, hydrate, enantiomer, mixture of enantiomers, or isotopologue thereof, to a salt of the compound.

In one embodiment, the compound of Formula (IX), or a solvate, hydrate, enantiomer, mixture of enantiomers, or isotopologue thereof, is prepared by a process comprising (a) contacting a compound of Formula (VIII):

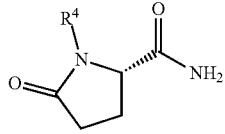
(VIII)

or a solvate, hydrate, enantiomer, mixture of enantiomers, or isotopologue thereof, with a t-butoxide nucleophile to provide a compound of Formula (IX), or a solvate, hydrate, enantiomer, mixture of enantiomers, or isotopologue thereof.

In one embodiment, $R^4$ is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (Pf), bis(trimethylsilyl)methyl, t-butoxycarbonyl (Boc), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, $R^4$ is benzyl (Bn), 4-methoxybenzyl (PMB), 3,4-dimethoxybenzyl (DMPM), benzyloxycarbonyl (Cbz), p-methoxybenzyloxycarbonyl (Moz), or t-butoxycarbonyl (Boc). In one embodiment, $R^4$ is benzyloxycarbonyl (Cbz). In one embodiment, $R^4$ is Boc.

Depending on $R^4$, deprotecting conditions generally known to those of ordinary skill in the art can be used in step (b). In one embodiment, step (b) occurs under a hydrogenation condition. In one embodiment, the hydrogenation occurs in the presence of a Pd catalyst. In one embodiment, the Pd catalyst is Pd/C. In one embodiment, the hydrogenation occurs in the presence of a Palladium, Platinum, Rhodium, or Ruthenium catalyst on different supports that include carbons, alumina, alkaline earth carbonates, clays, ceramics, and celite. In one embodiment, the hydrogenation occurs in a solvent of MeOH. In one embodiment, the hydrogenation occurs in a solvent of ethanol, isopropanol, 1-propanol, butanol, THF, 2-MeTHF, MTBE, isopropyl acetate, ethyl acetate, DMF, DMAc, or NMP. In one embodiment, the hydrogenation occurs under a transfer hydrogenation condition. In one embodiment, the transfer hydrogenation condition includes cyclohexene, cyclohexadiene, formic acid, or ammonium formate.

In one embodiment, the tert-butoxide nucleophile in step (a) is LiO$^t$Bu, NaO$^t$Bu, or KO$^t$Bu. In one embodiment, the tert-butoxide nucleophile in step (a) is KO$^t$Bu.

In one embodiment, the compound of Formula (VIII), or a solvate, hydrate, enantiomer, mixture of enantiomers, or isotopologue thereof, is prepared by a process comprising protecting Compound 14 of the Formula:

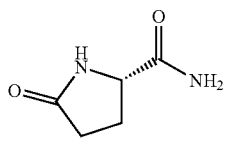
14 or a solvate, hydrate, enantiomer, mixture of enantiomers, or isotopologue thereof, to provide the compound of Formula (VIII), or a solvate, hydrate, enantiomer, mixture of enantiomers, or isotopologue thereof.

Step (c) comprises optionally converting the compound of Formula (I), or a solvate, hydrate, enantiomer, mixture of enantiomers, or isotopologue thereof, to a salt of the compound. In one embodiment, the salt is a HCl, HBr, HOAc, or PhSO$_3$H salt. In one embodiment, the salt is a HCl salt. Methods for salt formation that are generally known to those of ordinary skill in the art can be used in step (c).

In one embodiment, Compound 14, or a solvate, hydrate, enantiomer, mixture of enantiomers, or isotopologue thereof, is prepared by a process comprising transforming Compound 13 of the Formula:

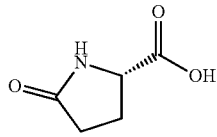

13 or a solvate, hydrate, enantiomer, mixture of enantiomers, or isotopologue thereof, to Compound 14, or a solvate, hydrate, enantiomer, mixture of enantiomers, or isotopologue thereof, under a condition suitable for amide formation. In one embodiment, the condition is reacting with isobutyl-chloroformate or other chloroformate derivative, followed by ammonia.

5.2.4 Process 4 for the Preparation of a Compound of Formula (I)

In one embodiment, provided herein are processes for the preparation of a compound of Formula (I), or a solvate, hydrate, enantiomer, mixture of enantiomers, or isotopologue thereof, comprising a Michael addition reaction of 2-((diphenylmethylene)amino)acetonitrile, 2-((diphenylmethylene)amino)acetamide, or 2-((diphenylmethylene)amino)acetate ester to tert-butyl acrylate. The processes comprise an optional step of chiral separation. The processes also comprise an optional step of preparing a salt of the compound.

In one embodiment, provided herein is a process for preparing a compound of Formula (I-rac):

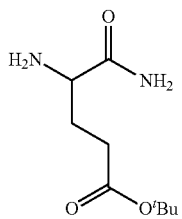

(I-rac)

or a salt, solvate, hydrate, enantiomer, or isotopologue thereof, comprising (a) contacting a compound of Formula (XI):

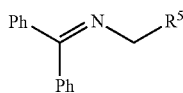

(XI)

or a solvate, hydrate, or isotopologue thereof, wherein $R^5$ is —$CONH_2$, —CN, or —$CO_2R^6$, and $R^6$ is a $C_{1-10}$ alkyl, with tert-butyl acrylate in the presence of a base to provide a compound of Formula (XII):

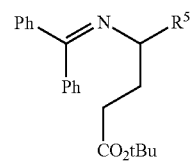

(XII)

or a solvate, hydrate, or isotopologue thereof;

(b) transforming the compound of Formula (XII), or a solvate, hydrate, or isotopologue thereof, to a compound of Formula (XIII):

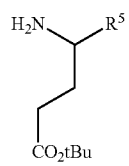

(XIII)

or a solvate, hydrate, or isotopologue thereof, in the presence of an acid;

(c) when $R^5$ is not —$CONH_2$, transforming the $R^5$ group to —$CONH_2$ to provide a compound of Formula (I-rac), or a solvate, hydrate, or isotopologue thereof, wherein the —$NH_2$ group in the compound of Formula (XIII), or a solvate, hydrate, or isotopologue thereof, is optionally protected and deprotected in step (c);

(d) optionally separating the compound of Formula (I-rac), or a solvate, hydrate, or isotopologue thereof, to provide a compound of Formula (I):

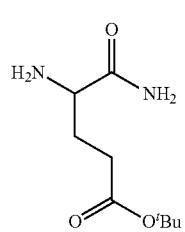

(I)

or a solvate, hydrate, or isotopologue thereof, via a chiral separation condition; and (e) optionally converting the compound of Formula (I), or a solvate, hydrate, or isotopologue thereof, to a salt of the compound.

In one embodiment, provided herein is a process for preparing a compound of Formula (I-rac):

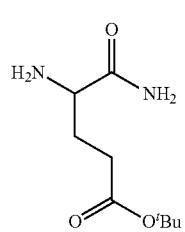

(I-rac)

or a salt, solvate, hydrate, enantiomer, or isotopologue thereof, comprising (b) transforming a compound of Formula (XII):

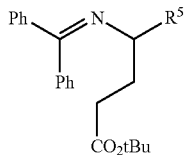

(XII)

or a solvate, hydrate, or isotopologue thereof, wherein $R^5$ is —$CONH_2$, —CN, or —$CO_2R^6$, and $R^6$ is a $C_{1-10}$ alkyl, to a compound of Formula (XIII):

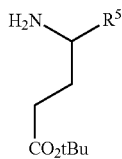

(XIII)

or a solvate, hydrate, or isotopologue thereof, in the presence of an acid;

(c) when $R^5$ is not —$CONH_2$, transforming the $R^5$ group to —$CONH_2$ to provide a compound of Formula (I-rac), or a solvate, hydrate, or isotopologue thereof, wherein the —$NH_2$ group in the compound of Formula (XIII), or a solvate, hydrate, or isotopologue thereof, is optionally protected and deprotected in step (c);

(d) optionally separating the compound of Formula (I-rac), or a solvate, hydrate, or isotopologue thereof, to provide a compound of Formula (I):

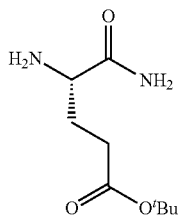

(I)

or a solvate, hydrate, or isotopologue thereof, via a chiral separation condition; and (e) optionally converting the compound of Formula (I), or a solvate, hydrate, or isotopologue thereof, to a salt of the compound.

In one embodiment, the compound of Formula (XII), or a solvate, hydrate, or isotopologue thereof, is prepared by a process comprising (a) contacting a compound of Formula (XI):

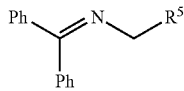

(XI)

or a solvate, hydrate, or isotopologue thereof, with tert-butyl acrylate in the presence of a base to provide a compound of Formula (XII), or a solvate, hydrate, or isotopologue thereof.

In one embodiment, $R^5$ is —$CONH_2$. In one embodiment, $R^5$ is —CN. In one embodiment, $R^5$ is —$CO_2R^6$, and $R^6$ is a $C_{1-10}$ alkyl. In one embodiment, $R^5$ is —$CO_2R^6$, and $R^6$ is a $C_{1-5}$ alkyl. In one embodiment, $R^6$ is methyl, ethyl, n-propyl, or isopropyl. In one embodiment, $R^5$ is —$CO_2Me$. In one embodiment, $R^5$ is —$CO_2Et$.

In one embodiment, when $R^5$ is not —$CONH_2$, step (c) comprises (c1) protecting the —$NH_2$ group with a protecting group, (c2) transforming the $R^5$ group to —$CONH_2$; and (c3) deprotecting the protecting group of the —$NH_2$ group.

In one embodiment, the $R^5$ group is transformed to —$CONH_2$ directly. In one embodiment, the $R^5$ group is transformed to a —COOH group, and then the —COOH group is transformed to —$CONH_2$.

In one embodiment, the protecting group for the —$NH_2$ group in step (c1) is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (N), bis(trimethylsilyl)methyl, t-butoxycarbonyl (Boc), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, the protecting group is benzyl (Bn), 4-methoxybenzyl (PMB), 3,4-dimethoxybenzyl (DMPM), benzyloxycarbonyl (Cbz), or p-methoxybenzyloxycarbonyl (Moz). In one embodiment, the protecting group is benzyl. In one embodiment, the protecting group is Cbz.

In one embodiment, the deprotectoin in step (c3) occurs under a hydrogenation condition. Depending on the protecting group, other deprotecting conditions generally known to those of ordinary skill in the art can be used in step (c3).

In one embodiment, the base in step (a) is sodium $C_{1-14}$ alkoxide, potassium $C_{1-14}$ alkoxide, sodium hydride, potassium hydride, calcium hydride, cesium carbonate, lithium hexamethyldisilazide (LiHMDS), lithium diisopropylamide (LDA), 2-tert-butyl-1,1,3,3-tetramethyl-guanidine (Barton's Base), 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-diisopropylethylamine (DIPEA or Hünig's base), pyridine, 2,6-di-tert-butyl-pyridine, 2,6-lutidine, lithium tetramethylpiperidide (LiTMP or harpoon base), 7-methyl-1,5,7 triazabicyclo[4.4.0]dec-5-ene (MTBD), 1,2,2,6,6-pentamethylpiperidine (PMP), 2,2,6,6-tetramethylpiperidine (TMP), tributylamine, 2,4,6-tri-tert-butylpyridine, tris(trimethylsilyl)amine, n-butyllithium, sec-butyllithium, tert-butyllithium, potassium bis(trimethylsilyl)amide, sodium tert-butoxide, tert-butylimino-tris(dimethylamino)phosphorane, or 2-tert-butylimino-2-diethylamino-1,3-dimethylperhydro-1,3,2-diazaphosphorine. In one embodiment, the base in step (a) is triethylamine, diisopropylethylamine, pyridine, 4-dimethylaminopyridine, or 1,8-diazabicyclo[5.4.0]undec-7-ene (DBU). In one embodiment, the base in step (a) is DBU. In one embodiment, the base in step (a) is $Cs_2CO_3$.

In one embodiment, the acid in step (b) is formic acid, acetic acid, trifluoroacetic acid, benzoic acid, citric acid, sulfonic acid, benzenesulfonic acid, p-toluenesulfonic acid, camphorsulfonic acid, methanesulfonic acid, trifluoromethanesulfonic acid, hydrochloric acid, sulfuric acid, nitric acid, or phosphoric acid. In one embodiment, the acid in step (b) is HCl, citric acid, or p-toluenesulfonic acid.

In one embodiment, step (d) comprises contacting the compound of Formula (I-rac), or a solvate, hydrate, or isotopologue thereof, with a chiral acid to provide a diastereomeric mixture of salts, and separating the resulted diastereomeric mixture of salts by selective crystallization. In one embodiment, the chiral acid is tartaric acid, 2,3-dibenzoyl tartaric acid, mandelic acid, camphorsulfonic acid, N-Ac-N-leucine, or N-Ac-L-phenylalanine. In one embodiment, the selective crystallization occurs in a solvent selected from MeOH, isopropanol, and n-propanol, or a mixture thereof. Others methods for chiral separation that are generally known to those of ordinary skill in the art can be used in step (d).

Step (e) comprises optionally converting the compound of Formula (I), or a solvate, hydrate, enantiomer, mixture of enantiomers, or isotopologue thereof, to a salt of the compound. In one embodiment, the salt is a HCl, HBr, HOAc, or PhSO$_3$H salt. In one embodiment, the salt is a HCl salt. Methods for salt formation that are generally known to those of ordinary skill in the art can be used in step (e).

In one embodiment, provided herein is a process for preparing a compound of Formula (I-rac):

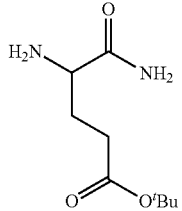

(I-rac)

or a salt, solvate, hydrate, enantiomer, or isotopologue thereof, comprising
(a) contacting Compound 15 of the Formula:

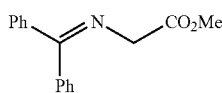

15 or a solvate, hydrate, or isotopologue thereof, with tert-butyl acrylate in the presence of a base to provide Compound 17 of the Formula:

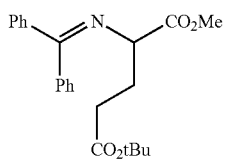

17 or a solvate, hydrate, or isotopologue thereof;

(b) transforming Compound 17, or a solvate, hydrate, or isotopologue thereof, to Compound 18 of the Formula:

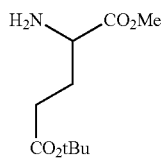

18 or a solvate, hydrate, or isotopologue thereof, in the presence of an acid;

(c1) protecting the —NH$_2$ group to provide Compound 19 of the Formula:

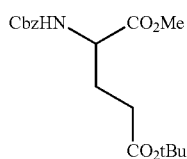

19 or a solvate, hydrate, or isotopologue thereof;

(c2) transforming the —CO$_2$Me group to —CONH$_2$ to provide Compound rac-8 of the Formula:

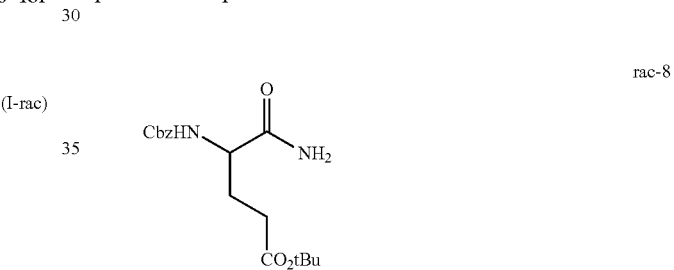

rac-8 or a solvate, hydrate, or isotopologue thereof;

(c3) deprotecting the protecting group of the —NH$_2$ group to provide a compound of Formula (I-rac), or a solvate, hydrate, or isotopologue thereof;

(d) optionally separating the compound of Formula (I-rac), or a solvate, hydrate, or isotopologue thereof, to provide a compound of Formula (I):

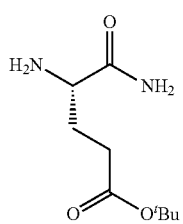

(I)

or a solvate, hydrate, or isotopologue thereof, via a chiral separation condition; and (e) optionally converting the compound of Formula (I), or a solvate, hydrate, or isotopologue thereof, to a HCl salt of the compound.

In one embodiment, provided herein is a process for preparing a compound of Formula (I-rac):

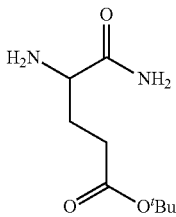

(I-rac)

or a salt, solvate, hydrate, enantiomer, or isotopologue thereof, comprising (c3) deprotecting the protecting group of the —NH$_2$ group in Compound rac-8 of the Formula:

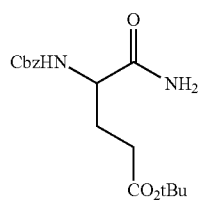

rac-8 or a solvate, hydrate, or isotopologue thereof, to provide a compound of Formula (I-rac), or a solvate, hydrate, or isotopologue thereof;

(d) optionally separating the compound of Formula (I-rac), or a solvate, hydrate, or isotopologue thereof, to provide a compound of Formula (I):

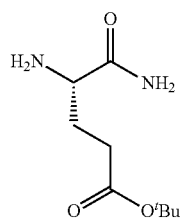

(I)

or a solvate, hydrate, or isotopologue thereof, via a chiral separation condition; and (e) optionally converting the compound of Formula (I), or a solvate, hydrate, or isotopologue thereof, to a HCl salt of the compound.

In one embodiment, Compound rac-8, or a solvate, hydrate, or isotopologue thereof, is prepared by a process comprising (c2) transforming the —CO$_2$Me group in Compound 19 of the Formula:

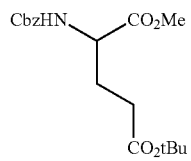

19 or a solvate, hydrate, or isotopologue thereof, to —CONH$_2$ to provide Compound rac-8, or a solvate, hydrate, or isotopologue thereof.

In one embodiment, Compound 19, or a solvate, hydrate, or isotopologue thereof, is prepared by a process comprising (c1) protecting the —NH$_2$ group in Compound 18 of the Formula:

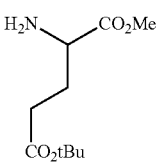

18 or a solvate, hydrate, or isotopologue thereof, to provide Compound 19, or a solvate, hydrate, or isotopologue thereof.

In one embodiment, Compound 18, or a solvate, hydrate, or isotopologue thereof, is prepared by a process comprising (b) transforming Compound 17 of the Formula:

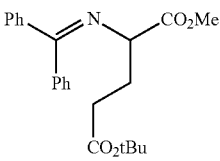

17 or a solvate, hydrate, or isotopologue thereof, to Compound 18, or a solvate, hydrate, or isotopologue thereof, in the presence of an acid.

In one embodiment, Compound 17, or a solvate, hydrate, or isotopologue thereof, is prepared by a process comprising (a) contacting Compound 15 of the Formula:

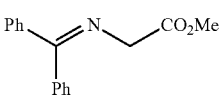

15 or a solvate, hydrate, or isotopologue thereof, with tert-butyl acrylate in the presence of a base to provide Compound 17, or a solvate, hydrate, or isotopologue thereof;

In one embodiment, the base in step (a) is DBU. In one embodiment, step (a) occurs in a solvent of MeCN. In one embodiment, Compound 17, or a solvate, hydrate, or isotopologue thereof, is not isolated after step (a).

In one embodiment, the acid in step (b) is HCl. In one embodiment, step (b) occurs in a solvent of 2-MeTHF. In one embodiment, Compound 18, or a solvate, hydrate, or isotopologue thereof, is not isolated after step (b).

In one embodiment, step (c1) comprises reacting Compound 18, or a solvate, hydrate, or isotopologue thereof, with CbzCl. In one embodiment, step (c1) occurs in the presence of K$_2$CO$_3$. In one embodiment, step (c1) occurs in a solvent of 2-MeTHF. In one embodiment, Compound 19, or a solvate, hydrate, or isotopologue thereof, is not isolated after step (c1).

In one embodiment, step (c2) comprises hydrolyzing Compound 19, or a solvate, hydrate, or isotopologue thereof, under a basic condition to provide Compound 20 of the Formula:

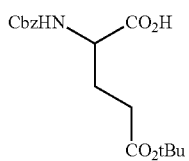

or a solvate, hydrate, or isotopologue thereof; followed by amide formation to provide Compound rac-8, or a solvate, hydrate, or isotopologue thereof.

In one embodiment, the basic condition is the presence of LiOH. In one embodiment, the basic condition is the presence potassium trimethylsiloxide (TMSOK). In one embodiment, the hydrolysis occurs in a solvent of 2-MeTHF.

In one embodiment, the amide formation comprises reacting Compound 20, or a solvate, hydrate, or isotopologue thereof, with isobutyl chloroformate, followed by $NH_3$.

In one embodiment, step (c3) occurs via hydrogenation in the presence of a Pd catalyst.

In one embodiment, provided herein is a process for preparing a compound of Formula (I-rac):

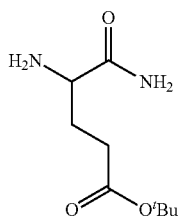

(I-rac)

or a salt, solvate, hydrate, enantiomer, or isotopologue thereof, comprising (a) contacting Compound 23 of the Formula:

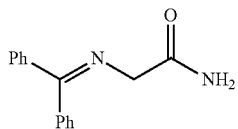

23 or a solvate, hydrate, or isotopologue thereof, with tert-butyl acrylate in the presence of a base to provide Compound 24 of the Formula:

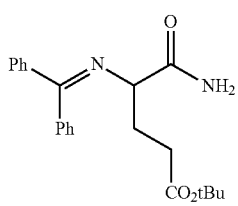

24 or a solvate, hydrate, or isotopologue thereof;

(b) transforming Compound 24, or a solvate, hydrate, or isotopologue thereof, to a compound of Formula (I-rac), or a solvate, hydrate, or isotopologue thereof, in the presence of an acid;

(d) optionally separating the compound of Formula (I-rac), or a solvate, hydrate, or isotopologue thereof, to provide a compound of Formula (I):

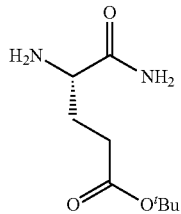

(I)

or a solvate, hydrate, or isotopologue thereof, via a chiral separation condition; and (e) optionally converting the compound of Formula (I), or a solvate, hydrate, or isotopologue thereof, to a HCl salt of the compound.

In one embodiment, provided herein is a process for preparing a compound of Formula (I-rac):

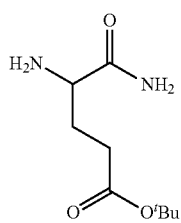

(I-rac)

or a salt, solvate, hydrate, enantiomer, or isotopologue thereof, comprising (b) transforming Compound 24 of the Formula:

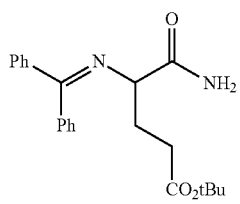

24 or a solvate, hydrate, or isotopologue thereof, to a compound of Formula (I-rac), or a solvate, hydrate, or isotopologue thereof, in the presence of an acid;

(d) optionally separating the compound of Formula (I-rac), or a solvate, hydrate, or isotopologue thereof, to provide a compound of Formula (I):

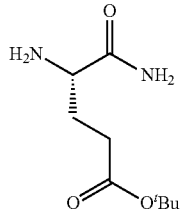

(I)

or a solvate, hydrate, or isotopologue thereof, via a chiral separation condition; and (e) optionally converting the compound of Formula (I), or a solvate, hydrate, or isotopologue thereof, to a HCl salt of the compound.

In one embodiment, Compound 24, or a solvate, hydrate, or isotopologue thereof, is prepared by a process comprising (a) contacting Compound 23 of the Formula:

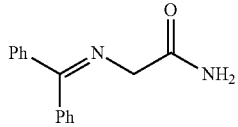

or a solvate, hydrate, or isotopologue thereof, with tert-butyl acrylate in the presence of a base to provide Compound 24, or a solvate, hydrate, or isotopologue thereof.

In one embodiment, the base in step (a) is DBU. In one embodiment, the base in step (a) is $Cs_2CO_3$. In one embodiment, step (a) occurs in a solvent of MeCN.

In one embodiment, the acid in step (b) is HCl. In one embodiment, step (b) occurs in a solvent of 2-MeTHF.

In one embodiment, Compound 23, or a solvate, hydrate, enantiomer, mixture of enantiomers, or isotopologue thereof, is prepared by a process comprising reacting Compound 21 of the Formula:

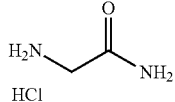

or a solvate, hydrate, or isotopologue thereof, with Compound 22 of the Formula:

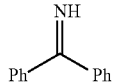

or a solvate, hydrate, or isotopologue thereof. In one embodiment, the reaction occurs in the presence of a base. In one embodiment, the base is $NEt_3$. In one embodiment, the reaction occurs in a solvent of 1,2-dichloroethane (DCE).

In one embodiment, provided herein is a process for preparing a compound of Formula (I-rac):

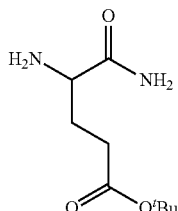

or a salt, solvate, hydrate, enantiomer, or isotopologue thereof, comprising (a) contacting Compound 25 of the Formula:

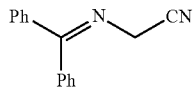

or a solvate, hydrate, or isotopologue thereof, with tert-butyl acrylate in the presence of a base to provide Compound 26 of the Formula:

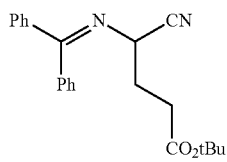

or a solvate, hydrate, or isotopologue thereof;

(b) transforming Compound 26, or a solvate, hydrate, or isotopologue thereof, to Compound 27 of the Formula:

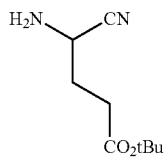

or a solvate, hydrate, or isotopologue thereof, in the presence of an acid;

(c1) protecting the —$NH_2$ group to provide Compound 28 of the Formula:

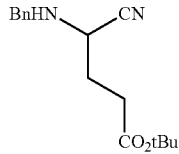

or a solvate, hydrate, or isotopologue thereof;

(c2) transforming the —CN group to —$CONH_2$ to provide Compound 29 of the Formula:

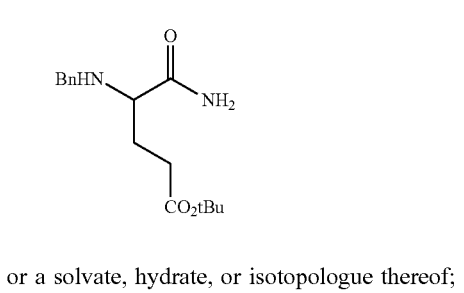

or a solvate, hydrate, or isotopologue thereof;

(c3) deprotecting the protecting group of the —NH$_2$ group to provide a compound of Formula (I-rac), or a solvate, hydrate, or isotopologue thereof;

(d) optionally separating the compound of Formula (I-rac), or a solvate, hydrate, or isotopologue thereof, to provide a compound of Formula (I):

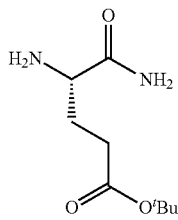

(I)

or a solvate, hydrate, or isotopologue thereof, via a chiral separation condition; and (e) optionally converting the compound of Formula (I), or a solvate, hydrate, or isotopologue thereof, to a HCl salt of the compound.

In one embodiment, provided herein is a process for preparing a compound of Formula (I-rac):

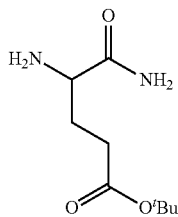

(I-rac)

or a salt, solvate, hydrate, enantiomer, or isotopologue thereof, comprising (c3) deprotecting the protecting group of the —NH$_2$ group in Compound 29 of the Formula:

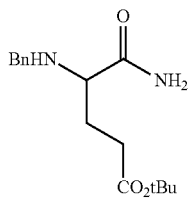

29 or a solvate, hydrate, or isotopologue thereof, to provide a compound of Formula (I-rac), or a solvate, hydrate, or isotopologue thereof;

(d) optionally separating the compound of Formula (I-rac), or a solvate, hydrate, or isotopologue thereof, to provide a compound of Formula (I):

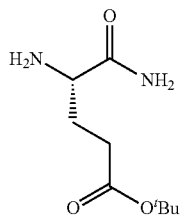

(I)

or a solvate, hydrate, or isotopologue thereof, via a chiral separation condition; and (e) optionally converting the compound of Formula (I), or a solvate, hydrate, or isotopologue thereof, to a HCl salt of the compound.

In one embodiment, Compound 29, or a solvate, hydrate, or isotopologue thereof, is prepared by a process comprising (c2) transforming the —CN group in Compound 28 of the Formula:

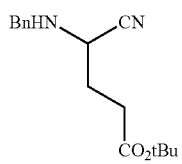

28 or a solvate, hydrate, or isotopologue thereof, to —CONH$_2$ to provide Compound 29, or a solvate, hydrate, or isotopologue thereof.

In one embodiment, Compound 28, or a solvate, hydrate, or isotopologue thereof, is prepared by a process comprising (c1) protecting the —NH$_2$ group in Compound 27 of the Formula:

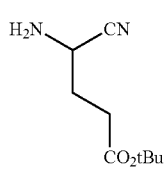

27 or a solvate, hydrate, or isotopologue thereof, to provide Compound 28, or a solvate, hydrate, or isotopologue thereof.

In one embodiment, Compound 27, or a solvate, hydrate, or isotopologue thereof, is prepared by a process comprising (b) transforming Compound 26 of the Formula:

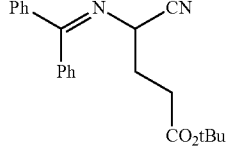

26 or a solvate, hydrate, or isotopologue thereof, to Compound 27, or a solvate, hydrate, or isotopologue thereof, in the presence of an acid.

In one embodiment, Compound 26, or a solvate, hydrate, or isotopologue thereof, is prepared by a process comprising (a) contacting Compound 25 of the Formula:

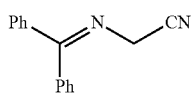
25 or a solvate, hydrate, or isotopologue thereof, with tert-butyl acrylate in the presence of a base to provide Compound 26, or a solvate, hydrate, or isotopologue thereof.

In one embodiment, the base in step (a) is DBU. In one embodiment, step (a) occurs in a solvent of MeCN.

In one embodiment, the acid in step (b) is HCl. In one embodiment, step (b) occurs in a solvent of 2-MeTHF. In one embodiment, Compound 27, or a solvate, hydrate, or isotopologue thereof, is not isolated after step (b).

In one embodiment, step (c1) comprises reacting Compound 27, or a solvate, hydrate, or isotopologue thereof, with benzaldehyde, followed by a reducing reagent. In one embodiment, the reducing reagent is sodium triacetoxyborohydride (STAB).

In one embodiment, step (c2) comprises hydrolyzing Compound 28, or a solvate, hydrate, or isotopologue thereof, in the presence of a formaldehyde catalyst and hydroxide base to provide Compound 29, or a solvate, hydrate, or isotopologue thereof. Other methods for nitrile hydrolysis that are generally known to those of ordinary skill in the art can be used in step (c2).

In one embodiment, step (c3) occurs via hydrogenation in the presence of a Pd catalyst.

5.2.5 Process 5 for the Preparation of a Compound of Formula (I)

In one embodiment, provided herein are processes for the preparation of a compound of Formula (I), or a solvate, hydrate, enantiomer, mixture of enantiomers, or isotopologue thereof, comprising a Michael addition reaction of 2-phenyloxazol-5(4H)-one to tert-butyl acrylate. The processes comprise an optional step of chiral separation. The processes also comprise an optional step of preparing a salt of the compound.

In one embodiment, provided herein is a process for preparing a compound of Formula (I-rac):

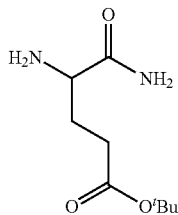
(I-rac)

or a salt, solvate, hydrate, enantiomer, or isotopologue thereof, comprising (a) contacting Compound 31 of the Formula:

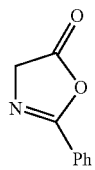
31 or a solvate, hydrate, or isotopologue thereof, with tert-butyl acrylate in the presence of a base to provide Compound 32 of the Formula:

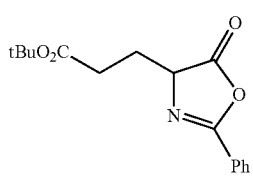
32 or a solvate, hydrate, or isotopologue thereof;

(b) contacting Compound 32, or a solvate, hydrate, or isotopologue thereof, with NH₃ to provide Compound 33 of the Formula:

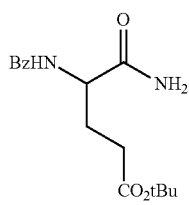
33 or a solvate, hydrate, or isotopologue thereof;

(c) deprotecting the —NHBz group to provide a compound of Formula (I-rac), or a solvate, hydrate, or isotopologue thereof;

(d) optionally separating the compound of Formula (I-rac), or a solvate, hydrate, or isotopologue thereof, to provide a compound of Formula (I):

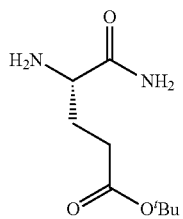
(I)

or a solvate, hydrate, or isotopologue thereof, via a chiral separation condition; and (e) optionally converting the compound of Formula (I), or a solvate, hydrate, or isotopologue thereof, to a salt of the compound.

In one embodiment, provided herein is a process for preparing a compound of Formula (I-rac):

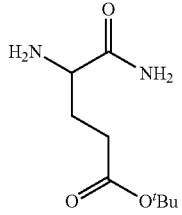

(I-rac)

or a salt, solvate, hydrate, enantiomer, or isotopologue thereof, comprising (c) deprotecting the —NHBz group in Compound 33 of the Formula:

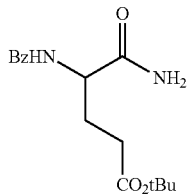

33 or a solvate, hydrate, or isotopologue thereof, to provide a compound of Formula (I-rac), or a solvate, hydrate, or isotopologue thereof;

(d) optionally separating the compound of Formula (I-rac), or a solvate, hydrate, or isotopologue thereof, to provide a compound of Formula (I):

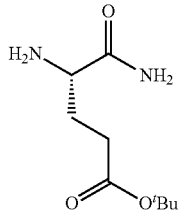

(I)

or a solvate, hydrate, or isotopologue thereof, via a chiral separation condition; and (e) optionally converting the compound of Formula (I), or a solvate, hydrate, or isotopologue thereof, to a salt of the compound.

In one embodiment, Compound 33, or a solvate, hydrate, or isotopologue thereof, is prepared by a process comprising
(b) contacting Compound 32 of the Formula:

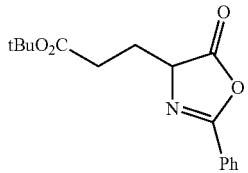

32 or a solvate, hydrate, or isotopologue thereof, with $NH_3$ to provide Compound 33, or a solvate, hydrate, or isotopologue thereof.

In one embodiment, Compound 32, or a solvate, hydrate, or isotopologue thereof, is prepared by a process comprising
(a) contacting Compound 31 of the Formula:

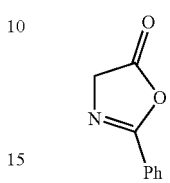

31 or a solvate, hydrate, or isotopologue thereof, with tert-butyl acrylate in the presence of a base to provide Compound 32, or a solvate, hydrate, or isotopologue thereof;

In one embodiment, the base in step (a) is sodium $C_{1-14}$ alkoxide, potassium $C_{1-14}$ alkoxide, sodium hydride, potassium hydride, calcium hydride, cesium carbonate, lithium hexamethyldisilazide (LiHMDS), lithium diisopropylamide (LDA), 2-tert-butyl-1,1,3,3-tetramethyl-guanidine (Barton's Base), 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-diisopropylethylamine (DIPEA or Hünig's base), pyridine, 2,6-di-tert-butyl-pyridine, 2,6-lutidine, lithium tetramethylpiperidide (LiTMP or harpoon base), 7-methyl-1,5,7 triazabicyclo[4.4.0]dec-5-ene (MTBD), 1,2,2,6,6-pentamethylpiperidine (PMP), 2,2,6,6-tetramethylpiperidine (TMP), tributylamine, 2,4,6-tri-tert-butylpyridine, tris(trimethylsilyl)amine, n-butyllithium, sec-butyllithium, tert-butyllithium, potassium bis(trimethylsilyl)amide, sodium tert-butoxide, tert-butylimino-tris(dimethylamino)phosphorane, or 2-tert-butylimino-2-diethylamino-1,3-dimethylperhydro-1,3,2-diazaphosphorine.

In one embodiment, the base in step (a) is triethylamine, diisopropylethylamine, pyridine, 4-dimethylaminopyridine, or 1,8-diazabicyclo[5.4.0]undec-7-ene (DBU). In one embodiment, the base in step (a) is DBU. In one embodiment, the base in step (a) is $Cs_2CO_3$.

In one embodiment, the $NH_3$ in step (b) is provided in the form of gaseous ammonia. In one embodiment, the $NH_3$ in step (b) is provided in the form of an ammonia solution. In one embodiment, the ammonia solution is an ammonia solution in water (e.g., $NH_4OH$). In one embodiment, the ammonia solution is an ammonia solution in an alcohol. In one embodiment, the alcohol is methanol, ethanol, n-propanol, or isopropanol, or a mixture thereof. In one embodiment, the ammonia solution is an ammonia solution in MeOH.

In one embodiment, the $NH_3$ in step (b) is provided in the form of ammonium salt. In one embodiment, the ammonium salt is $(NH_4)_2CO_3$, $NH_4HCO_3$, $NH_4OAc$, $NH_4H_2PO_4$, $(NH_4)_2HPO_4$, or $(NH_4)_3PO_4$. In one embodiment, the $NH_3$ in step (b) is provided in the form of $NH_4HCO_3$.

In one embodiment, the deprotection in step (c) occurs in the presence of a base. Other methods for benzoyl deprotection that are generally known to those skilled in the art can be used in step (c).

In one embodiment, step (d) comprises contacting the compound of Formula (I-rac), or a solvate, hydrate, or isotopologue thereof, with a chiral acid to provide a diastereomeric mixture of salts, and separating the resulted diastereomeric mixture of salts by selective crystallization. In one embodiment, the chiral acid is tartaric acid, 2,3-dibenzoyl tartaric acid, mandelic acid, camphorsulfonic acid, N-Ac-N-leucine, or N-Ac-L-phenylalanine. In one embodiment, the selective crystallization occurs in a solvent selected from MeOH, isopropanol, and n-propanol, or a mixture thereof.

Step (e) comprises optionally converting the compound of Formula (I), or a solvate, hydrate, enantiomer, mixture of enantiomers, or isotopologue thereof, to a salt of the compound. In one embodiment, the salt is a HCl, HBr, HOAc, or PhSO$_3$H salt. In one embodiment, the salt is a HCl salt. Methods for salt formation that are generally known to those of ordinary skill in the art can be used in step (e).

In one embodiment, Compound 31, or a solvate, hydrate, or isotopologue thereof, is prepared by a process comprising contacting Compound 30 of the Formula:

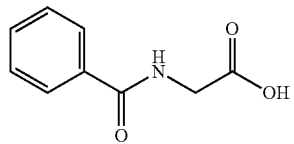

or a solvate, hydrate, or isotopologue thereof, with a cyclization reagent. In one embodiment, the cyclization reagent is DCC.

5.2.6 Preparation of a Compound of Formula (XIV)

The preparation of a compound of Formula (XIV) (i.e., Compound 37) has been previously described in U.S. Patent Publication No. 2014/0046058, which is incorporated herein by reference in its entirety. The preparation is summarized in the scheme below:

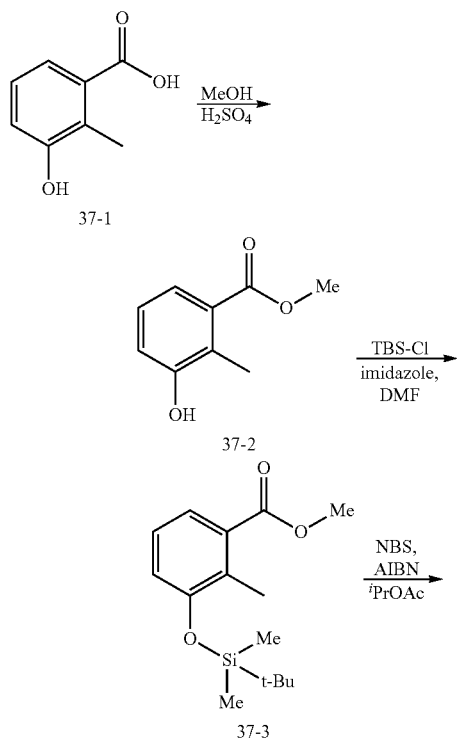

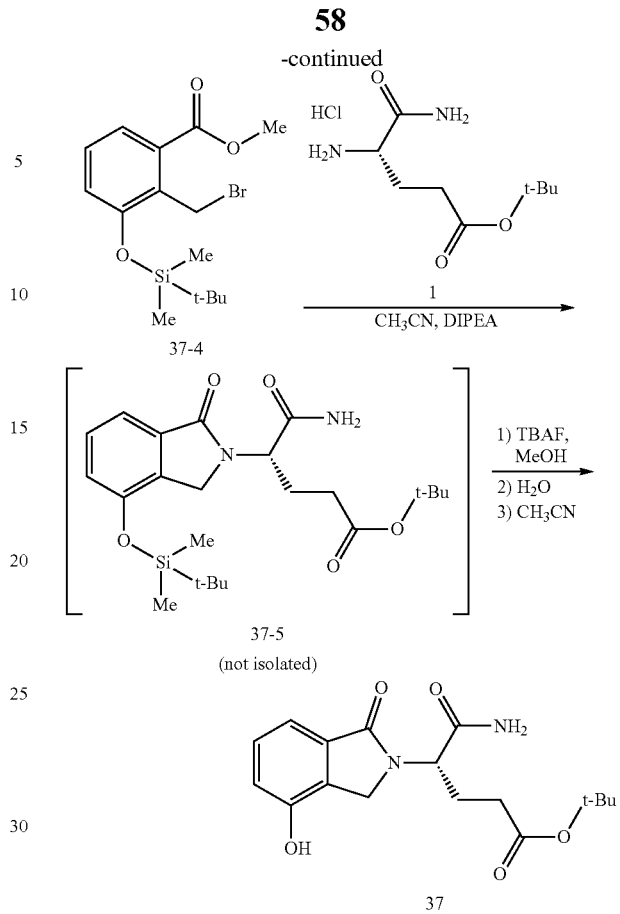

This process was implemented to manufacture multi-kilo batches of 37, however, it has several draw backs: The process involves multiple steps (six bond forming-breaking reactions). The process lacks crystalline, isolable intermediates. Compounds 37-3, 37-4, and 37-5 are not crystalline solids. This precludes the use of crystallization for purification. Crystallization is generally a preferred method of purification on kilogram or larger scale. As a consequence a large purification burden is put on the final step (isolation of 37), two crystallizations are required, the first of which has poor physical properties which leads to difficult handling. The process involves the use of a radical reaction (37-3 to 37-4) that can rapidly generate heat, and the heat can lead to side product formation (ring bromination) that is difficult to remove. The process involves the use of a bulky silyl protecting group (on 37-3, 37-4, and 37-5). This is an expensive piece that does not add atoms to the final compound. A need still exists for the development of alternative synthetic processes for a compound of Formula (XIV), such as Compound 37.

In one embodiment, provided herein are processes for the preparation of a compound of Formula (XIV), or a salt, solvate, hydrate, enantiomer, mixture of enantiomers, or isotopologue thereof, comprising a reductive amination reaction between a compound of a compound of Formula (I) and a 2-formylbenzoester (or a synthetic equivalent). The processes comprise an optional step of crystallization of the product from a solvent or mixture of solvents. In certain embodiments, the processes provided herein are significantly shorter (only two steps from a compound of Formula (XVI)) than the previous synthesis and result in higher yields.

In one embodiment, provided herein is a process for preparing a compound of Formula (XIV):

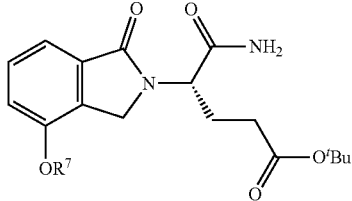
(XIV)

or a salt, solvate, hydrate, enantiomer, mixture of enantiomers, or isotopologue thereof, wherein $R^7$ is hydrogen or a suitable hydroxyl protecting group, comprising
(a) contacting a compound of Formula (XV):

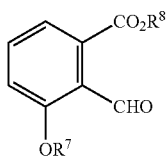
(XV)

or an analog of a compound of Formula (XV) that contains an aldehyde-equivalent and/or carboxylic-equivalent group, or a solvate, hydrate, enantiomer, mixture of enantiomers, or isotopologue thereof, wherein $R^8$ is hydrogen, alkyl, or aryl, with a compound of Formula (I):

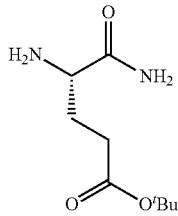
(I)

or a salt, solvate, hydrate, enantiomer, mixture of enantiomers, or isotopologue thereof, to provide a compound of Formula (XIV), or a salt, solvate, hydrate, enantiomer, mixture of enantiomers, or isotopologue thereof; and
(b) optionally crystallizing the compound of Formula (XIV), or a salt, solvate, hydrate, enantiomer, mixture of enantiomers, or isotopologue thereof, from a solvent or mixture of solvents.

In one embodiment, $R^7$ is hydrogen. In one embodiment, $R^7$ is a hydroxyl protecting group. In one embodiment, $R^7$ is a hydroxyl protecting group selected from the group consisting of allyl, methyl, 2-methoxyethoxymethyl (MEM), methoxymethyl (MOM), methoxythiomethyl, t-butoxymethyl, tri-isopropylsilyloxymethyl (TOM), ethyl, 1-ethoxyehtyl, isopropyl, t-butyl, benzyl, trityl (Tr), dimethoxytrityl (DMT), monomethoxytrityl (MMT), p-methoxybenzyl (PMB), acetyl, chloroacetyl, trichloroacetyl, trifluoroacetyl, pivaloyl (Piv), benzoyl, p-phenylbenzoyl, trimethylsilyl (TMS), triisopropylsilyl (TIPS), t-butyldimethylsilyl (TBDMS), and tetrahydropyranyl.

In one embodiment, $R^8$ is alkyl. In one embodiment, $R^8$ is a $C_{1-5}$ alkyl. In one embodiment, $R^8$ is methyl, ethyl, n-propyl, isopropyl, or tert-butyl. In one embodiment, $R^8$ is methyl. In one embodiment, $R^8$ is hydrogen. In one embodiment, $R^8$ is aryl. In one embodiment, $R^8$ is a $C_{6-10}$ aryl.

In one embodiment, an aldehyde-equivalent group is an acetal, hemiacetal, thioacetal, dithioacetal, aminal, or hemiaminal. In one embodiment, the aldehyde-equivalent group is formed with the adjacent carboxylic-equivalent group (which leads to a fused ring structure).

In one embodiment, a carboxylic-equivalent group is a carboxylic acid, carboxylic ester, carboxylic amide, carboxylic halide, lactone, lactam, or thiolactone.

In one embodiment, the analog of a compound of Formula (XV) that contains an aldehyde-equivalent and/or carboxylic-equivalent group is a compound of the formula:

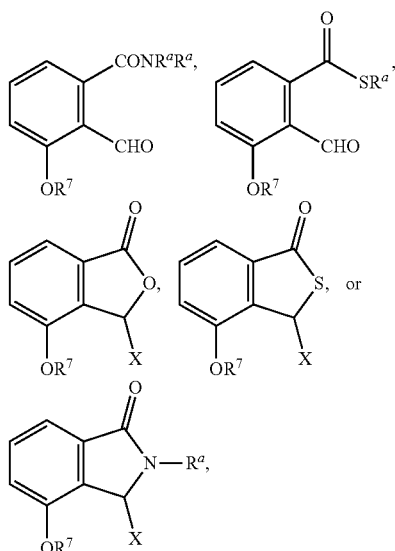

wherein:
each instance of $R^a$ is independently hydrogen, alkyl, aryl, acyl, or carbamoyl;
X is Cl, Br, $OR^b$, $SR^c$, $SO_3R^c$, or $NR^aR^a$;
$R^b$ is hydrogen, alkyl, aryl, acyl, or silyl; and
$R^c$ is hydrogen, alkyl, or aryl.

In one embodiment, the analog of a compound of Formula (XV) that contains an aldehyde-equivalent and/or carboxylic-equivalent group is a 4-hydroxy-3-alkoxyisobenzofuran-1(3H)-one.

In one embodiment, step (a) is conducted with a salt of a compound of Formula (I) selected from a hydrochloride salt, a sulfonic acid salt, a phosphoric acid salt, an achiral carboxylic acid salt, a chiral carboxylic acid salt, and a mineral acid salt. In one embodiment, step (a) is conducted with a hydrochloride salt of a compound of Formula (I).

In one embodiment, step (a) occurs in the presence of a reducing reagent and optionally a base. Without being bound by a particular theory, the base can be used to break up the salt of a compound of Formula (I), and the base can be absent depending on the identity of the salt or lack thereof.

In one embodiment, the reducing reagent is $NaBH(OAc)_3$, $NaBH_4$, $NaBH_3CN$, silanes, or $H_2$ in combination with a transition metal catalyst. In one embodiment, the transition metal catalyst is a Pd, Pt, Rh, or Ir catalyst. In one embodiment, the transition metal catalyst is a Pd catalyst. In one embodiment, the reducing reagent is $NaBH(OAc)_3$.

In one embodiment, the base is iPr$_2$NEt, Et$_3$N, n-Bu$_3$N, DBU, or tetramethyl guanidine. In one embodiment, the base is iPr$_2$Net.

In one embodiment, step (a) occurs in a solvent selected from DMAc, MeOH, EtOH, trifluoroethanol, i-PrOH, 1-propanol, t-butanol, MeCN, DMF, NMP, THF, 2-MeTHF, DCM, and DCE, or a mixture thereof. In one embodiment, step (a) occurs in a solvent of DMAc.

In one embodiment, the reaction temperature of step (a) is no more than about 5° C. In one embodiment, the reaction temperature of step (a) after contacting the compound of Formula (XV) and the compound of Formula (I) but before adding the reducing reagent is no more than about 5° C. In one embodiment, the reaction temperature is from about 0° C. to about 5° C.

In one embodiment, the crystallization of step (b) occurs in a solvent mixture of DMAc and water. In one embodiment, the crystallization of step (b) occurs in a solvent mixture of THF and heptanes.

5.2.7 Preparation of a Compound of Formula (XV)

In one embodiment, provided herein are processes for the preparation of a compound of Formula (XV), or a salt, solvate, hydrate, enantiomer, mixture of enantiomers, or isotopologue thereof, comprising a formylation reaction of a compound of Formula (XVI). The processes comprise an optional step of crystallization of the product from a solvent or mixture of solvents.

In one embodiment, provided herein is a process for preparing a compound of Formula (XV):

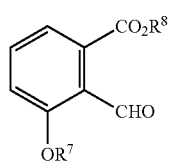

(XV)

or a salt, solvate, hydrate, enantiomer, mixture of enantiomers, or isotopologue thereof, wherein R$^7$ is hydrogen or a suitable hydroxyl protecting group, and R$^8$ is hydrogen, alkyl, or aryl, comprising (a) contacting a compound of Formula (XVI):

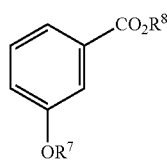

(XVI)

or a solvate, hydrate, enantiomer, mixture of enantiomers, or isotopologue thereof, with a formylating reagent, to provide a compound of Formula (XV), or a salt, solvate, hydrate, enantiomer, mixture of enantiomers, or isotopologue thereof; and (b) optionally crystallizing the compound of Formula (XV), or a salt, solvate, hydrate, enantiomer, mixture of enantiomers, or isotopologue thereof, from a solvent or mixture of solvents.

In one embodiment, R$^7$ is hydrogen. In one embodiment, R$^7$ is a hydroxyl protecting group. In one embodiment, R$^7$ is a hydroxyl protecting group selected from the group consisting of allyl, methyl, 2-methoxyethoxymethyl (MEM), methoxymethyl (MOM), methoxythiomethyl, t-butoxymethyl, tri-isopropylsilyloxymethyl (TOM), ethyl, 1-ethoxyehtyl, isopropyl, t-butyl, benzyl, trityl (Tr), dimethoxytrityl (DMT), monomethoxytrityl (MMT), p-methoxybenzyl (PMB), acetyl, chloroacetyl, trichloroacetyl, trifluoroacetyl, pivaloyl (Piv), benzoyl, p-phenylbenzoyl, trimethylsilyl (TMS), triisopropylsilyl (TIPS), t-butyldimethylsilyl (TBDMS), and tetrahydropyranyl.

In one embodiment, R$^8$ is alkyl. In one embodiment, R$^8$ is a C$_{1-5}$ alkyl. In one embodiment, R$^8$ is methyl, ethyl, n-propyl, isopropyl, or tert-butyl. In one embodiment, R$^8$ is methyl. In one embodiment, R$^8$ is hydrogen. In one embodiment, R$^8$ is aryl. In one embodiment, R$^8$ is a C$_{6-10}$ aryl.

In one embodiment, the formylating reagent in step (a) is hexamethylenetetramine (HMTA), a combination of POCl$_3$ and DMF (e.g., the Vilsmeir-Haack reaction), a combination of oxalyl chloride and DMF (e.g., the Vilsmeir-Haack reaction), a combination of CHCl$_3$ and KOH (e.g., the Reimer-Tiemann reaction), a combination of HCN, HCl, and AlCl$_3$ (e.g., the Gattermann reaction), and a combination of CO and HCl (e.g., the Gattermann-Koch reaction). In one embodiment, the formylating reagent in step (a) is hexamethylenetetramine (HMTA). HMTA has a structure of

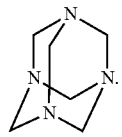

In one embodiment, the crystallization of step (b) occurs in a solvent selected from MeOH, EtOH, iPrOH, n-propanol, t-butanol, n-butanol, MeCN, DMSO, DMAc, DMF, NMP, THF, water, or a mixture thereof. In one embodiment, the crystallization of step (b) occurs in a solvent mixture of MeOH and water. In one embodiment, the crystallization of step (b) occurs in a solvent mixture of iPrOH and water.

In one embodiment, step (b) further comprises adjusting the pH by a base. In one embodiment, the pH is adjusted to about 2.5 to about 4. In one embodiment, the base is a carbonate, phosphate, bicarbonate, hydroxide, acetate, or benzoate base. In one embodiment, the base is a carbonate base. In one embodiment, the base is K$_2$CO$_3$. In one embodiment, the base is potassium acetate, sodium carbonate, lithium carbonate, hydroxides, bicarbonates, tertiary amines, DBU, or guanidine.

In one embodiment, the product from step (b) is further slurried in a mixture of a water miscible solvent and an acid solvent. In one embodiment, the water miscible solvent is methanol, ethanol, propanol, acetonitrile, DMF, DMAc, NW, DMSO, or THF. In one embodiment, the water miscible solvent is i-PrOH. In one embodiment, the acid solvent is AcOH, sulfonic acids, carboxcylic acids, mineral acids, or amino acids. In one embodiment, the acid solvent is AcOH. In one embodiment, the product from step (b) is further slurried in a mixture of i-PrOH and AcOH.

In one embodiment, also provided herein are processes for the preparation of a compound of Formula (XV), or a salt, solvate, hydrate, enantiomer, mixture of enantiomers, or isotopologue thereof, comprising ortho-metallation of O-protected compound of Formula (XVI), followed by reaction with a formylating reagent (e.g., DMF). One embodiment of the process is depicted in the scheme below:

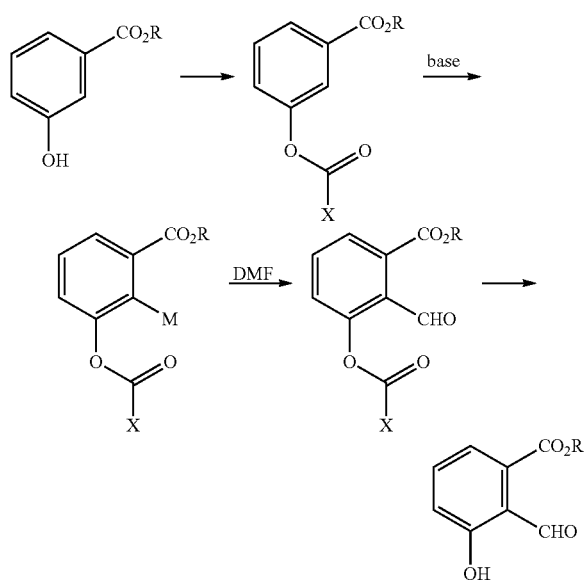

R = H, Alkyl, aryl
X = OR' (R' = alkyl, aryl)
NR"₂ (R" = alkyl, aryl)

or related variations (nitrile, thioester, or amide instead of the ester at the 1-position).

In one embodiment, also provided herein are processes for the preparation of a compound of Formula (XV), or a salt, solvate, hydrate, enantiomer, mixture of enantiomers, or isotopologue thereof, comprising carboxymetallation of 2-chloro-6-hydroxybenzaldehyde Pd/CO/MeOH) One embodiment of the process is depicted in the scheme below:

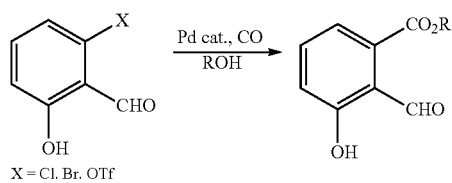

X = Cl, Br, OTf or related variations (formation of amide with use of amine instead of alcohol ROH)

5.2.8 Preparation of O-t-Bu-DIC Isourea

In one embodiment, provided herein are processes for the preparation of O-t-Bu-DIC isourea of the structure:

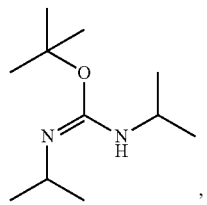

comprising reacting diisopropylcarbodiimide (DIC) with t-butanol and a Cu(I) salt in the presence of oxygen.

In one embodiment, the oxygen is present in an amount of up to about 22% of the atmosphere. In one embodiment, the oxygen is present in an amount of from about 1% to about 10% of the atmosphere. In one embodiment, the oxygen is present in an amount of from about 2% to about 6% of the atmosphere. In one embodiment, the oxygen is present in an amount of about 4% of the atmosphere.

In one embodiment, the Cu(I) salt is CuCl. In one embodiment, the Cu(I) salt is CuBr. In one embodiment, the Cu(I) salt is CuI The O-t-Bu-DIC isourea can be used to prepare the t-butyl ester compounds provided herein (e.g., a compound of Formula (IV)) as well as other t-butyl ester compounds from the corresponding acid compounds. It is generally known in the chemistry field that running organic reactions under oxygen can be hazardous, especially on large scale. Without being limited by a particular theory, the amount of oxygen provided herein (e.g., about 4% oxygen in nitrogen) is found to be both safe and effective. The advantage provided by the presence of oxygen is not trivial, especially on large scale.

5.3 Solid Forms

In one embodiment, provided herein are intermediate compounds used in or product compounds prepared by the processes provided herein, including solid forms (e.g., crystalline forms) thereof. In one embodiment, provided herein are solid forms (e.g., Form A) comprising Compound 7. In one embodiment, provided herein are solid forms (e.g., Form A) comprising racemic Compound 7. In one embodiment, provided herein are solid forms (e.g., Form A) comprising Compound 8. In one embodiment, provided herein are solid forms (e.g., Form A) comprising racemic Compound 8. In one embodiment, provided herein are solid forms (e.g., Form A and Form B) comprising Compound 1. In one embodiment, provided herein are solid forms (e.g., Form A) comprising racemic Compound 1. In one embodiment, provided herein are solid forms (e.g., Form A) comprising Compound 35. In one embodiment, provided herein are solid forms (e.g., Form 1) comprising Compound 37. In one embodiment, provided herein are solid forms (e.g., Form 1) comprising racemic Compound 37.

5.3.1 Form A of Compound 7

In one embodiment, provided herein is a solid form comprising Compound 7 of the formula:

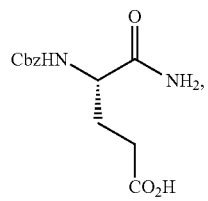

7 wherein the solid form is Form A (of Compound 7).

A representative XRPD pattern of the Form A is provided in FIG. 1. In one embodiment, provided herein is a solid form comprising Compound 7, characterized by 1, 2, 3, 4, 5, 6, 7, 8, 9, 10, 11, 12, 13, 14, 15, 16, 17, 18, 19, 20, 21, or all of the XRPD peaks located at the following or approximately the following positions: 6.7, 9.0, 10.7, 13.0, 16.6, 17.1, 18.7, 19.6, 20.1, 21.5, 21.8, 23.7, 24.3, 24.9, 25.5, 26.3, 28.7, 29.0, 30.4, 31.5, 31.8, and 34.8 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising Compound 7, having an XRPD pattern comprising peaks at approximately 9.0, 10.7, and 23.7 degrees 2θ. In one embodiment, the XRPD pattern further comprises peaks at approximately 13.0, 17.1, and 18.7 degrees 2θ. In one embodiment, the XRPD pattern further comprises peaks at approximately 21.8 and 25.5 degrees 2θ. In one embodiment, the XRPD pattern comprises peaks at approximately 9.0, 10.7, 13.0, 17.1, 18.7, 20.1, 21.5, 21.8, 23.7, 25.5, 28.7, and 30.4 degrees 2θ.

In one embodiment, provided herein is a solid form comprising Compound 7, having an XRPD pattern which matches the XRPD pattern presented in FIG. 1.

In one embodiment, the XRPD patterns are obtained using Cu Kα radiation.

A representative DSC thermogram of the Form A is presented in FIG. 2. In one embodiment, provided herein is a solid form comprising Compound 7, having a DSC thermogram comprising a thermal event with an onset temperature of about 180° C. In one embodiment, the thermal event also has a peak temperature of about 180° C. In one embodiment, provided herein is a solid form comprising Compound 7, having a DSC thermogram which matches the DSC thermogram presented in FIG. 2.

5.3.2 Form a of Racemic Compound 7

In one embodiment, provided herein is a solid form comprising racemic Compound 7 of the formula:

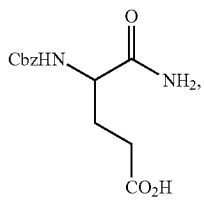

rac-7 wherein the solid form is Form A (of racemic Compound 7).

A representative XRPD pattern of the Form A is provided in FIG. 3. In one embodiment, provided herein is a solid form comprising racemic Compound 7, characterized by 1, 2, 3, 4, 5, 6, 7, 8, 9, 10, 11, 12, 13, 14, 15, 16, 17, 18, or all of the XRPD peaks located at the following or approximately the following positions: 6.6, 8.5, 10.1, 11.5, 14.9, 17.6, 20.0, 20.8, 23.1, 23.7, 24.7, 24.9, 25.8, 27.5, 27.6, 28.1, 30.7, 33.7, and 35.9 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising racemic Compound 7, having an XRPD pattern comprising peaks at approximately 8.5, 14.9, and 20.8 degrees 2θ. In one embodiment, the XRPD pattern further comprises peaks at approximately 10.1, 20.0, and 23.1 degrees 2θ. In one embodiment, the XRPD pattern further comprises peaks at approximately 24.7 and 33.7 degrees 2θ. In one embodiment, the XRPD pattern comprises peaks at approximately 6.6, 8.5, 10.1, 14.9, 20.0, 20.8, 23.1, 24.7, 27.5, 27.6, 28.1, 30.7, and 33.7 degrees 2θ.

In one embodiment, provided herein is a solid form comprising racemic Compound 7, having an XRPD pattern which matches the XRPD pattern presented in FIG. 3.

In one embodiment, the XRPD patterns are obtained using Cu Kα radiation.

A representative DSC thermogram of the Form A is presented in FIG. 4. In one embodiment, provided herein is a solid form comprising racemic Compound 7, having a DSC thermogram comprising a thermal event with an onset temperature of about 156° C. In one embodiment, the thermal event also has a peak temperature of about 158° C. In one embodiment, provided herein is a solid form comprising racemic Compound 7, having a DSC thermogram which matches the DSC thermogram presented in FIG. 4.

5.3.3 Form A of Compound 8

In one embodiment, provided herein is a solid form comprising Compound 8 of the formula:

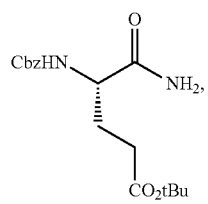

8 wherein the solid form is Form A (of Compound 8).

A representative XRPD pattern of the Form A is provided in FIG. 5. In one embodiment, provided herein is a solid form comprising Compound 8, characterized by 1, 2, 3, 4, 5, 6, 7, 8, 9, 10, 11, 12, 13, 14, 15, 16, 17, 18, or all of the XRPD peaks located at the following or approximately the following positions: 6.0, 9.1, 11.3, 12.0, 13.9, 15.3, 16.6, 18.1, 19.4, 21.3, 22.3, 22.8, 24.2, 25.2, 28.0, 28.2, 30.7, 33.5, and 34.2 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising Compound 8, having an XRPD pattern comprising peaks at approximately 6.0, 18.1, and 19.4 degrees 2θ. In one embodiment, the XRPD pattern further comprises peaks at approximately 11.3, 13.9, and 16.6 degrees 2θ. In one embodiment, the XRPD pattern further comprises peaks at approximately 24.2 and 25.2 degrees 2θ. In one embodiment, the XRPD pattern comprises peaks at approximately 6.0, 9.1, 11.3, 13.9, 16.6, 18.1, 19.4, 22.3, 24.2, 25.2, and 28.2 degrees 2θ.

In one embodiment, provided herein is a solid form comprising Compound 8, having an XRPD pattern which matches the XRPD pattern presented in FIG. 5.

In one embodiment, the XRPD patterns are obtained using Cu Kα radiation.

A representative DSC thermogram of the Form A is presented in FIG. 6. In one embodiment, provided herein is a solid form comprising Compound 8, having a DSC thermogram comprising a thermal event with an onset temperature of about 139° C. In one embodiment, the thermal event also has a peak temperature of about 140° C. In one embodiment, provided herein is a solid form comprising Compound 8, having a DSC thermogram which matches the DSC thermogram presented in FIG. 6.

5.3.4 Form a of Racemic Compound 8

In one embodiment, provided herein is a solid form comprising racemic Compound 8 of the formula:

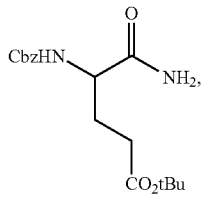

rac-8 wherein the solid form is Form A (of racemic Compound 8).

A representative XRPD pattern of the Form A is provided in FIG. 7. In one embodiment, provided herein is a solid form comprising racemic Compound 8, characterized by 1, 2, 3, 4, 5, 6, 7, 8, 9, 10, 11, 12, 13, 14, 15, 16, 17, 18, 19, 20, 21, 22, 23, 24, or all of the XRPD peaks located at the following or approximately the following positions: 6.4, 8.6, 9.0, 9.6, 10.5, 15.1, 16.0, 16.7, 17.1, 18.1, 18.5, 18.9, 19.3, 19.6, 20.1, 20.3, 20.5, 21.3, 21.4, 22.2, 22.4, 22.6, 22.9, 23.5, and 24.8 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising racemic Compound 8, having an XRPD pattern comprising peaks at approximately 6.4, 8.6, and 16.7 degrees 2θ. In one embodiment, the XRPD pattern further comprises peaks at approximately 10.5, 17.1, and 20.5 degrees 2θ. In one embodiment, the XRPD pattern further comprises peaks at approximately 15.1 and 19.6 degrees 2θ. In one embodiment, the XRPD pattern comprises peaks at approximately 6.4, 8.6, 10.5, 15.1, 16.0, 16.7, 17.1, 18.1, 19.6, 20.1, 20.3, 20.5, 21.3, and 23.5 degrees 2θ.

In one embodiment, provided herein is a solid form comprising racemic Compound 8, having an XRPD pattern which matches the XRPD pattern presented in FIG. 7.

In one embodiment, the XRPD patterns are obtained using Cu Kα radiation.

A representative DSC thermogram of the Form A is presented in FIG. 8. In one embodiment, provided herein is a solid form comprising racemic Compound 8, having a DSC thermogram comprising a thermal event with an onset temperature of about 122° C. In one embodiment, the thermal event also has a peak temperature of about 124° C. In one embodiment, provided herein is a solid form comprising racemic Compound 8, having a DSC thermogram which matches the DSC thermogram presented in FIG. 8.

5.3.5 Form A of Compound 1

In one embodiment, provided herein is a solid form comprising Compound 1 of the formula:

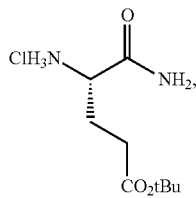

1 wherein the solid form is Form A (of Compound 1).

A representative XRPD pattern of the Form A is provided in FIG. 9. In one embodiment, provided herein is a solid form comprising Compound 1, characterized by 1, 2, 3, 4, 5, 6, 7, 8, 9, or all of the XRPD peaks located at the following or approximately the following positions: 4.8, 14.4, 15.6, 19.2, 24.1, 24.9, 29.0, 34.0, 34.9, and 39.0 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by all of the peaks.

In one embodiment, provided herein is a solid form comprising Compound 1, having an XRPD pattern comprising peaks at approximately 4.8, 19.2, and 24.1 degrees 2θ. In one embodiment, the XRPD pattern further comprises peaks at approximately 14.4 and 29.0 degrees 2θ. In one embodiment, the XRPD pattern comprises peaks at approximately 4.8, 14.4, 15.6, 19.2, 24.1, 24.9, 29.0, and 34.0 degrees 2θ.

In one embodiment, provided herein is a solid form comprising Compound 1, having an XRPD pattern which matches the XRPD pattern presented in FIG. 9.

In one embodiment, the XRPD patterns are obtained using Cu Kα radiation.

A representative DSC thermogram of the Form A is presented in FIG. 10. In one embodiment, provided herein is a solid form comprising Compound 1, having a DSC thermogram comprising a first thermal event with an onset temperature of about 197° C., a second thermal event with an onset temperature of about 206° C., and a third thermal event with an onset temperature of about 218° C. In one embodiment, the first thermal event also has a peak temperature of about 197° C., the second thermal event also has a peak temperature of about 207° C., and the third thermal event also has a peak temperature of about 224° C. In one embodiment, provided herein is a solid form comprising Compound 1, having a DSC thermogram which matches the DSC thermogram presented in FIG. 10.

5.3.6 Form B of Compound 1

In one embodiment, provided herein is a solid form comprising Compound 1 of the formula:

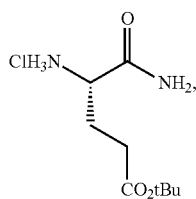

1 wherein the solid form is Form B (of Compound 1).

A representative XRPD pattern of the Form B is provided in FIG. 11. In one embodiment, provided herein is a solid form comprising Compound 1, characterized by 1, 2, 3, 4, 5, 6, 7, 8, 9, 10, 11, 12, 13, 14, 15, 16, 17, 18, 19, 20, 21, 22, 23, or all of the XRPD peaks located at the following or approximately the following positions: 7.7, 12.1, 15.4, 16.0, 18.1, 18.8, 19.2, 19.4, 22.1, 24.4, 24.9, 27.1, 28.1, 28.6, 29.4, 31.1, 31.4, 32.4, 32.6, 32.8, 34.5, 36.1, 36.2, and 36.9 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising Compound 1, having an XRPD pattern comprising peaks at approximately 12.1, 18.8, and 19.4 degrees 2θ. In one embodiment, the XRPD pattern further comprises peaks at approximately 19.2, 24.9, and 31.1 degrees 2θ. In one embodiment, the XRPD pattern further comprises peaks at approximately 18.1 and 28.6 degrees 2θ. In one embodiment, the XRPD pattern comprises peaks at approximately 12.1, 18.1, 18.8, 19.2, 19.4, 22.1, 24.4, 24.9, 27.1, 28.6, and 31.1 degrees 2θ.

In one embodiment, provided herein is a solid form comprising Compound 1, having an XRPD pattern which matches the XRPD pattern presented in FIG. 11.

In one embodiment, the XRPD patterns are obtained using Cu Kα radiation.

A representative DSC thermogram of the Form B is presented in FIG. 12. In one embodiment, provided herein is a solid form comprising Compound 1, having a DSC thermogram comprising a first thermal event with an onset temperature of about 139° C., a second thermal event with an onset temperature of about 193° C., a third thermal event with an onset temperature of about 205° C., and a fourth thermal event with an onset temperature of about 224° C. In one embodiment, the first thermal event also has a peak temperature of about 146° C., the second thermal event also has a peak temperature of about 197° C., the third thermal event also has a peak temperature of about 208° C., and the fourth thermal event also has a peak temperature of about 224° C. In one embodiment, provided herein is a solid form comprising Compound 1, having a DSC thermogram which matches the DSC thermogram presented in FIG. 12.

5.3.7 Form a of Racemic Compound 1

In one embodiment, provided herein is a solid form comprising racemic Compound 1 of the formula:

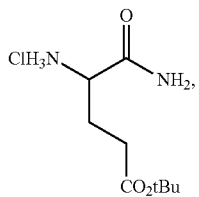

rac-1 wherein the solid form is Form A (of racemic Compound 1).

A representative XRPD pattern of the Form A is provided in FIG. 13. In one embodiment, provided herein is a solid form comprising racemic Compound 1, characterized by 1, 2, 3, 4, 5, 6, 7, 8, 9, 10, 11, 12, 13, 14, 15, 16, 17, 18, 19, 20, 21, 22, or all of the XRPD peaks located at the following or approximately the following positions: 7.9, 9.2, 12.2, 13.7, 16.2, 16.4, 17.0, 18.7, 19.7, 20.2, 20.4, 21.0, 21.3, 22.7, 23.7, 25.9, 26.3, 28.1, 29.7, 31.1, 32.2, 33.0, and 34.2 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising racemic Compound 1, having an XRPD pattern comprising peaks at approximately 18.7, 21.3, and 25.9 degrees 2θ. In one embodiment, the XRPD pattern further comprises peaks at approximately 7.9, 20.2, and 22.7 degrees 2θ. In one embodiment, the XRPD pattern further comprises peaks at approximately 9.2 and 19.7 degrees 2θ. In one embodiment, the XRPD pattern comprises peaks at approximately 7.9, 9.2, 13.7, 18.7, 19.7, 20.2, 20.4, 21.0, 21.3, 22.7, 25.9, and 34.2 degrees 2θ.

In one embodiment, provided herein is a solid form comprising racemic Compound 1, having an XRPD pattern which matches the XRPD pattern presented in FIG. 13.

In one embodiment, the XRPD patterns are obtained using Cu Kα radiation.

A representative DSC thermogram of the Form A is presented in FIG. 14. In one embodiment, provided herein is a solid form comprising racemic Compound 1, having a DSC thermogram comprising a first thermal event with an onset temperature of about 186° C., and a second thermal event with an onset temperature of about 207° C. In one embodiment, the first thermal event also has a peak temperature of about 189° C., and the second thermal event also has a peak temperature of about 212° C. In one embodiment, provided herein is a solid form comprising racemic Compound 1, having a DSC thermogram which matches the DSC thermogram presented in FIG. 14.

5.3.8 Form A of Compound 35

In one embodiment, provided herein is a solid form comprising Compound 35 of the formula:

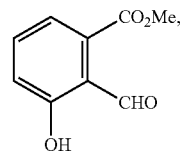

35 wherein the solid form is Form A (of Compound 35).

A representative XRPD pattern of the Form A is provided in FIG. 15. In one embodiment, provided herein is a solid form comprising Compound 35, characterized by 1, 2, 3, 4, 5, 6, 7, 8, 9, 10, 11, 12, 13, 14, 15, or all of the XRPD peaks located at the following or approximately the following positions: 9.1, 12.0, 15.6, 18.1, 19.8, 24.1, 24.6, 25.0, 25.3, 26.2, 27.1, 28.5, 29.9, 31.8, 36.6, and 37.8 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising Compound 35, having an XRPD pattern comprising peaks at approximately 12.0, 15.6, and 24.1 degrees 2θ. In one embodiment, the XRPD pattern further comprises peaks at approximately 9.1, 18.1, and 19.8 degrees 2θ. In one embodiment, the XRPD pattern further comprises peaks at approximately 25.0 and 27.1 degrees 2θ. In one embodiment, the XRPD pattern comprises peaks at approximately 9.1, 12.0, 15.6, 18.1, 19.8, 24.1, 24.6, 25.0, 25.3, 26.2, 27.1, 28.5, and 29.9 degrees 2θ.

In one embodiment, provided herein is a solid form comprising Compound 35, having an XRPD pattern which matches the XRPD pattern presented in FIG. 15.

In one embodiment, the XRPD patterns are obtained using Cu Kα radiation.

A representative DSC thermogram of the Form A is presented in FIG. 16. In one embodiment, provided herein is a solid form comprising Compound 35, having a DSC thermogram comprising a first thermal event with an onset temperature of about 58° C., and a second thermal event with an onset temperature of about 119° C. In one embodiment, the first thermal event also has a peak temperature of about 60° C., and the second thermal event also has a peak temperature of about 163° C. In one embodiment, provided herein is a solid form comprising Compound 35, having a DSC thermogram which matches the DSC thermogram presented in FIG. 16.

In one embodiment, Form A has approximately unit cell dimensions of: a=19.5 Å, b=3.8 Å, c=11.3 Å, α=90°, γ=90°, and γ=90°. In one embodiment, Form A has approximately unit cell dimensions of: a=19.46 Å, b=3.78 Å, c=11.26 Å, α=90°, β=90°, and γ=90°. In one embodiment, Form A has approximately unit cell dimensions of: a=19.458 Å, b=3.781 Å, c=11.261 Å, α=90°, β=90°, and γ=90°. In one embodiment, Form A has a unit cell of a space group of $Pna2_1$. In one embodiment, Form A has a volume of about 828.43 Å$^3$/cell. In one embodiment, Form A has a Z value of 4. In one embodiment, Form A has a density of about 1.444 g/cm$^3$.

5.3.9 Form 1 of Compound 37

In one embodiment, provided herein is a solid form comprising Compound 37 of the formula:

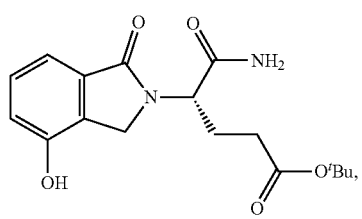

37 wherein the solid form is Form 1 (of Compound 37).

A representative XRPD pattern of the Form 1 is provided in FIG. 17. In one embodiment, provided herein is a solid form comprising Compound 37, characterized by 1, 2, 3, 4, 5, 6, 7, 8, 9, 10, 11, 12, 13, 14, 15, 16, 17, 18, 19, 20, 21, 22, 23, or all of the XRPD peaks located at the following or approximately the following positions: 5.4, 10.3, 10.7, 11.9, 13.5, 14.4, 16.0, 16.1, 18.0, 18.4, 18.7, 19.2, 19.6, 20.1, 20.7, 21.0, 22.2, 22.3, 23.0, 23.3, 24.7, 25.8, 26.2, and 27.0 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising Compound 37, having an XRPD pattern comprising peaks at approximately 5.4, 16.0, and 18.0 degrees 2θ. In one embodiment, the XRPD pattern further comprises peaks at approximately 10.7, 20.1, and 27.0 degrees 2θ. In one embodiment, the XRPD pattern further comprises peaks at approximately 14.4 and 23.0 degrees 2θ. In one embodiment, the XRPD pattern comprises peaks at approximately 5.4, 10.3, 10.7, 11.9, 13.5, 14.4, 16.0, 18.0, 18.4, 18.7, 19.2, 19.6, 20.1, 21.0, 22.2, 23.0, 24.7, 25.8, and 27.0 degrees 2θ.

In one embodiment, provided herein is a solid form comprising Compound 37, having an XRPD pattern which matches the XRPD pattern presented in FIG. 17.

In one embodiment, the XRPD patterns are obtained using Cu Kα radiation.

A representative DSC thermogram of the Form 1 is presented in FIG. 18. In one embodiment, provided herein is a solid form comprising Compound 37, having a DSC thermogram comprising a first thermal event with an onset temperature of about 189° C., and a second thermal event with an onset temperature of about 206° C. In one embodiment, the first thermal event also has a peak temperature of about 191° C., and the second thermal event also has a peak temperature of about 208° C. In one embodiment, provided herein is a solid form comprising Compound 37, having a DSC thermogram which matches the DSC thermogram presented in FIG. 18.

In one embodiment, Form 1 has approximately unit cell dimensions of: a=10.1 Å, b=10.9 Å, c=32.7 Å, α=90°, β=90°, and γ=90°. In one embodiment, Form 1 has approximately unit cell dimensions of: a=10.07 Å, b=10.89 Å, c=32.70 Å, a=90°, R=90°, and γ=90°. In one embodiment, Form 1 has approximately unit cell dimensions of: a=10.066 Å, b=10.887 Å, c=32.698 Å, α=90°, R=90°, and γ=90°. In one embodiment, Form 1 has a unit cell of a space group of $P2_12_12_1$. In one embodiment, Form 1 has a volume of about 3583.0 Å$^3$/cell. In one embodiment, Form 1 has a Z value of 8. In one embodiment, Form 1 has a density of about 1.240 g/cm$^3$.

5.3.10 Form 1 of Racemic Compound 37

In one embodiment, provided herein is a solid form comprising racemic Compound 37 of the formula:

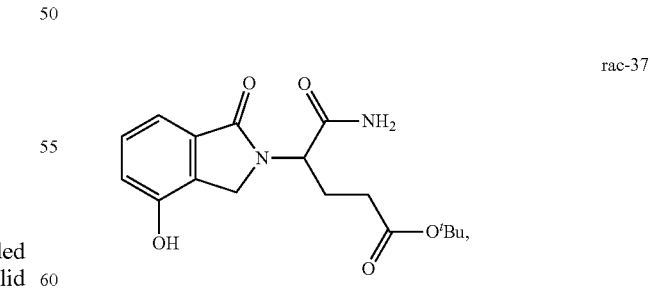

rac-37 wherein the solid form is Form 1 (of racemic Compound 37).

A representative XRPD pattern of the Form 1 is provided in FIG. 20. In one embodiment, provided herein is a solid form comprising racemic Compound 37, characterized by 1, 2, 3, 4, 5, 6, 7, 8, 9, 10, 11, 12, 13, 14, 15, 16, 17, 18, 19, 20, 21, 22, 23, 24, 25, or all of the XRPD peaks located at the following or approximately the following positions: 7.2, 7.5, 11.4, 12.5, 12.9, 14.3, 14.8, 15.0, 16.1, 16.8, 18.5, 19.7, 20.5, 21.1, 22.6, 23.7, 24.2, 25.2, 25.4, 25.9, 26.5, 28.1, 30.3, 30.6, 37.5, and 39.5 degrees 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 10 of the peaks. In one embodiment, the solid form is characterized by 13 of the peaks. In one embodiment, the solid form is characterized by all of the peaks.

In one embodiment, provided herein is a solid form comprising racemic Compound 37, having an XRPD pattern comprising peaks at approximately 7.5, 11.4, and 25.9 degrees 2θ. In one embodiment, the XRPD pattern further comprises peaks at approximately 16.8, 19.7, and 25.4 degrees 2θ. In one embodiment, the XRPD pattern further comprises peaks at approximately 12.9 and 22.6 degrees 2θ. In one embodiment, the XRPD pattern comprises peaks at approximately 7.5, 11.4, 12.5, 12.9, 15.0, 16.8, 19.7, 22.6, 25.4, and 25.9 degrees 2θ.

In one embodiment, provided herein is a solid form comprising racemic Compound 37, having an XRPD pattern which matches the XRPD pattern presented in FIG. 20.

In one embodiment, the XRPD patterns are obtained using Cu Kα radiation.

A representative DSC thermogram of the Form 1 is presented in FIG. 21. In one embodiment, provided herein is a solid form comprising racemic Compound 37, having a DSC thermogram comprising a first thermal event with an onset temperature of about 163° C. In one embodiment, the first thermal event also has a peak temperature of about 164° C. In one embodiment, the DSC thermogram further comprises a second thermal event with a peak temperature of about 207° C. In one embodiment, provided herein is a solid form comprising racemic Compound 37, having a DSC thermogram which matches the DSC thermogram presented in FIG. 21.

All of the combinations of the above embodiments are encompassed by this invention.

6. EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); M (molar); mM (millimolar); μM (micromolar); eq. (equivalent); mmol (millimoles); Hz (Hertz); MHz (megahertz); hr or hrs (hour or hours); min (minutes); and MS (mass spectrometry). Unless otherwise specified, the water content in a compound provided herein is determined by Karl Fisher (KF) method.

For all of the following examples, unless otherwise specified, standard work-up and purification methods known to those skilled in the art can be utilized. Unless otherwise specified, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

Example 1

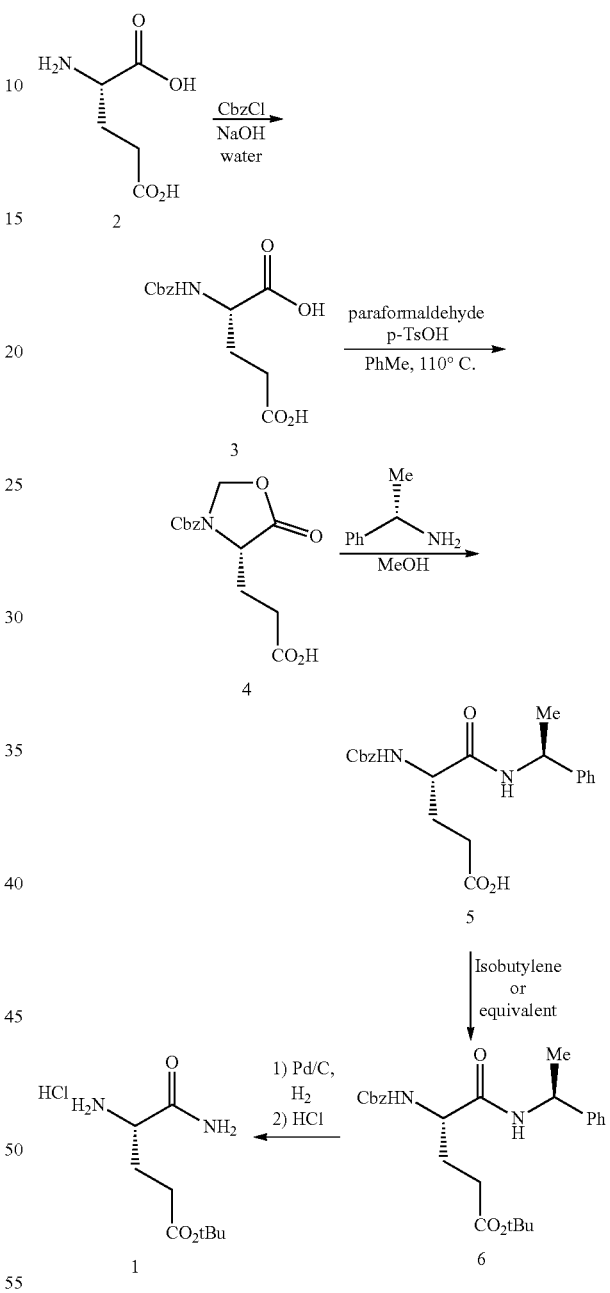

Step 1: Synthesis of Compound 3

To L-glutamic acid (2, 10 g, 68.0 mmol) was charged water 60 ml. To the resulting suspension, benzyl chloroformate (CbzCl, 9.16 ml, 63.9 mmol) was slowly charged. 2N NaOH (60 mL) was simultaneously charged to maintain a pH of 10-12. The addition rates were adjusted to maintain a batch temperature of 0-5° C. After addition of the CbzCl the mixture was stirred at 5° C. for 1 hr then 20 to 25° C. for an additional 16 hr. The mixture was then washed with EtOAc.

The product containing aqueous layer was acidified to pH=2-3 by adding conc. HCl, and was then extracted into EtOAc. The organic layer was dried over Na$_2$SO$_4$ and concentrated under reduced pressure. The resulted solid was dried in oven at 35-40° C. overnight to give 16 g of compound 3 (84%). LC-MS: Calc. m/e (M+1), 282.1; found: 282.2. $^1$H NMR (DMSO-d$_6$): δ (ppm)=1.68-1.83 (m, 1H), 1.91-2.03 (m, 1H), 2.27-2.35 (m, 2H), 3.99-4.22 (m, 1H), 5.03 (s, 2H), 7.29-7.40 (m, 5H), 7.59 (d, J=8.13 Hz, 1H), 12.40 (broad s, 2H).

Step 2: Synthesis of Compound 4

To Compound 3 (10 g, 35.6 mmol) in toluene (150 ml) was added paraformaldehyde (2.67 g, 89 mmol) and toluensulfonic acid (0.62 g, 3.56 mmol). The mixture was refluxed with removal of water using a Dean-Stark apparatus for approximately 3 hrs. The mixture was concentrated under reduced pressure and the resulting oil was used in next step without further purification.

Step 3: Synthesis of Compound 5

Compound 4 (3 g, 10.23 mmol) was diluted in methanol (30 ml, 10×Vol) followed by the addition of (S) α-methyl benzylamine (3.7 g, 30.7 mmol) at room temperature. The mixture was stirred at 20-25° C. for 5 days. The mixture was concentrated under reduced pressure to remove methanol. The resulting oil was dissolved in water and its pH was adjusted to pH 10 with 0.3 M K$_2$CO$_3$. The mixture was washed with EtOAc, then the product containing aqueous layer was acidified with 35% HCl to pH=2-3. The resulting suspension was filtered and the solid was dried in oven under vacuum to give compound 5 in a yield of 73% (in two steps from compound 3). LC-MS m/e calc. 385.2 (M+1); found 385.4. $^1$H NMR (DMSO-d$_6$): δ (ppm) 1.34 (d, J=6.97 Hz, 3H), 1.64-1.90 (m, 2H), 2.17 (t, J=8.24 Hz, 2H), 3.98-4.10 (m, 1H), 4.84-4.93 (m, 1H), 5.05 (s, 2H), 7.17-7.26 (m, 1H), 7.28-7.40 (m, 10H), 8.36 (d, J=8.14 Hz, 1H), 12.11 (broad s, 1H).

Step 4: Synthesis of Compound 6

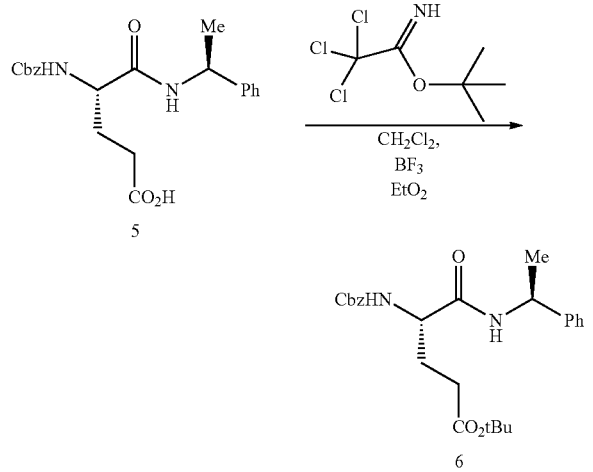

A suspension of compound 5 (0.1 g, 0.26 mmol) and tert-butyl 2,2,2,-trichloroacetimide (0.38 g, 1.71 mmol) in DCM (2 ml) was cooled to 0° C. BF$_3$ etherate (0.02 ml, 0.015 mmol) was added to the mixture. The reaction was warmed to room temperature and stirred for 2 hr. The reaction was quenched with 10% aqueous K$_2$CO$_3$. The product containing organic layer was washed with 10% aqueous K$_2$CO$_3$ then water. The organic layer was concentrated under reduced pressure to yield compound 6. LC-MS m/e calc. 441.2 (M+1); found 441.4. $^1$H NMR (DMSO-d$_6$): δ (ppm) 1.33 (s, 3H), 1.37 (s, 9H), 1.64-1.85 (m, 2H), 2.14 (t, J=8.10 Hz, 2H), 4.00-4.08 (m, 1H), 4.84-4.94 (m, 1H), 5.07 (s, 2H), 7.19-7.24 (m, 1H), 7.26-7.36 (m, 10H), 8.37 (d, J=9.0 Hz, 1H).

Step 5: Synthesis of Compound 1

Compound 6 is converted to Compound 1 using a hydrogen source, such as H$_2$, and a catalyst, such as Pd/C (palladium on carbon), optionally followed by treatment with HCl.

Example 2

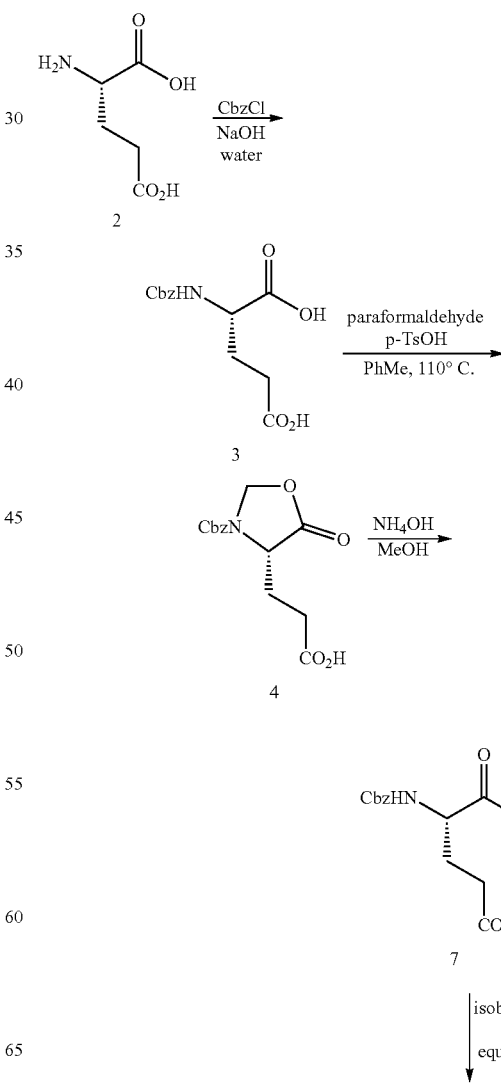

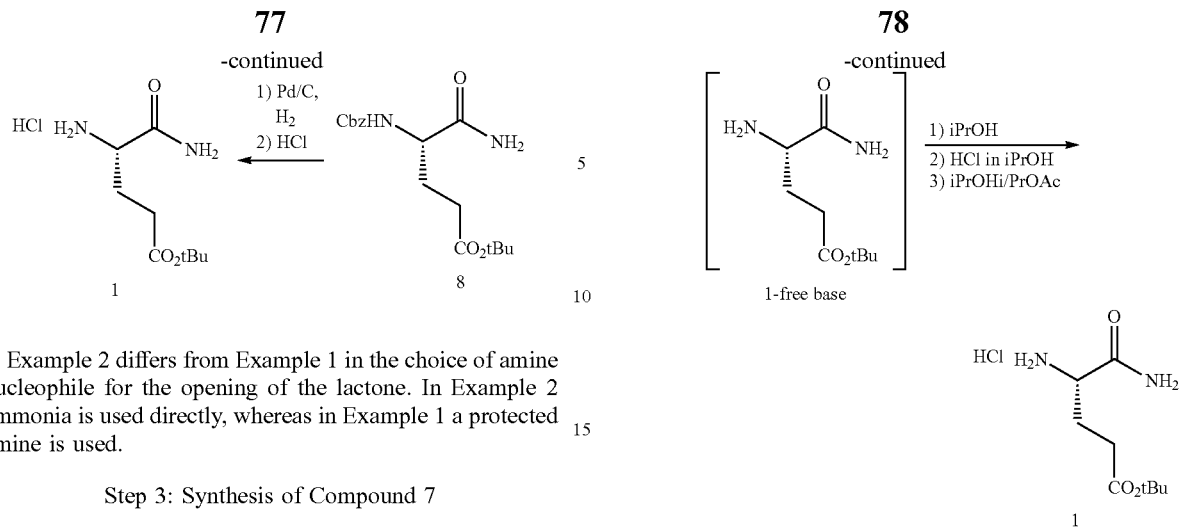

Example 2 differs from Example 1 in the choice of amine nucleophile for the opening of the lactone. In Example 2 ammonia is used directly, whereas in Example 1 a protected amine is used.

Step 3: Synthesis of Compound 7

To the methanol solution (20 ml) of compound 4 (1.1 g, 3.75 mmol) was added ammonium hydroxide (20-30% by weight, 10 ml, 20 eq) at 20 to 25° C. The mixture was stirred at 20-25° C. for 5 days. The mixture was concentrated under reduced pressure to remove methanol. The resulted oil was dissolved in water. The mixture was washed with EtOAc, followed by acidification of the aqueous layer with 35% HCl to pH=2-3. The acidified mixture was extracted with EtOAc (20 ml×3). The organic layer was dried over MgSO$_4$, concentrated on rota-yap. The resulted solid was dried in oven under vacuum to give compound 7. LC-MS m/e calc. 281.1 (M+1); found 281.2. $^1$H NMR (DMSO-d$_6$): δ (ppm) 1.65-1.78 (m, 1H), 1.82-1.95 (m, 1H), 2.24 (t, J=7.9 Hz, 2H), 3.90-3.98 (m, 1H), 5.06 (s, 2H), 7.07 (s, 1H), 7.30-7.37 (m, 7H), 12.10 (broad s, 1H).

Example 2A

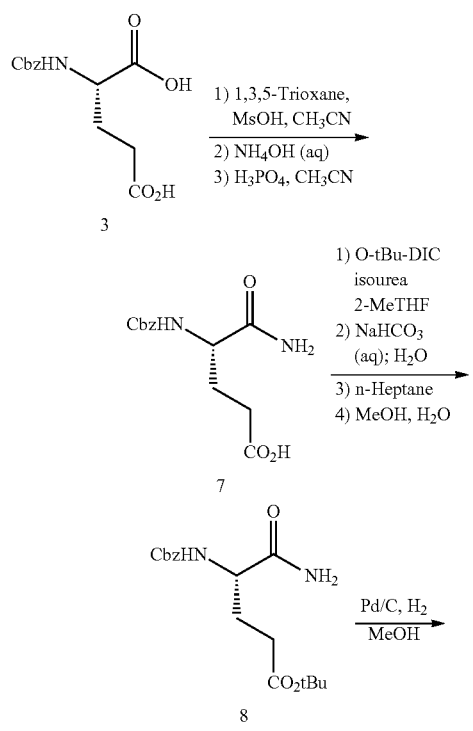

Step 1: Synthesis of Compound 7

Compound 3, 1,3,5-trioxane, methane sulfonic acid (MsOH) and acetonitrile (CH$_3$CN) were charged to a reactor and warmed. The batch was then transferred to ammonium hydroxide (NH$_4$OH, aq.) in water and agitated to form the ammonium salt of compound 7, which was filtered and isolated. The ammonium salt of compound 7 was charged back to a reactor, followed by the addition of acetonitrile, water, phosphoric acid (H$_3$PO$_4$), and compound 7 seeds. The resulting compound 7 slurry was filtered, washed with acetonitrile/water, and dried to afford final compound 7.

Step 2: Synthesis of Compound 8

Compound 7 and 2-methyltetrahydrofuran (2-MeTHF) were charged to a reactor, followed by O-t-Bu-DIC isourea (formed separately by reacting diisopropylcarbodiimide with t-butanol and CuCl and oxygen). The reaction was warmed to form compound 8. After reaction completion, non-product containing solids were removed by filtration, the batch was washed with sodium bicarbonate solution (NaHCO$_3$) and water, distilled with fresh 2-MeTHF to reduce the water content, and crystallized by charging n-heptane and, optionally, compound 8 seeds. Crude compound 8 was filtered, washed with n-heptane and 2-MeTHF, and dried under reduced pressure.

Crude compound 8 was charged back to a reactor, methanol (MeOH) was charged, the batch was heated to dissolution. Water and compound 8 seeds were charged to induce crystallization, followed by additional water. The resulting pure compound 8 was filtered, washed with water/methanol, and dried under reduced pressure to yield compound 8.

Step 3: Synthesis of Compound 1

Compound 8, Pd/C, and methanol were charged to a reactor. The atmosphere was exchanged to hydrogen (H$_2$), and the reaction was warmed to afford free base compound 1. Upon reaction completion the batch was filtered to remove Pd/C. The batch was optionally treated with a solid phase or phosphine based solution palladium scavenger.

The batch was solvent exchanged to isopropanol (iPrOH), a portion of HCl in iPrOH and compound 1 seeds were charged to induce crystallization, followed by charging additional HCl in iPrOH to fully form the salt. Isopropyl acetate (iPrOAc) was charged to desaturate. The batch was filtered, washed with iPrOH/iPrOAc, and dried under reduced pressure to afford compound 1.

Example 2B

Step 1: Synthesis of Compound 7

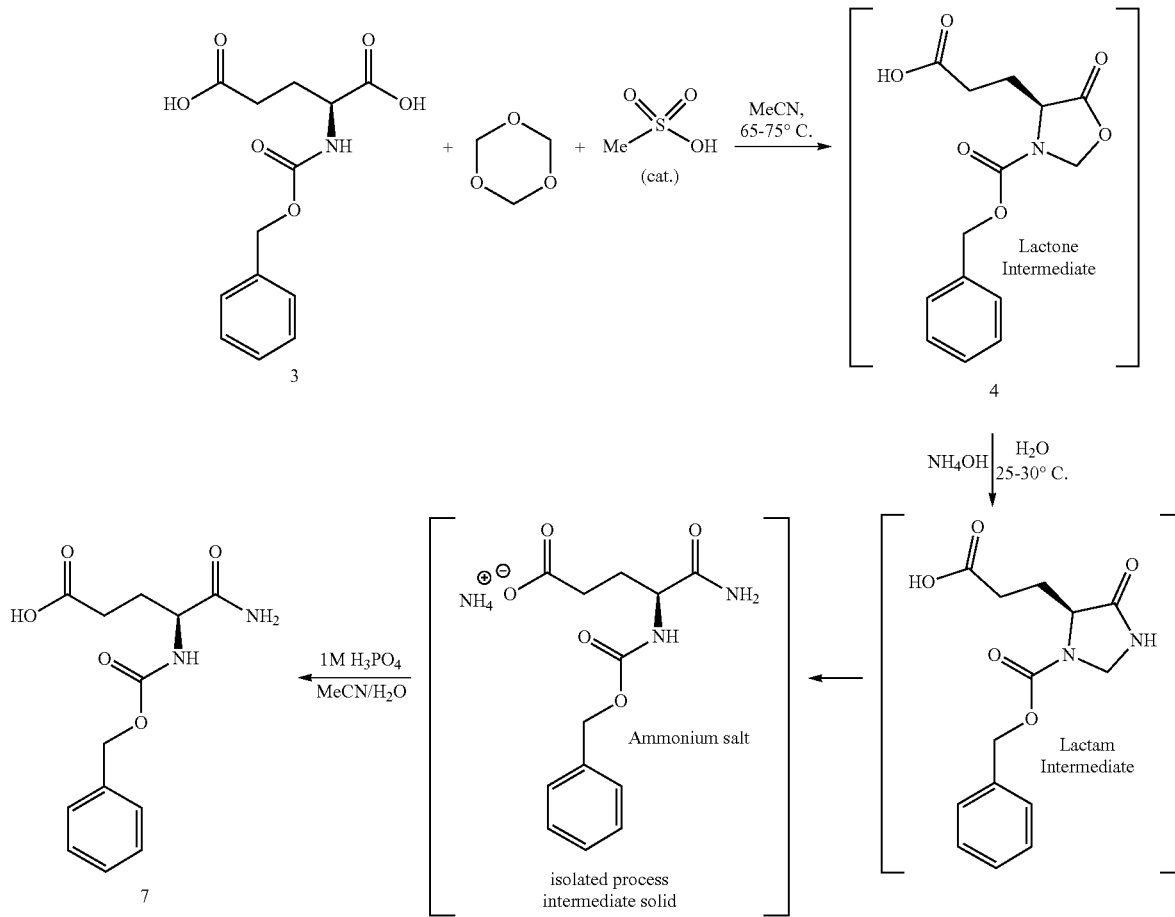

Compound 3 (250 g, 1.00×wt), 1,3,5-trioxane (96.0 g, 0.384×wt), and MeCN (2 L, 8×vol) were charged to reactor 1. 2×vol to 20× volume MeCN can be used. Alternative formaldehyde sources to 1,3,5-trioxane, such as paraformaldehyde, can be used. Methanesulfonic acid (7.5 ml, 0.030× vol) was charged to reactor 1. Alternative charges from 0.01 to 0.1×vol can be used. Alternative acids, such as benzenesulfonic acid, p-toluenesulfonic acid, trifluoromethanesulfonic acid, trifluoroacetic acid, sulfuric acid, or trichloroacetic acid, can be used. The reaction mixture was agitated and heated to 70° C. for 12 hours. 60 to 80° C. can be used. 6 hours to 36 hours can be used.

MeCN (2 L, 8×vol) and 23-30% aq. NH$_4$OH (365 mL, 1.46×vol) were charged to reactor 2. 4 to 20×volume MeCN can be used. A different ammonia source, such as gaseous ammonia, can be used.

The lactone solution in reactor 1 was added over 4 hr to the ammonia solution in reactor 2, maintaining a temperature of about 20° C. An addition time of 0.5 to 24 hours can be used. A temperature of 10 to 50° C. can be used. The batch in reactor 2 was then heated to about 30° C. for 13 hrs. A temperature of 10 to 50° C. can be used. A time of 2 to 48 hrs can be used. The resulting slurry in reactor 2 was cooled to about 20° C. A temperature of 4 to 30° C. can be used. The slurry in reactor 2 was filtered, and washed with MeCN (0.85 L, 3.4×vol). A wash volume of 0 to 10×MeCN can be used. The resulting ammonium salt was dried under vacuum at 35° C. A temperature of 10 to 50° C. may be used. A nitrogen sweep may be used during drying.

The ammonium salt was charged to reactor 3, along with MeCN (563 mL, 2.25×vol) and H$_2$O (680 mL, 2.72×vol). 1 to 5×volumes of MeCN can be used. 1 to 5×volumes of water can be used. 1M H$_3$PO$_4$ (250 mL, 1.00×vol) was charged over at least 0.5 hr, maintaining a temperature of 25° C. Concentrations of 0.1 to 14.8 M phosphoric acid can be used. The phosphoric acid can be charged from 0.1 hour to 12 hours. A temperature of 10 to 40° C. can be used. Different acids from phosphoric acid can be used such as other mineral acids (HCl, H$_2$SO$_4$), or organic acids (citric acid, tartaric acid).

Final product seeds (0.63 g, 0.0025×wt) were charged. 0 to 50 wt % seeds can be used. The thin slurry was aged for 1 h at 20° C. Batch can be aged for 0.5 to 12 hours. The temperature can be from 0 to 30° C. 1M H$_3$PO$_4$ (550 mL, 2.20×vol) was charged over 10 hr at 20° C. Concentrations of 0.1 to 14.8 M phosphoric acid can be used. The phosphoric acid can be charged from 2 hours to 24 hours. A temperature of 10 to 40° C. can be used. Different acids from phosphoric acid can be used such as other mineral acids (HCl, $H_2SO_4$), or organic acids (citric acid, tartaric acid). The slurry in reactor 3 was aged for 1 hr. The batch can be aged for 0 to 24 hours. The slurry was filtered. The cake was washed with $MeCN:H_2O$ (1:2.5 volume ratio, 1 L, 4.00× vol). Different solvent ratios and volumes may be used. The cake was dried under vacuum at 35° C. to provide compound 7 (yield 168 to 175 g, 67-70% molar yield). A temperature of 10 to 50° C. may be used. A nitrogen sweep may be used during drying.

The crystallization process described above is capable of upgrading the chiral purity of compound 7. In one example, a reaction starting with compound 3 with 98.14% chiral purity (1.86% of the D/R enantiomer), yields the product compound 7 with 99.80% chiral purity (0.2% of the R enantiomer of compound 7).

Analytical Data for compound 7: HPLC purity: 99.09%. HPLC chiral purity: 100.0%. $^1H$ NMR (DMSO-$d_6$, 300 MHz): δ=7.36-7.30 (m, 7H), 7.03 (s, 1H), 5.02 (s, 2H), 3.93 (ddd, J=8.7, 5.1 Hz, 1H), 2.23 (t, J=7.8 Hz, 2H), 1.94-1.83 (m, 1H), 1.78-1.65 (m, 1H). $^{13}C$ NMR (DMSO-$d_6$, 75 MHz): δ=173.9, 173.4, 155.9, 137.0, 128.3, 127.7, 127.6, 65.4, 53.9, 30.3, 27.2. MS Analysis: Calculated: [M+1]=281.28; Found: [M+1]=281.2. CHN Analysis: Calculated: C: 55.71%; H: 5.75%; N: 10.00%; Found: C: 55.46%, H: 5.75%, N: 10.00%.

One crystalline form was identified for Compound 7 and is designated as Form A of compound 7. The form was characterized by XRPD and DSC, and representative results are provided in FIG. 1 (XRPD) and FIG. 2 (DSC), This synthetic route can be used to make the racemic Compound 7 by starting with racemic: starting material, or by racemizing the stereogenic center. One crystalline form was identified for racemic Compound 7 and is designated as Form A of racemic compound 7. The form was characterized by XRPD and DSC, and representative results are provided in FIG. 3 (XRPD) and FIG. 4 (DSC).

Step 2: Synthesis of Compound 8

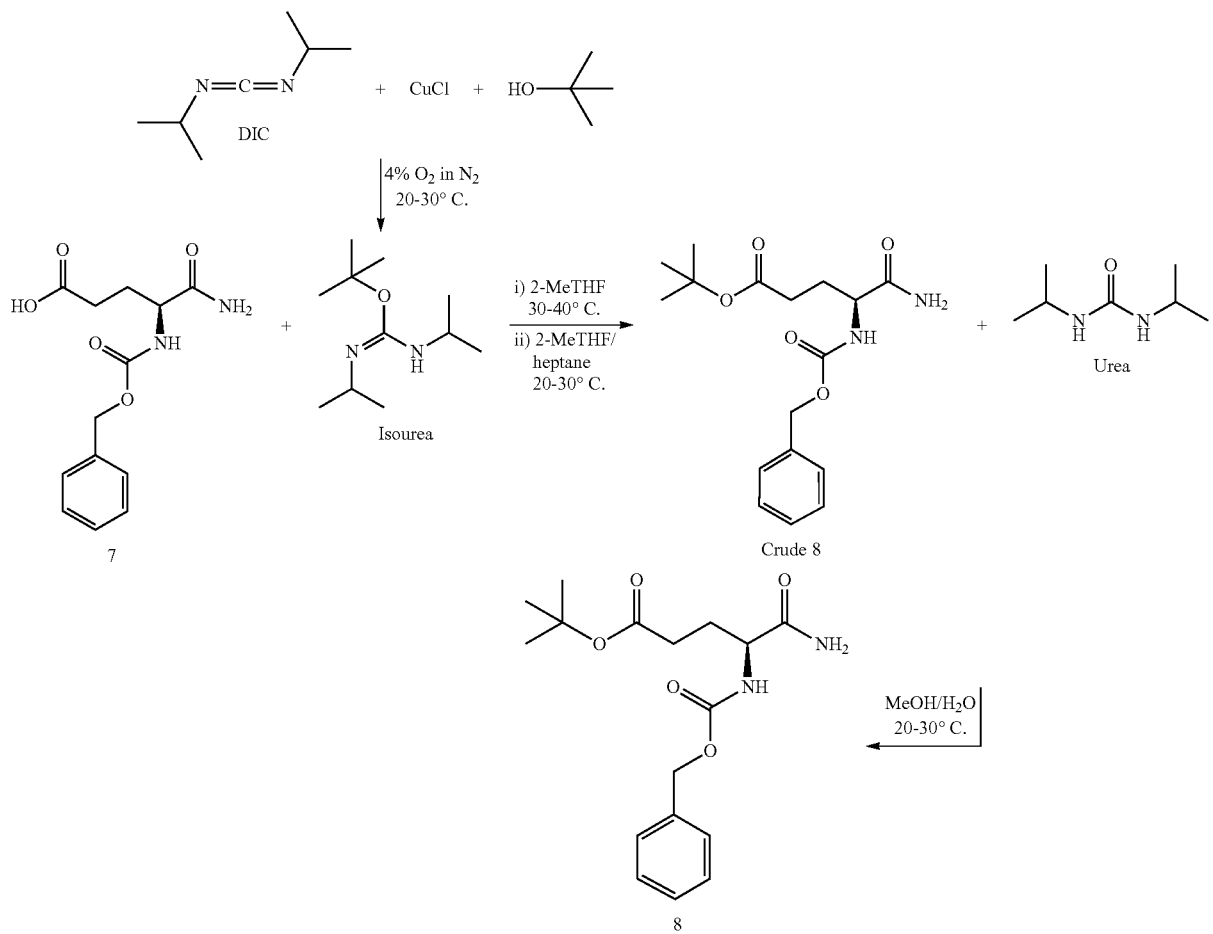

Isourea reagent preparation: CuCl (2.02 g, 0.02×wt) was charged to reactor 1. A charge of 0.01 to 0.10×wt CuCl can be used. Alternative Cu(I) salts such as CuBr or CuI can be used. N,N'-diisopropylcarbodiimide (126.8 mL, 1.27×vol) was charged to reactor 1. Alternative initial charges of N,N'-diisopropylcarbodiimide can be used (0 to 3.17×vol). A 4% 02 atmosphere was established in reactor 1. An atmosphere of up to 22% $O_2$ can be used. The reaction mixture was agitated at 25° C. for 1 hour while maintaining a vessel atmosphere of 4% 02. A temperature of 10 to 40° C. can be used. A vessel atmosphere of up to 22% $O_2$ can be used. An agitation time of 0 to 12 hours can be used. N,N'-diisopropylcarbodiimide (190.2 mL, 1.9×vol) was charged to reactor 1 while maintaining a temperature of ≤30° C. Alternative secondary charges of N,N'-diisopropylcarbodiimide can be used (0 to 3.17×vol). A temperature of 10 to 40° C. could be used. Tert-butanol (182 g, 1.82×wt) was charged to reactor 1 while maintaining a temperature of ≤30° C. Alternative charges of tert-butanol (1.51 to 3.02×wt) can be used. A temperature of 10 to 40° C. can be used. A 4% $O_2$ atmosphere was re-established and reactor 1 was sealed. A vessel atmosphere of up to 22% $O_2$ can be used. Reactor 1 was agitated at 25° C. for 12 hours while maintaining a vessel atmosphere of 4% $O_2$. A vessel atmosphere of up to 22% $O_2$ can be used. A temperature of 10 to 40° C. can be used. A reaction time of 4 to 72 hours can be used.

Esterification: Compound 7 (100 g, 1×wt) and 2-MeTHF (1 L, 10×vol) were charged to reactor 2. 6 to 20×volumes 2-MeTHF can be used. Alternative solvents including THF, DCM, MTBE, 1,4-dioxane, $Et_2O$, etc. can be used. Isourea (386 mL, 3.86×vol) was charged to reactor 2 over 2 h, maintaining ≤40° C. Alternative charges from 0.96 to 7.72×vol isourea can be used. The isourea can be charged over 1 to 12 hours. 10 to 40° C. can be used. Contents of reactor 2 were agitated and heated to 35° C. for 5 hrs. 10 to 50° C. can be used. 2 to 48 hrs can be used. Water (0.01 to 1×vol) is optionally charged. Celite (30 g, 0.3×wt) was charged to reactor 2. 0 to 1×wt celite can be used. The batch was filtered into reactor 3 and washed twice with 2-MeTHF (400 mL, 4×vol per wash). A wash volume of 0 to 8×volumes can be used. 0 to 3 washes can be used. The batch was washed twice with sodium bicarbonate solution (300 mL, 3×vol per wash). A wash volume of 0 to 6×volumes per wash can be used. 0 to 3 washes could be used. The batch was washed with water (300 mL, 3×vol). A wash volume of 0 to 6×volumes per wash can be used. 0 to 2 washes can be used. 2-MeTHF was distilled off under reduced pressure to 10×vol. A temperature of 25 to 55° C. can be used. A pressure of 150 to 500 torr can be used. An endpoint volume of 6 to 14×vol 2-MeTHF can be used. Distillation continued at 10×vol with addition of 4×vol 2-MeTHF. A temperature of 25 to 55° C. can be used. A pressure of 150 to 500 torr can be used. A total volume of 6 to 14×vol 2-MeTHF can be used. Addition of 0 to 12×2-MeTHF could be used. Distillation continued under reduced pressure to 5×vol. A temperature of 25 to 55° C. can be used. A pressure of 150 to 500 torr can be used. An endpoint of 4 to 8×vol 2-MeTHF can be used. The batch was cooled to 25° C. and n-heptane (50 mL, 0.5×vol) was charged. A temperature of 10 to 30° C. can be used. A charge of 0 to 2×volume n-heptane can be used. The slurry was aged for 0.5 hrs. The slurry can be aged for 0.5 to 12 hour. The batch was seeded with product seeds (0.25 g, 0.0025× wt). 0 to 50 wt % seeds can be used. The slurry was aged for 2 hr. The slurry can be aged for 0 to 24 hours. n-Heptane (1.5 L, 15×vol) was charged to reactor 3 over 8 hrs. The n-heptane can be charged from 2 hours to 24 hours. A temperature of 10 to 40° C. can be used. The slurry was aged for 3 hrs. The batch can be aged for 0 to 24 hours. The slurry was filtered in reactor 3, and was subjected to slurry wash with 2-MeTHF/n-heptane (1:3 volume ratio, 400 mL, 4×vol) and displacement wash with 2-MeTHF/n-heptane (1:3 volume ratio, 400 mL, 4×vol). Different solvent ratios and volumes may be used. The crude product Compound 8 was dried under vacuum at 35° C. A temperature of 10 to 50° C. can be used. A nitrogen sweep can be used during drying.

Recrystallization of crude product: Crude product Compound 8 (85 g, 1×wt) and MeOH (595 mL, 7×vol) were charged to reactor 4. 6 to 10×volumes MeOH can be used. Water was charged (85 mL, 1×vol) to reactor 4 over 1 hr. 0.6 to 3.0×volumes 2-MeTHF could be used. Product seeds (0.212 g, 0.0025×wt) were charged to reactor 4. 0 to 50 wt % seeds can be used. The slurry was aged in reactor 4 for 1 hr. The slurry can be aged for 0.5 to 12 hours. Water (510 mL, 6×vol) was charged to reactor 4 over 6 hrs. The water can be charged from 2 hours to 24 hours. A temperature of 10 to 30° C. could be used. The slurry was aged for 3 hrs. The batch can be aged for 0 to 24 hours. The slurry in reactor 4 was filtered and washed with $MeOH/H_2O$ (1:1 volume ratio, 340 mL, 4×vol). Different wash solvent ratios and volumes can be used. The product was dried under vacuum at 35° C. to provide Compound 8 (yield 66-78 g, 55-65% molar yield). A temperature of 10 to 50° C. can be used. A nitrogen sweep can be used during drying.

This process is capable of starting with a Compound 7 with 97.2% chiral purity (2.8% of the enantiomer of Compound 7) to produce Compound 8 with 99.9% chiral purity (0.1% enantiomer of Compound 8) via the crystallization.

Analytical data for Compound 8: HPLC purity: 99.46%. HPLC chiral purity: 99.97%. $^1$H NMR (DMSO-$d_6$, 300 MHz): δ=7.36-7.30 (m, 7H), 7.05 (s, 1H), 5.07-5.02 (m, 2H), 3.93 (ddd, J=8.7, 5.1 Hz, 1H), 2.22 (t, J=7.8 Hz, 2H), 1.94-1.82 (m, 1H), 1.76-1.64 (m, 1H), 1.38 (s, 9H). $^{13}$C NMR (DMSO-$d_6$, 75 MHz): δ=173.8, 172.1, 156.4, 137.5, 128.8, 128.2, 128.1, 80.1, 65.9, 54.2, 31.9, 28.2, 27.7. MS Analysis: Calculated: [M+1]=337.17; Found: [M+1]=337.1. CHN Analysis: Calculated: C: 60.70%; H: 7.19%; N: 8.33%; Found: C: 60.86%, H: 7.06%, N: 8.30%.

One crystalline form was identified for Compound 8 and is designated as Form A of compound 8. The form was characterized by XRPD and DSC, and representative results are provided in FIG. 5 (XRPD) and FIG. 6 (DSC).

This synthetic route can be used to make the racemic Compound 8 by starting with racemic starting material, or by racemizing the stereogenic center. One crystalline form was identified for racemic Compound 8 and is designated as Form A of racemic compound 8. The form was characterized by XRPD and DSC, and representative results are provided in FIG. 7 (XRPD) and FIG. 8 (DSC).

Step 3: Synthesis of Compound 1

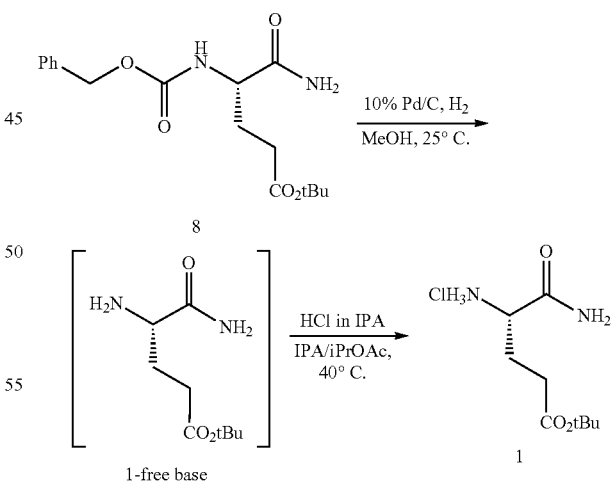

Compound 8 (10.0 g, 1×wt), 10% Pd/C (0.250 g, 0.025× wt) and MeOH (100 mL, 10×vol) were charged to reactor 1. 2× to 20× volume MeOH can be used. Alternate alcohol solvents in addition to MeOH can include ethanol, isopropanol, 1-propanol, butanol. Solvents can also include THF, 2-MeTHF, MTBE, isopropyl acetate, ethyl acetate, DMF, DMAc or NMP. 5% to 10% Pd/C can be used. In addition, it can be used dry or water wet. Catalysts can include, Palladium, Platinum, Rhodium or Ruthenium on different supports that encompass carbons, alumina, alkaline earth carbonates, clays, ceramics and celite. Catalyst loading can range from 1 wt % to 100 wt %.

The batch was purged 3 times with $N_2$ followed 3 times with $H_2$. Batch can be purged 1 to 10 times with $N_2$ and $H_2$. The batch was pressurized to 15 psi $H_2$. Batch can be pressurized with $H_2$ from 15 psi to 60 psi. Transfer hydrogenation conditions can be utilized that include cyclohexene, cyclohexadiene, formic acid, and ammonium formate. The batch was heated to 20 to 30° C. (target 25° C.). Batch temperature can range from 15° C. to 60° C. The batch was agitated at 20 to 30° C. (target 25° C.) for NLT 4 h. Reaction times between 1 h and 36 h can be used. Reaction completion was determined by in-process control (IPC).

The batch was filtered over celite (4.0 g, 0.4×wt, prewetted with MeOH) followed by a 1 uM in-line filter or smaller into reactor R-2. Varying amounts of celite can be used from no celite to 100 wt % celite. Reactor 1 was washed with 2×vol (20 mL) MeOH and filtered over celite pad through 1 uM in-line filter or smaller into reactor R-2. Alternate wash volumes from 0 to 10×vol can be used. The celite pad was washed with 2×vol (20 mL) MeOH through a 1 uM in-line filter or smaller into reactor R-2. Alternate wash volumes from 0 to 10×vol can be used. The batch was heated to 35 to 45° C. (target 40° C.). Alternate temperatures between 22 to 65° C. can be used. The batch was distilled to 5×vol under reduced pressure maintaining a temperature between 30 and 45° C. Batch can be distilled to dryness or any volume between 1× and 8×vol. Temperatures between 20 and 83° C. can be used. The batch was subject to constant volume distillation under reduced pressure with 12×vol (120 mL) IPA maintaining a temperature between 30 and 45° C. and a batch volume of 5× (50 mL). Constant volume distillation is not required. Batch can be distilled to dryness and then refilled with IPA. Temperatures between 20 and 83° C. can be used. 3×vol (30 mL) Isopropyl acetate was charged, maintaining a temperature between 35 and 45° C. Isopropyl acetate charge can vary between 1× and 5×vol. Other solvents can be used as antisolvents including, MeCN, toluene, MTBE, ethyl acetate, heptanes, and acetone. 0.025× vol (0.250 mL) trioctylphosphine was charged. Charge can vary between 0.01×vol to 1.0×vol. Alternate Pd scavengers can be used that include activated carbons, silica supported resins, and polymer supported resins and fibers. Alternative alkyl phoshpines can be used include, triethylphosphine, tributyl phosphine, trihexylphosphine. The process can be run without a palladium scavenger.

HCl in IPA (0.065×vol (0.650 mL) or 0.1 equiv) was charged dropwise. Different concentrations of HCl in IPA can be used from 1 M to 6M. A different mineral or organic acid, such as benzenesulfonic acid, sulfuric acid, hydrobromic acid, or acetic acid could be used to make a different salt. The batch was seeded with 0.01×wt (100 mg) of Compound 1 seeds. 0 to 50 wt % seed can be used. The slurry was aged at 35 to 45° C. (target 40° C.) for NLT 1 h. Slurry can be aged from 0 to 24 h. HCl in IPA (0.52×vol (5.2 mL) or 0.8 equiv) was charged dropwise over NLT 3 h maintaining a temperature between 35 and 45° C. Different concentrations of HCl in IPA can be used from 1 M to 6M. Charge time can be varied from 5 min to 24 h. The batch was held at 35 to 45° C. (target 40° C.) for 30 min. Hold times can vary from 0 min to 24 h. The batch was cooled to 20 to 25° C. over NLT 2 h. Temperature ramp from 0.5 h to 12 h can be used. HCl in IPA (0.065×vol (0.650 mL) or 0.1 equiv) was charged dropwise over 30 min. Different concentrations of HCl in IPA can be used from 1 M to 6M. HCl addition times may vary from 5 min to 24 h. The slurry was aged at 20 to 25° C. for NLT 1 h. Batch can be aged from 0 h to 24 h. The slurry was filtered over Filter F-2. The cake was washed two times with 2×vol (20 mL) 1:1 IPA/iPrOAc. Different solvent volumes and ratios may be used. The product was dried under vacuum between 20-40° C. to provide Compound 1. A temperature of 10 to 50° C. can be used. A nitrogen sweep can be used during drying.

Compound 8 containing 2.27% of the R-enantiomer can be upgraded to Compound 1 with a chiral purity of greater than 99.9% by this process.

Analytical data for Compound 1: HPLC purity: 99.12%. HPLC chiral purity: 99.98%. $^1$H NMR (DMSO-$d_6$, 300 MHz): δ=8.38 (broad s, 1H), 8.07 (s, 1H), 7.55 (s, 1H), 3.77 (t, J=6.3 Hz, 1H), 2.32-2.29 (m, 2H), 1.99-1.91 (m, 2H), 1.39 (s, 9H). $^{13}$C NMR (DMSO-$d_6$, 75 MHz): δ=171.5, 170.4, 80.5, 51.8, 30.8, 29.7, 28.2, 26.6. MS Analysis: Calculated: [M+1] (free base)=203.17; Found: [M+1] (free base)=203.1.

Two crystalline forms were identified for Compound 1 and are designated as Form A and Form B of compound 1. Form A was obtained from isopropanol/isopropylacetate system. Form A was characterized by XRPD and DSC, and representative results are provided in FIG. 9 (XRPD) and FIG. 10 (DSC). Form B was obtained from methanol/isopropylacetate system. Form B was characterized by XRPD and DSC, and representative results are provided in FIG. 11 (XRPD) and FIG. 12 (DSC).

This synthetic route can be used to make the racemic Compound 1 by starting with racemic starting material, or by racemizing the stereogenic center. One crystalline form was identified for racemic Compound 1 and is designated as Form A of racemic compound 1. The form was characterized by XRPD and DSC, and representative results are provided in FIG. 13 (XRPD) and FIG. 14 (DSC).

Example 3

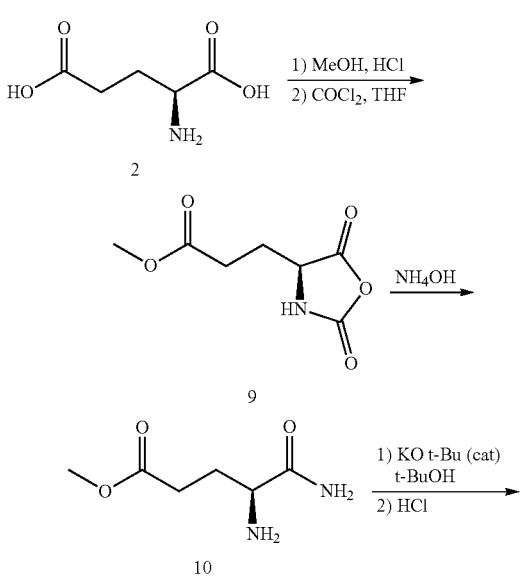

The reaction of L-glutamic acid 2 with methanol in the presence of HCl followed by phosgenation reaction provides compound 9. The subsequent addition of ammonia (as a solution in water or a solvent such as methanol) forms amide 10. Conversion of methyl ester to tert-butyl ester is achieved by catalytic potassium tert-butyloxide in tert-butanol. Lastly, formation of HCl salt of the amino-amide provides the target molecule 1.

Example 4

The reaction of L-glutamic acid 2 with isobutylene in THF in the presence of catalytic $BF_3 \cdot Et_2O$ and $H_3PO_4$ provides 5-tert-butyl ester compound 11. The formation of N-carboxylate anhydride 12 is conducted using phosgene or N,N'-carbonyldiimidazole (CDI). The subsequent addition of ammonia (as a solution in water or a solvent such as methanol) provides free base amide 1. Lastly, formation of HCl salt of the free base amino-amide provides the target molecule 1.

Example 5

Step 1: Synthesis of Compound 14

The reaction of pyroglutamic acid 13 with triethylamine (or other amine base) followed by isobutylchloroformate (or other such chloroformate derivative) provides a mixed carbonate intermediate and the subsequent addition of ammonia (as a solution in water or a solvent such as methanol) to this species forms primary amide 14. Amide 14 is also prepared by alternative carboxylic acid activation procedures generally known in the art followed by reaction with an ammonia source.

Step 2: Synthesis of Compound 1

Selective lactam N-protection of 14 (with Boc, Cbz or other such protecting group) renders the oxopyrroldine prone to ring opening by a suitable nucleophile, such as tBuOK, to provide 1-free base after removal of the protecting group. Formation of HCl salt of the free base amino-amide provides the target molecule 1.

Example 6

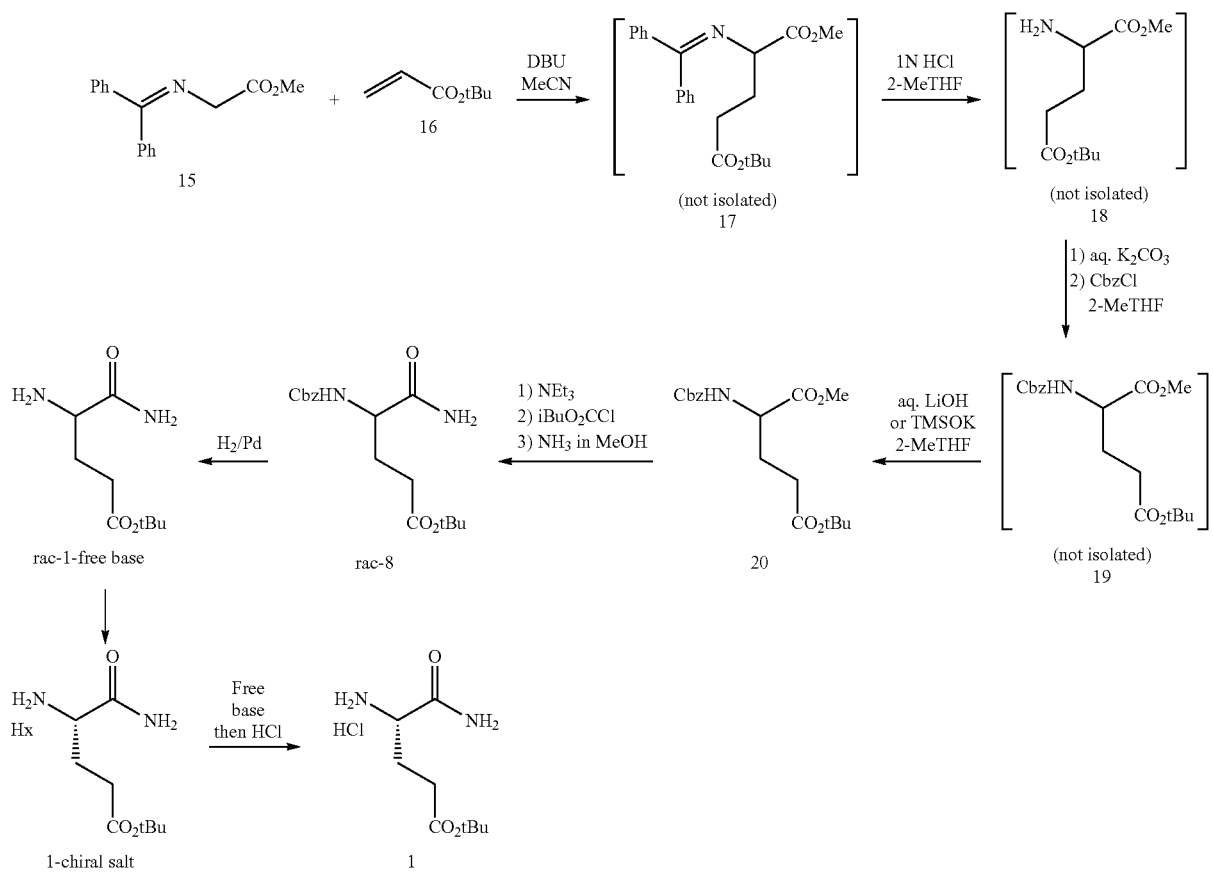

Step 1: Synthesis of Compound 17

To a solution of methyl 2-((diphenylmethylene)amino) acetate 15 (24.6 g) in MeCN (200 mL) was added DBU (1.45 mL) followed by tert-butyl acrylate 16 (17.0 mL). The resulting yellow solution was stirred at room temperature (25° C.). After 24 h it was determined that the reaction had stalled so an additional portion of tert-butyl acrylate 16 (4.26 mL) was added. When the reaction was judged to be complete (~3% SM remaining by LCAP) the solution was concentrated under reduced pressure to ~3×vol (~70 mL) and taken forward to the next step. LCMS for compound 17: LC-MS m/e calc. 382.2 (M+1); found 382.2.

Step 2: Synthesis of Compound 18

To the stirred MeCN solution of compound 17 was added 2-MeTHF (110 mL) and 1N HCl (80 mL). After 5 h at room temperature (25° C.), the phases were split. The organic phase was discarded and the aqueous phase (contains the desired free base 18: (LC-MS m/e calc. 218.1 (M+1); found 218.0) was taken forward to the next step as an aqueous solution.

Step 3: Synthesis of Compound 19

The aqueous phase was adjusted from pH~4 to pH~9 using $K_2CO_3$ (required 86 mL of a 10% aq solution) and 2-MeTHF (105 mL) was added to the solution. Using a syringe pump, benzyl chloroformate (11 mL) was added over 5.5 h and the reaction mixture was reacted for two days at 25° C. The phases were split (aqueous layer ~175 mL, organic layer ~125 mL) and the aqueous layer was discarded. The product containing organic layer (19: LC-MS m/e calc. 352.2 (M+1); found 352.2) was taken forward to the next step as a solution in 2-MeTHF.

Step 4: Synthesis of Compound 20

The crude solution of 19 from previous step was diluted to 150 mL total volume with 2-MeTHF and LiOH (10.65 mL of a 10% aq solution) was added. After 3 h, 9.35 mL of water was added to improve homogeneity of the aqueous layer. Hydrolysis of the methyl ester was monitored by HPLC and the reaction appeared to stall periodically, so additional 0.1 equiv portions of LiOH were added as required. At reaction completion a total of 17.4 mL 10% aqueous LiOH (1.8 equiv) had been added. The solution was adjusted from pH=12 to pH=3 using HCl (required 72 mL of a 1N solution) and the phases split. The organic phase was washed with half-saturated brine solution (2×20 mL) and transferred to a 500 mL round bottom flask. Solvent swap from 2-MeTHF to toluene was performed with azeotropic removal of water via a rotary evaporator. The solution was concentrated to ~5×vol (70 mL) and seeded with 20. A thin seed bed formed over 2 h. Heptane (84 mL) was added over 2 h via syringe pump and agitated for a further 16 hr. The resulting solids were filtered, washed with 1:2 toluene:heptane (60 mL) and dried with vacuum under $N_2$ to yield 20 (13.35 g, 41% over 4 steps) as a white solid. LC-MS m/e calc. 338.2 (M+1); found 338.1. $^1$H NMR (300 MHz, DMSO-d$_6$) δ 1.38 (s, 9H), 1.70-180 (m, 1H), 1.89-2.00 (m, 1H), 2.20-2.40 (m, 2H), 3.97-4.02 (m, 1H), 5.03 (s, 2H), 7.31-7.37 (m, 5H), 7.56-7.59 (d, 1H), 12.6 (s, 1H).

Alternatively, formation of 20 was achieved by reaction of 19 with TMSOK (potassium trimethylsiloxide) (1.0 equiv) in 2-MeTHF.

Step 5: Synthesis of Compound Rac-8

To a solution of 20 (1.00 g) in 2-MeTHF (10 mL) at 0° C. under N$_2$ was added triethylamine (0.413 mL). Isobutyl chloroformate (0.384 mL) was then added dropwise via syringe over 10 minutes. After 10 minutes, ammonia (2.22 mL of a 2M solution in MeOH) was added in one portion and the solution was reacted at 0° C. for 3 h. An additional portion of isobutyl chloroformate (96 µL) was charged to afford >95% conversion. Water (5 mL) was added to quench the reaction, the phases were split and aqueous layer extracted with 2-MeTHF (2×4 mL). The combined organic phases were washed with half-saturated brine solution (2×4 mL). Azetropic removal of water with 2-MeTHF was accomplished on the rotary evaporator and the solution was concentrated to ~10×vol (9.8 mL). Heptane (9.8 mL) was added over 1 h via syringe pump, and after aging for 1 h an additional 5 mL of heptane was added via syringe pump over 1 h. The resulting solids were filtered, washed with 7.5 mL of 3:2 heptane:2-MeTHF and dried for 2 h with vacuum under N$_2$ to yield rac-8 (0.630 g, 63% yield) as a white solid. LC-MS m/e calc. 337.2 (M+1); found 337.1. $^1$H NMR (300 MHz, DMSO-d$_6$) δ 1.40 (s, 9H), 1.62-1.81 (m, 1H), 1.82-1.94 (m, 1H), 2.16-2.30 (m, 2H), 3.47 (s, 2H), 3.85-4.00 (m, 1H), 5.02 (d, 2H), 7.05 (s, 1H), 7.23-7.42 (m, 5H).

Step 6: Synthesis of Compound Rac-1 Free Base

Rac-1-free base is prepared from rac-8 in the presence of a hydrogen and a palladium catalyst.

Step 7: Synthesis of Compound 1-Chiral Salt

The reaction of rac-1-free base with a chiral acid provides 1-chiral salt by selective crystallization from a diastereomeric mixture of salts. Chiral acids for diastereomeric salt formation include tartaric acid, 2,3-dibenzoyl tartaric acid, mandelic acid, camphorsulfonic acid, N-Ac-N-leucine, N-Ac-L-phenylalanine, among others, in a series of organic solvents such as MeOH, IPA, n-propanol, among others.

Step 8: Synthesis of Compound 1

Compound 1 is formed after generation of the free base from 1-chiral salt using a suitable inorganic or organic base, followed by addition of HCl.

Example 7

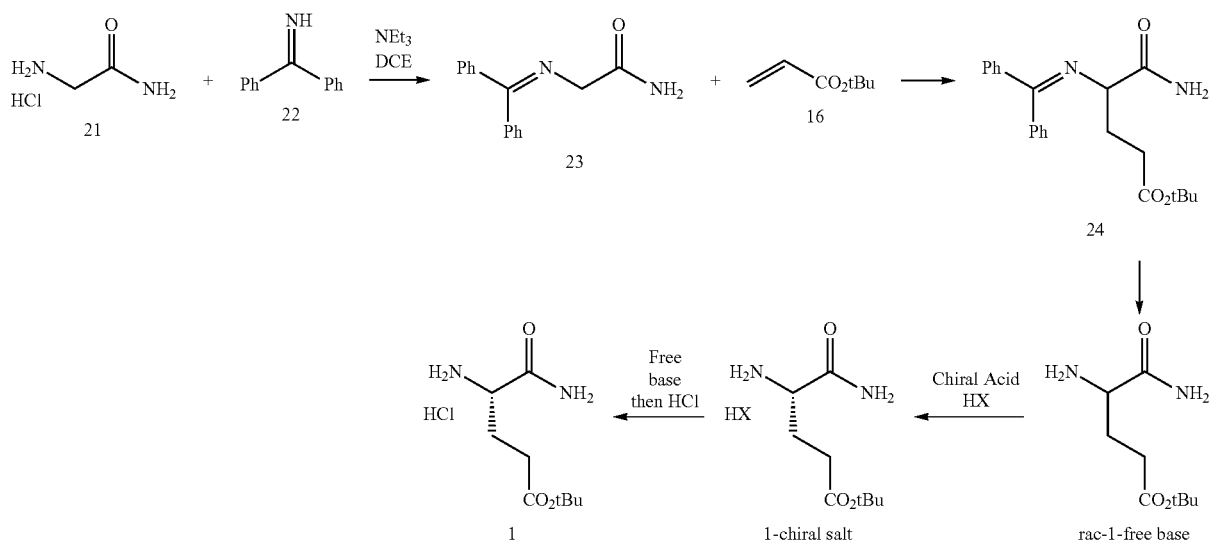

Step 1: Synthesis of Compound 23

2-Aminoacetamide hydrochloride 21 (0.553 g) was weighed into a 20 mL scintillation vial equipped with a stir bar, pressure relief cap and an N$_2$ needle and DCE (3 mL) was added. In a separate vial, triethylamine (0.767 mL) and benzophenone imine 22 (0.839 mL) were dissolved in DCE (3 mL). This solution was transferred to the solution of 21 dropwise via syringe over 10 mins. The combined reaction mixture was heated to 80° C. for 16 h. Cooled to room temperature and precipitated solids were filtered. The crude filtered solids were slurried in heptane/MTBE and stirred overnight at room temperature. The solids were then filtered and dried under vacuum with N$_2$. Collected 0.8184 g of compound 23 LC-MS m/e calc. 239.1 (M+1); found 239.1.

Step 2: Synthesis of Compound 24

Compound 24 is prepared by Michael addition of compound 23 to tert-butyl acrylate 16 in the presence of organic amine bases such as DBU or inorganic bases such as Cs$_2$CO$_3$ and other carbonates.

Step 3: Synthesis of Compound Rac-1-Free Base

Rac-1-free base is prepared by hydrolysis of imine 24 in the presence of an inorganic acid (such as aqueous HCl) or organic acid (such as citric acid or p-toluenesulfonic acid) in a range of solvents including 2-MeTHF or MTBE, among others.

Step 4: Synthesis of Compound 1-Chiral Salt

The reaction of rac-1-free base with a chiral acid provides 1-chiral salt by selective crystallization from a diastereomeric mixture of salts. Chiral acids for diastereomeric salt formation include tartaric acid, 2,3-dibenzoyl tartaric acid, mandelic acid, camphorsulfonic acid, N-Ac-N-leucine, N-Ac-L-phenylalanine, among others, in a series of organic solvents such as MeOH, IPA, n-propanol, among others.

Step 5: Synthesis of Compound 1

Compound 1 is formed after generation of the free base from 1-chiral salt using a suitable inorganic or organic base, followed by addition of HCl.

Example 8

δ 1.39 (s, 9H), 2.18-2.22 (m, 2H), 2.42-2.49 (m, 2H), 4.32 (t, 1H), 7.20-7.24 (m, 2H), 7.33-7.38 (m, 2H), 7.43-7.52 (m, 4H), 7.63-7.66 (m, 2H).

Step 2: Synthesis of Compound 27

Compound 27 is prepared by imine hydrolysis of 26 in the presence of an inorganic acid (such as aqueous HCl) or organic acid (such as citric acid or p-toluenesulfonic acid) in a range of solvents including 2-MeTHF or MTBE, among others.

Step 3: Synthesis of Compound 28

Compound 27 is carried forward without isolation and subjected to reductive amination conditions with benzaldehyde such as sodium triacetoxyborohydride (STAB) or other similar reducing reagents to provide compound 28.

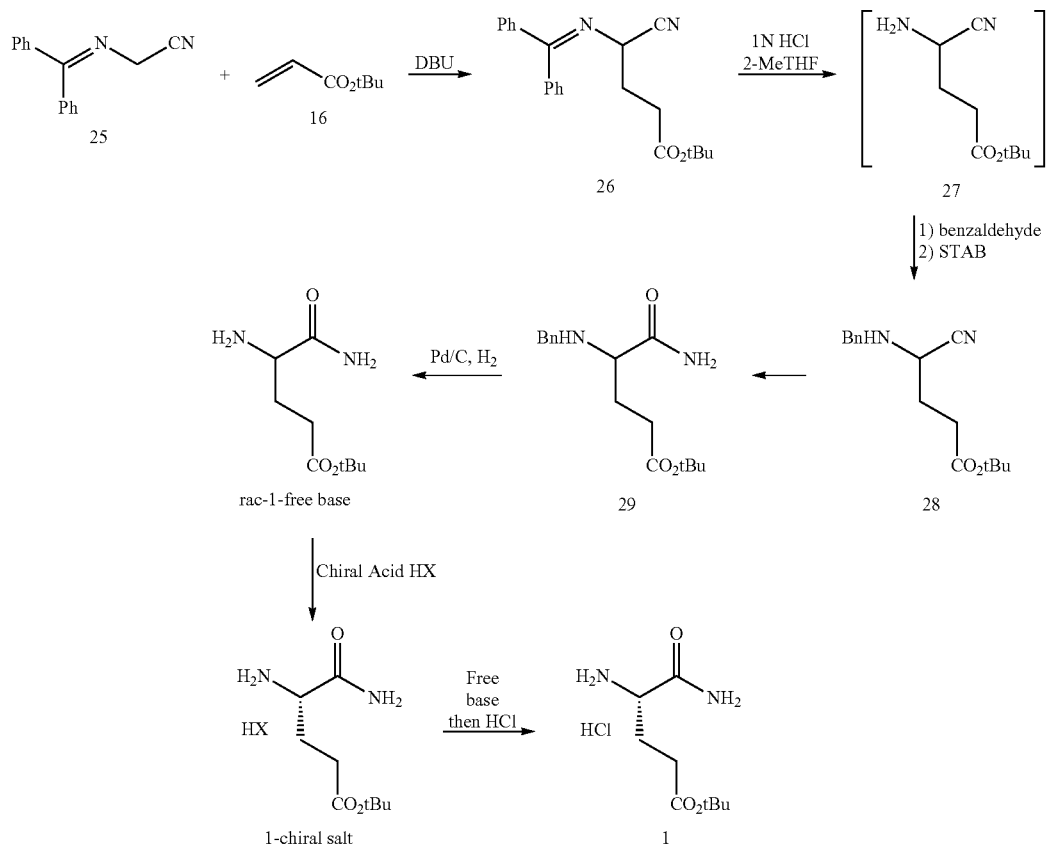

Step 1: Synthesis of Compound 26

To a solution of 2-((diphenylmethylene)amino)acetonitrile 25 (6.4 g) in MeCN (60 mL) was added DBU (0.433 mL) followed by tert-butyl acrylate 16 (6.37 mL). The resulting yellow/orange solution was stirred at room temperature (25° C.). After 16 h, the reaction mixture was concentrated on the rotary evaporator and the desired product 26 was isolated using silica gel chromatography on an ISCO separations module. Compound 26 LC-MS m/e calc. 349.2 (M+1); found 349.2. $^1$H NMR (300 MHz, DMSO-$d_6$)

Step 4: Synthesis of Compound 29

Amide 29 is prepared by hydrolysis of nitrile 28 in the presence of a formaldehyde catalyst and hydroxide base. Alternative nitrile hydrolysis conditions may also be used to provide amide 29.

Step 5: Synthesis of Compound Rac-1-Free Base

Rac-1-free base is prepared by hydrogenation of compound 29 in the presence of a palladium catalyst.

Step 6: Synthesis of Compound 1-Chiral Salt

The reaction of rac-1-free base with a chiral acid provides 1-chiral salt by selective crystallization from a diastereomeric mixture of salts. Chiral acids for diastereomeric salt formation include tartaric acid, 2,3-dibenzoyl tartaric acid, mandelic acid, camphorsulfonic acid, N-Ac-N-leucine, N-Ac-L-phenylalanine, among others, in a series of organic solvents such as MeOH, IPA, n-propanol, among others.

Step 7: Synthesis of Compound 1

Compound 1 is formed after generation of the free base from 1-chiral salt using a suitable inorganic or organic base, followed by addition of HCl.

Example 9

Step 2: Synthesis of Compound 32

Compound 32 is prepared by Michael addition of azlactone 31 to tert-butyl acrylate 16 in the presence of organic amine bases such as DBU or inorganic bases such as $Cs_2CO_3$ or other carbonate base.

Step 3: Synthesis of Compound 33

Compound 33 is prepared by opening of the azlactone ring of compound 32 with the addition of ammonia (as a solution in MeOH or water).

Step 4: Synthesis of Compound Rac-1 Free Base

Rac-1-free base is prepared by removal of the benzoyl protecting group on compound 33.

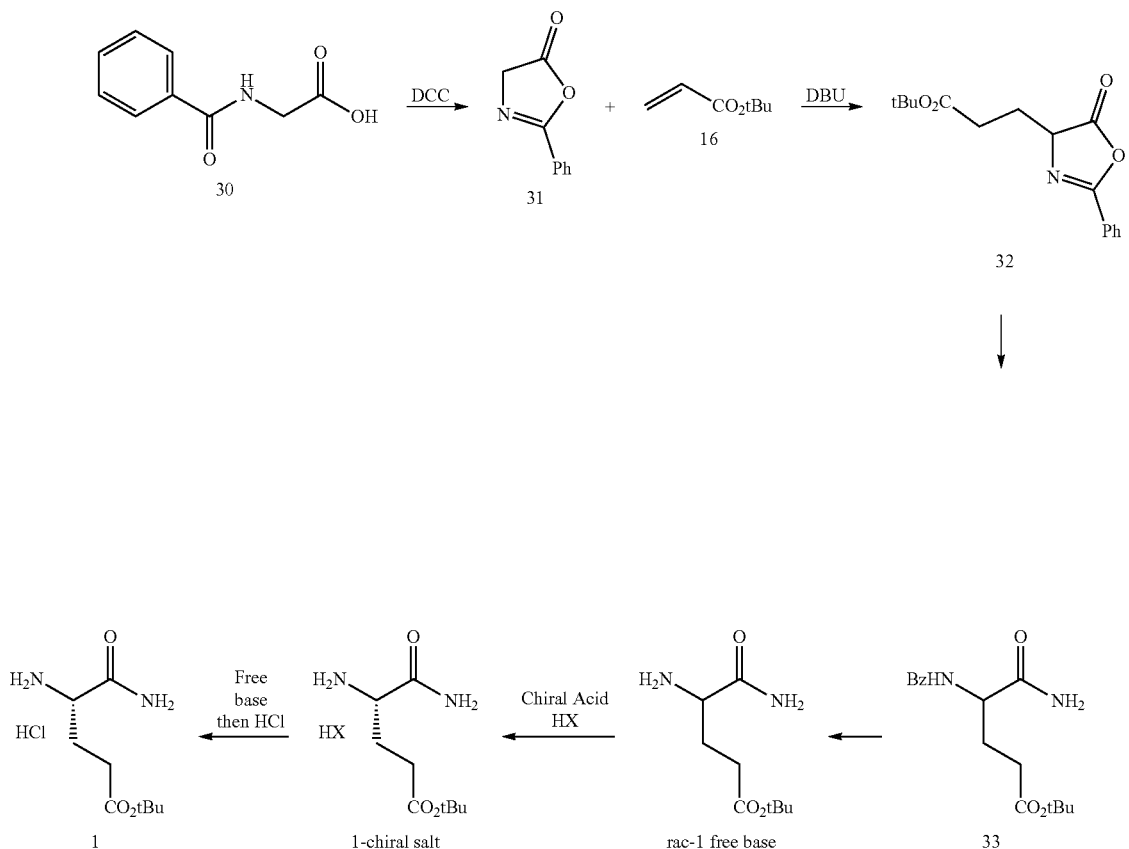

Step 1: Synthesis of Compound 31

To a suspension of hippuric acid 30 (1.08 g) in DCM (25 mL) was added DCC (1.23 g). After 3 h, the mixture was filtered through a short plug of celite and the filtrate was concentrated to an off-white solid on the rotary evaporatory. The crude product was slurried in heptane/EtOAc (3:2) and stirred overnight. Filtered off solids (DCU byproduct) and filtrate was concentrated to yield desired product 31 (0.631 g) as a yellow solid LC-MS m/e calc. 162.1 (M+1); found 162.0.

Step 5: Synthesis of Compound 1-Chiral Salt

The reaction of rac-1-free base with a chiral acid provides 1-chiral salt by selective crystallization from a diastereomeric mixture of salts. Chiral acids for diastereomeric salt formation include tartaric acid, 2,3-dibenzoyl tartaric acid, mandelic acid, camphorsulfonic acid, N-Ac-N-leucine, N-Ac-L-phenylalanine, among others, in a series of organic solvents such as MeOH, IPA, n-propanol, among others.

Step 6: Synthesis of Compound 1

Compound 1 is formed after generation of the free base from 1-chiral salt using a suitable inorganic or organic base, followed by addition of HCl.

Example 10

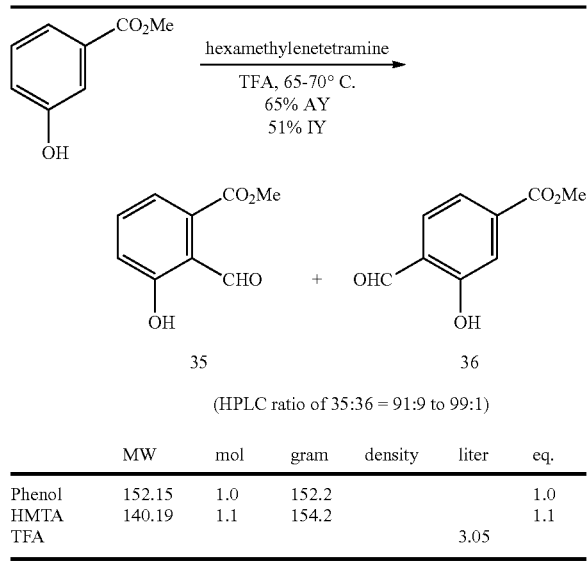

(HPLC ratio of 35:36 = 91:9 to 99:1)

| | MW | mol | gram | density | liter | eq. |
|---|---|---|---|---|---|---|
| Phenol | 152.15 | 1.0 | 152.2 | | | 1.0 |
| HMTA | 140.19 | 1.1 | 154.2 | | | 1.1 |
| TFA | | | | | 3.05 | |

A 5 L jacketed vessel was charged with methyl-3-hydroxybenzoate (34) and trifluoroacetic acid (TFA). Cooling was applied to the jacket, and hexamethylenetetramine (HMTA) was charged slowly over 10-15 minutes, maintaining an internal temperature of less than 30° C. The resulting solution was heated to an internal temperature of 65-70° C. over 1 h. The resulting solution was aged 10-12 h at this temperature, before being cooled to an internal temperature of 20-25° C. over 1 h. The end of reaction mixture was concentrated under reduced pressure (15-80 mm Hg partial pressure) to 1230-1240 mL total volume (about 8 volumes with respect to 34). The internal temperature during concentration was maintained at no more than 40° C.

Separately, a 5 L flask was charged with methanol (MeOH) (150 mL) and water (300 mL), along with compound 35 seeds (360 mg). The concentrated reaction solution and a 33 wt/wt % aqueous $K_2CO_3$ solution (prepared by dissolving 744 g of $K_2CO_3$ in 1.54 L of water) were added simultaneously, optionally using peristaltic pumps at a rate such that each was added over 1 h, maintaining an internal temperature of no more than 30° C. The pH of the solution in the crystallization flask was maintained at pH=2.5 to 4.0 throughout. The resulting slurry (pH=3.3) was aged for at least 2 hours.

The slurry was filtered, and the cake was manually compressed to ~400 mL volume. The cake was displaced with 1:3 MeOH:$H_2O$ (400 mL). The wet cake was dried at 20-25° C. via vacuum suction/$N_2$ sweep for 3 hours. The solids were collected and the initially isolated material was transferred to a 2 L flask with overhead stirring, along with 1:1 IPA:0.58N AcOH (600 mL), After aging for 3.5 h with agitation, $H_2O$ (300 mL) was added over 2 h. The resulting slurry was aged 3-4 hours. The slurry was filtered, and the cake was displaced with 1:3 IPA:$H_2O$ (300 mL). The wet cake was dried at 20-25° C. via vacuum suction/$N_2$ sweep for 3 hours. The isolate was collected. The solid (96.4 g) assayed at 95.3 wt % desired aldehyde and 4.7 wt % undesired aldehyde (para to ester). Final 99.9 wt % purity of combined aldehydes.

Characterization data for 35: $^1$H NMR (300 MHz, CDCl$_3$) δ ppm: 12.20 (s, 1H), 10.62 (s, 1H), 7.55 (t, 1H), 7.46 (d, 1H), 7.18 (d, 1H), 3.95 (s, 3H); $^{13}$C NMR (75 MHz, CDCl$_3$) δ ppm: 197.3, 166.0, 162.9, 135.6, 133.3, 122.3, 122.0, 118.1, 52.6; LRMS [M–H]$^-$ for C$_9$H$_8$O$_4$ calc'd 179.03, found 178.93.

Characterization data for 36: $^1$H NMR (300 MHz, CDCl$_3$) δ ppm: 10.95 (s, 1H), 9.97 (s, 1H), 7.68-7.64 (m, 3H), 3.95 (s, 3H), $^{13}$C NMR (75 MHz, CDCl$_3$) δ ppm: 196.6, 165.8, 161.3, 137.4, 133.7, 123.0, 120.5, 119.2, 52.8.

One crystalline form was identified for Compound 35 and is designated as Form A of Compound 35. The form was characterized by XRPD and DSC, and representative results are provided in FIG. 15 (XRPD) and FIG. 16 (DSC).

Example 10A

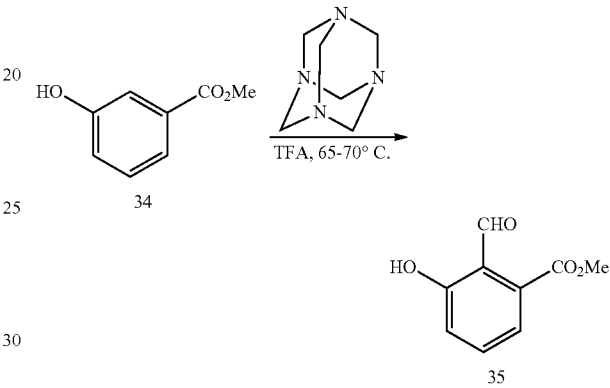

Methyl 3-hydroxybenzoate (250 g, 1.0 equiv, 1.0×wt) and TFA (5000 L, 20×vol) were charged to reactor 1. Any variety of hydroxybenzoate can be used where methyl can be replaced by H, ethyl, propyl, butyl etc. Solvent volumes may vary between 5× to 100×vol. AcOH may be used as a co-solvent. HMTA (253 g, 1.1 equiv, 1.01×wt) was charged portionwise to reactor 1, maintaining T$_i$<50° C. 1.0 to 1.5 equiv of HMTA can be used. Temperatures can vary from 50 to 72° C. Varying amounts of water are tolerated, between 0 to 5 wt % water. The batch was heated to 65±5° C. and temperature was maintained for 10-12 hours. Temperatures can vary from 55 to 72° C. Reaction times can vary from 10 to 72 h. The crude reaction mixture was cooled to T$_i$=20-25° C. Temperatures can vary from 0 to 50° C. The mixture was concentrated under reduced pressure to ~7× volumes total. Concentration under atmospheric pressure can be used. Reaction can be concentrated between 5× and 10×vol.

A solution of $K_2CO_3$ (1200 g, 5.3 eq, 4.8×wt) in $H_2O$ (10×vol) was prepared in reactor 2. $K_2CO_3$ can be replaced by inorganic bases that include potassium acetate, sodium carbonate, lithium carbonate, hydroxides, and bicarbonates. Organic bases can be utilized that include tertiary amines, DBU, guanidine etc. Solvent volumes can vary.

Reactor 3 was charged with IPA (1×vol), $H_2O$ (2×vol), and seed (0.001×wt %). IPA can be replaced with methanol, ethanol, n-propanol, MeCN, DMSO, DMAc, DMF, NMP, THF. Seed load can vary between 0 and 50 wt %. IPA solvent volumes can vary between 0 to 10×vol. Water or antisolvent charge can vary between 0 and 10×vol.

Solutions in reactor 1 and reactor 2 were simultaneous added into reactor 3, maintaining pH=2-4. An inverse addition into aqueous solutions of bases can be performed. pH can vary between 2 and 6. Traditional biphasic workups with aqueous base and non-water miscible organic solvents are possible. The slurry in reactor 3 was filtered. The cake was subject to displacement wash with 1:3 IPA: H₂O (4×vol). Displacement volumes can vary. Alternative ratios of IPA:H₂O can be used. The solids were dried. Solids can be dried between 0 and 40° C.

The isolated solids were re-slurried in reactor 4, where reactor 4 was pre-charged with 1:1 i-PrOH:0.55N AcOH (4×vol). Other water miscible solvents can be used that include methanol, ethanol, propanol etc., acetonitrile, DMF, DMAc, NMP, DMSO, and THF. AcOH can be replaced by sulfonic acids, carboxcylic acids, mineral acids, amino acids. Other concentration of AcOH between 0 to 100% can be used. Varying ratios of IPA/AcOH can be used. H₂O (2×vol) was slowly added, then allowed to age. H₂O volumes can vary between 0 and 100×vol. The slurry in reactor 4 was filtered, and the cake was subject to displacement wash with 2:5 IPA:H₂O (3×vol). Displacement volumes can vary. Alternative ratios of IPA:H₂O can be used. The solid was dried with vacuum suction/N₂ sweep to provide Compound 35. The solid can be dried between 0 and 40° C.

Characterization data for 35: $^1$H NMR (300 MHz, CDCl₃) δ ppm: 12.20 (s, 1H), 10.62 (s, 1H), 7.55 (t, 1H), 7.46 (d, 1H), 7.18 (d, 1H), 3.95 (s, 3H); $^{13}$C NMR (75 MHz, CDCl₃) δ ppm: 197.3, 166.0, 162.9, 135.6, 133.3, 122.3, 122.0, 118.1, 52.6; LRMS [M−H]⁻ for C₉H₈O₄ calc'd 179.03, found 178.93. XRPD and DSC are consistent with FIG. 15 (XRPD) and FIG. 16 (DSC).

Example 11

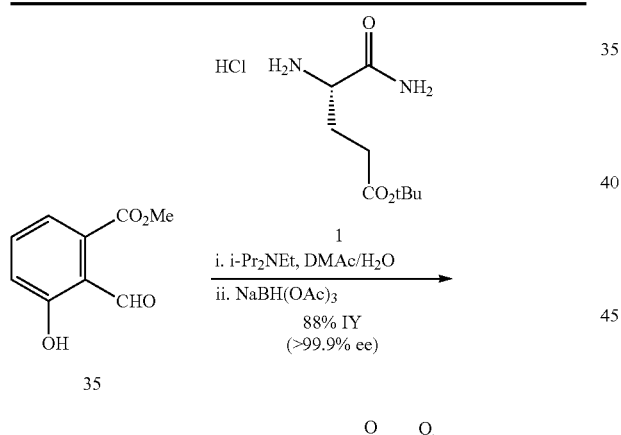

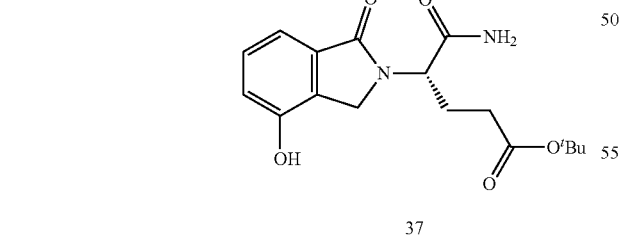

|   | MW | mmol | gram | density | mL | eq. |
|---|---|---|---|---|---|---|
| 1 | 238.71 | 345 | 82.3 |  |  | 1.15 |
| iPr₂Net | 129.24 | 360 | 46.5 | 0.742 | 62.7 | 1.20 |
| DMAc |  |  |  |  | 150 |  |
| 35 (94.2 wt %) | 180.16 | 300 | 54.0 (57.4) |  |  | 1.0 |
| AcOH | 60.05 | 450 | 27.0 | 1.05 | 25.7 | 1.5 |
| NaBH(OAc)₃ | 211.94 | 420 | 89.0 |  |  | 1.4 |

A vessel was charged with compound 1 HCl salt and dimethylacetamide (DMAc) and the resulting slurry was agitated slowly. Diisopropylethylamine (iPr₂NEt) was added, and the resulting homogeneous solution was aged at 20-25° C. for 1 h.

The homogeneous solution was then cooled to 0-5° C. and AcOH was added. After re-cooling, the aldehyde 35 was added as a solid, maintaining an internal temperature of no more than 5° C. The resulting homogeneous solution was aged 1.5-2 h after the aldehyde addition. Sodium triacetoxyborohydride (STAB) was added as a solid in four equal portions (separated by about 30 minutes each), maintaining an internal temperature of no more than 5° C. The resulting slurry was aged at 0-5° C. for 8-10 h.

The jacket was warmed to 20-25° C. over 30-60 min. and the slurry was aged at an internal temperature of 20-25° C. for 1 h. H₂O (300 mL) was added over 30-60 minutes (note: gas evolution was observed due to quench of excess STAB) and the resulting homogeneous solution was seeded with Compound 37 (0.1 wt %), and the resulting seed bed was aged for 2 h.

Additional H₂O (900 mL) was added over 1.5-2 h and the resulting slurry was aged for at least 1 h. The slurry was filtered and the cake was displaced with 1:8 DMAc:H₂O (250 mL), followed by H₂O (250 mL). The wet cake was dried at 20-25° C. via vacuum suction/N₂ sweep for 12 hours. The isolate was collected (89.6 g) and assayed at 98.8 wt % (88.5% IY, 99% e.e.).

$^1$H NMR (300 MHz, DMSO-d₆) δ ppm: 10.03 (s, 1H), 7.56 (s, 1H), 7.31 (dd, J₁=J₂=7.7 Hz, 1H), 7.18 (s, 1H), 7.15 (d, J=7.5 Hz, 1H), 6.98 (d, J=7.7 Hz, 1H), 4.71 (dd, J₁=10.4 Hz, J₂=4.4 Hz, 1H), 4.49 (d, J=17.6 Hz, 1H), 4.31 (d, J=17.6 Hz, 1H), 2.21-2.09 (m, 3H), 1.32 (s, 9H); $^{13}$C NMR (75 MHz, DMSO-d₆) δ ppm: 172.0, 171.4, 168.2, 133.7, 129.3, 128.3, 79.8, 53.5, 44.9, 31.8, 27.7, 25.0; LRMS [M+H]⁺ for C₁₇H₂₂N₂O₅ calc'd 335.16, found 335.15.

One crystalline form was identified for Compound 37 and is designated as Form 1. The form was characterized by XRPD and DSC, and representative results are provided in FIG. 17 (XRPD) and FIG. 18 (DSC).

The procedure above led to a high ratio of enantiomers (>99.75:0.25) of the product 37. Deviation, particularly with respect to temperature control, can lead to ratios of <98:2. Example of a chiral HPLC chromatogram from a typical reaction using the procedure above is shown in FIG. 19A (Compound 37 eluted at 9.19 min., area 3109516, % area 99.94, height 161194; the R-enantiomer eluted at 6.27 min., area 1791, % area 0.06, height 106). Example of a chiral HPLC chromatogram from an atypical reaction where the reaction temperature was maintained at T₁=15-20° C. for 6 h after the addition of 35 and prior to the addition of STAB is shown in FIG. 19B (Compound 37 eluted at 9.47 min., area 4366151, height 259118; the R-enantiomer eluted at 6.32 min., area 80091, height 4543).

Example 11A

Reaction 1: Free Base Compound 1

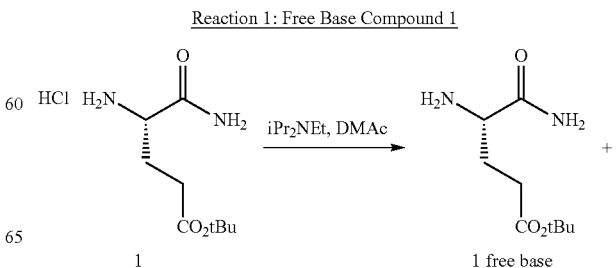

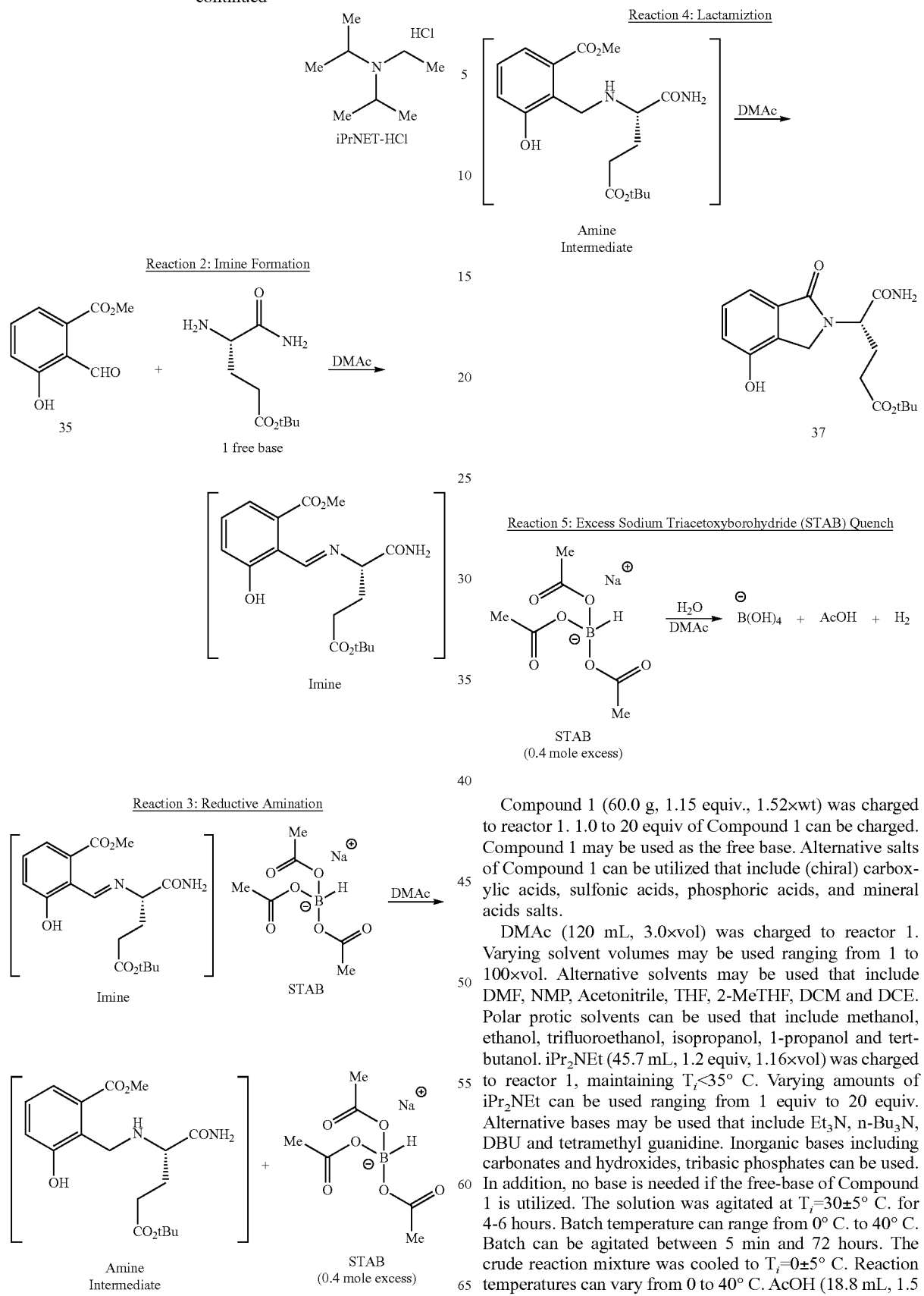

Compound 1 (60.0 g, 1.15 equiv., 1.52×wt) was charged to reactor 1. 1.0 to 20 equiv of Compound 1 can be charged. Compound 1 may be used as the free base. Alternative salts of Compound 1 can be utilized that include (chiral) carboxylic acids, sulfonic acids, phosphoric acids, and mineral acids salts.

DMAc (120 mL, 3.0×vol) was charged to reactor 1. Varying solvent volumes may be used ranging from 1 to 100×vol. Alternative solvents may be used that include DMF, NMP, Acetonitrile, THF, 2-MeTHF, DCM and DCE. Polar protic solvents can be used that include methanol, ethanol, trifluoroethanol, isopropanol, 1-propanol and tert-butanol. iPr$_2$NEt (45.7 mL, 1.2 equiv, 1.16×vol) was charged to reactor 1, maintaining T$_i$<35° C. Varying amounts of iPr$_2$NEt can be used ranging from 1 equiv to 20 equiv. Alternative bases may be used that include Et$_3$N, n-Bu$_3$N, DBU and tetramethyl guanidine. Inorganic bases including carbonates and hydroxides, tribasic phosphates can be used. In addition, no base is needed if the free-base of Compound 1 is utilized. The solution was agitated at T$_i$=30±5° C. for 4-6 hours. Batch temperature can range from 0° C. to 40° C. Batch can be agitated between 5 min and 72 hours. The crude reaction mixture was cooled to T$_i$=0±5° C. Reaction temperatures can vary from 0 to 40° C. AcOH (18.8 mL, 1.5 equiv, 0.48×vol) was charged to reactor 1. Varying amounts of AcOH can be utilized that range from 0 to 20 equiv.

Alternative acids may be utilized that include alternative carboxylic acids (alkyl, aryl, TFA), sulfonic acids, mono basic phosphoric acid. Alternative reagents such as $T_i(^iPrO)_4$, $T_i(OEt)_4$, $Al(^iPrO)_3$, boronic acids, orthoformates, and activated molecular sieves can also be used. Solid Compound 35 (39.4 g, 1.0 equiv, 1.0×wt) was charged to reactor 1, maintaining $T_i \leq 10°$ C. Batch temperature can range from $T_i \leq 10°$ C. to 40° C. The solution was aged at $T_i = 0 \pm 5°$ C. for 2-3 hours. Varying age times may be used from 1 h to 24 h. Temperatures may vary from 0 to 40° C. STAB (69.5 g, 1.5 equiv, 1.65×wt) was charged in five equal portions, separated by NLT 30 min., maintaining $T_i < 5°$ C. Alternative reducing agents such as $NaBH_4$, $NaBH_3CN$, silanes, and $H_2$ in combination with transition metal catalysts (Pd, Pt, Rh, Ir-etc). STAB can be added in 1 to 10 portions separated by 0 to 12 h. Varying temperatures may be used from 0 to 40° C. The solution was aged at $T_i = 0 \pm 5°$ C. for 8-10 hours. The age times may vary between 5 and 72 hours. Alternative temperature between 0 and 40° C. can be used. The solution was heated to $T_i = 20 \pm 5°$ C. over 1-2 h and held at this temperature for 2-3 hours. Temperature ramp can vary between 0 and 5 h. Temperature can vary from 20 to 40° C. Hold times can range from 0 to 72 h. $H_2O$ (6.0×vol) was charged to reactor 1 over 0.5-1 h. Water charge can vary from 3 to 6×vol. Time of charge can range between 0 and 12 h. Seed was charged and allowed to age for 1-2 h. Seed charge can vary between 0 and 50 wt %. Age time can vary between 0 and 12 h. $H_2O$ (18.0×vol) was charged to reactor 1 over 4-6 h. Alternative solvent volumes can be used. Charge time can vary from 30 min to 12 h. The slurry was aged for NLT 2 h. The batch can be aged between 0 and 24 h. The slurry was filtered, and the cake was subject to displacement wash with 5×vol of 1:8 DMAc:$H_2O$ (vol:vol). Different solvent volumes and ratios can be used. The cake was subject to displacement wash with $H_2O$ (5×vol). Alternative volumes can be used. The product was dried with vac/$N_2$ sweep to provide Compound 37. A temperature of 10 to 50° C. can be used. A nitrogen sweep can be omitted.

Analytical Data for compound 37: HPLC purity: 100%. HPLC chiral purity: 99.98%. $^1$H NMR (DMSO-$d_6$, 300 MHz): δ=10.01 (s, 1H), 7.55 (s, 1H), 7.30 (t, J=8 Hz, 1H), 7.16-7.14 (m, 2H), 6.99 (d, J=8 Hz, 1H), 4.73-4.61 (m, 1H), 4.40 (AB quartet, J=17 Hz, 2H), 2.18-2.10 (m, 3H), 2.03-1.90 (m, 1H), 1.42 (s, 9H). $^{13}$C NMR (DMSO-$d_6$, 75 MHz): δ ppm: 172.0, 171.4, 168.2, 133.7, 129.3, 128.3, 79.8, 53.5, 44.9, 31.8, 27.7, 25.0. LRMS [M+H]$^+$ for $C_{17}H_{22}N_2O_5$ calc'd 335.16, found 335.15. XRPD and DSC are consistent with FIG. 17 (XRPD) and FIG. 18 (DSC).

In an alternative run, compound 1, dimethylacetamide (DMAc), and N,N-diisopropylethylamine (iPr$_2$NEt) were charged to a reactor and agitated. The batch was cooled and acetic acid (AcOH) was charged, followed by compound 35. Sodium triacetoxyborohydride (NaB(OAc)$_3$H) was charged.

After reaction completion the batch was warmed, water was charged followed by compound 37 seeds, and additional water. The resulting solids were filtered, washed with water/DMAc and then with water. The batch was dried under reduced pressure to yield compound 37.

The synthetic route can be used to make the racemic Compound 37 by starting with racemic starting material, or by racemizing the stereogenic center. One crystalline form was identified for racemic Compound 37 and is designated as Form 1 of racemic compound 1. The form was characterized by XRPD and DSC, and representative results are provided in FIG. 20 (XRPD) and it R. 21 (DSC).

Example 12. Single Crystal Experiment for Compound 35

A single crystal of Compound 35 suitable for single crystal XRD analysis was grown from sample Compound 35. The solid Compound 35 was dissolved in the mixture of methyl tert-butyl ether/heptane (2.5 mL, 5/1) to give a saturated solution which was stored in hood at room temperature. After 14 days, plane-like crystals were found.

A crystalline sample of Compound 35 was analyzed by single-crystal x-ray diffraction (XRD). The XRD analysis confirmed the structure. The empirical formula is $C_9H_8O_4$. (MW=180.2).

The structure was solved and refined using the Bruker SHELXTL Software Package, using the space group P n a 21, with Z=4 for the formula unit, $C_9H_8O_4$. The final anisotropic full-matrix least-squares refinement on $F^2$ with 124 variables converged at R1=3.24%, for the observed data and wR2=8.41% for all data. The goodness-of-fit was 1.038. The largest peak in the final difference electron density synthesis was 0.177 e$^-$/Å$^3$ and the largest hole was −0.203 e$^-$/Å$^3$ with an RMS deviation of 0.047 e$^-$/Å$^3$. On the basis of the final model, the calculated density was 1.444 g/cm$^3$ and F(000), 376 e$^-$.

The crystal data are provided in Table 1. The details on data collection and structure refinement are provided in Table 2. The molecular structure of Form A of Compound 35 is provided in FIG. 22

TABLE 1

| Crystal data for Form A of Compound 35 | | |
|---|---|---|
| Chemical formula | $C_9H_8O_4$ | |
| Formula weight | 180.15 g/mol | |
| Temperature | 200(2) K | |
| Wavelength | 1.54178 Å | |
| Crystal size | 0.285 × 0.427 × 0.460 mm | |
| Crystal habit | clear colourless block | |
| Crystal system | orthorhombic | |
| Space group | P n a 21 | |
| Unit cell dimensions | a = 19.4582(9) Å | α = 90° |
| | b = 3.7807(2) Å | β = 90° |
| | c = 11.2611(5) Å | γ = 90° |
| Volume | 828.43(7) Å$^3$ | |
| Z | 4 | |
| Density (calculated) | 1.444 g/cm$^3$ | |
| Absorption coefficient | 0.980 mm$^{-1}$ | |
| F(000) | 376 | |

TABLE 2

| Data collection and structure refinement for Form A of Compound 35 | |
|---|---|
| Theta range for data collection | 4.54 to 75.16° |
| Index ranges | −24 <= h <= 17, −4 <= k <= 4, −14 <= l <= 13 |
| Reflections collected | 5258 |
| Independent reflections | 1606 [R(int) = 0.0348] |
| Coverage of independent reflections | 99.0% |
| Absorption correction | Multi-Scan |
| Max. and min. transmission | 0.7680 and 0.6610 |
| Structure solution technique | direct methods |
| Structure solution program | XT, VERSION 2014/5 |
| Refinement method | Full-matrix least-squares on $F^2$ |
| Refinement program | SHELXL-2017/1 (Sheldrick, 2017) |
| Function minimized | $\Sigma\ w(F_o^2 - F_c^2)^2$ |
| Data/restraints/parameters | 1606/2/124 |
| Goodness-of-fit on $F^2$ | 1.038 |
| Final R indices | R1 = 0.0324, wR2 = 0.0838 |

TABLE 2-continued

Data collection and structure refinement for Form A of Compound 35

| | |
|---|---|
| 1588 data; I > 2σ(I) all data | R1 = 0.0326, wR2 = 0.0841 |
| Weighting scheme | w = 1/[σ²($F_o^2$) + (0.0652P)² + 0.0418P] where P = ($F_o^2$ + 2$F_c^2$)/3 |
| Absolute structure parameter | 0.03(6) |
| Extinction coefficient | 0.0210(40) |
| Largest diff. peak and hole | 0.177 and −0.203 eÅ⁻³ |
| R.M.S. deviation from mean | 0.047 eÅ⁻³ |

Example 13. Single Crystal Experiment for Compound 37

A single crystal of Compound 37 suitable for single crystal XRD analysis was grown from sample Compound 37. The solid Compound 37 was dissolved in the mixture of ethyl acetate/methanol (1.2 mL, 4/1) to give a saturated solution which was stored in Dewar bottle at room temperature. After 11 days, plane-like crystals were found.

A crystalline sample of Compound 37 was analyzed by single-crystal x-ray diffraction (XRD). The XRD analysis confirmed the structure. The empirical formula is $C_{17}H_{22}N_2O_5$. (MW=334.36).

The structure was solved and refined using the Bruker SHELXTL Software Package, using the space group P 21 21 21, with Z=8 for the formula unit, $C_{17}H_{22}N_2O_5$. The final anisotropic full-matrix least-squares refinement on F² with 463 variables converged at R1=3.20%, for the observed data and wR2=8.66% for all data. The goodness-of-fit was 1.020. The largest peak in the final difference electron density synthesis was 0.205 e⁻/Å³ and the largest hole was −0.226 e⁻/Å³ with an RMS deviation of 0.038 e⁻/Å³. On the basis of the final model, the calculated density was 1.240 g/cm³ and F(000), 1424 e⁻.

The crystal data are provided in Table 3. The details on data collection and structure refinement are provided in Table 4. The molecular structure of Form 1 of Compound 37 is provided in FIG. 23.

TABLE 3

Crystal data for Form 1 of Compound 37

| | | |
|---|---|---|
| Chemical formula | $C_{17}H_{22}N_2O_5$ | |
| Formula weight | 334.36 g/mol | |
| Temperature | 200(2) K | |
| Wavelength | 1.54178 Å | |
| Crystal size | 0.356 × 0.404 × 0.592 mm | |
| Crystal system | orthorhombic | |
| Space group | P 21 21 21 | |
| Unit cell dimensions | a = 10.0655(4) Å | α = 90° |
| | b = 10.8867(4) Å | β = 90° |
| | c = 32.6975(13) Å | γ = 90° |
| Volume | 3583.0(2) Å³ | |
| Z | 8 | |
| Density (calculated) | 1.240 g/cm³ | |
| Absorption coefficient | 0.761 mm⁻¹ | |
| F(000) | 1424 | |

TABLE 4

Data collection and structure refinement for Form 1 of Compound 37

| | |
|---|---|
| Theta range for data collection | 4.28 to 75.44° |
| Index ranges | −12 <= h <= 12, −13 <= k <= 12, −40 <= l <= 40 |

TABLE 4-continued

Data collection and structure refinement for Form 1 of Compound 37

| | |
|---|---|
| Reflections collected | 46409 |
| Independent reflections | 7386 [R(int) = 0.0227] |
| Coverage of independent reflections | 99.4% |
| Absorption correction | Multi-Scan |
| Max. and min. transmission | 0.7730 and 0.6610 |
| Structure solution technique | direct methods |
| Structure solution program | SHELXT 2014/5 (Sheldrick, 2014) |
| Refinement method | Full-matrix least-squares on F² |
| Refinement program | SHELXL-2017/1 (Sheldrick, 2017) |
| Function minimized | Σ w($F_o^2$ − $F_c^2$)² |
| Data/restraints/parameters | 7386/0/463 |
| Goodness-of-fit on F² | 1.020 |
| Δ/σ$_{max}$ | 0.001 |
| Final R indices | R1 = 0.0320, wR2 = 0.0863 |
| 7298 data; I > 2σ(I) all data | R1 = 0.0323, wR2 = 0.0866 |
| Weighting scheme | w = 1/[σ²($F_o^2$) + (0.0567P)² + 0.5087P] where P = ($F_o^2$ + 2$F_c^2$)/3 |
| Absolute structure parameter | 0.02(2) |
| Largest diff. peak and hole | 0.205 and −0.226 eÅ⁻³ |
| R.M.S. deviation from mean | 0.038 eÅ⁻³ |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

All of the patents, patent applications and publications referred to herein are incorporated herein in their entireties. Citation or identification of any reference in this application is not an admission that such reference is available as prior art to the claimed subject matter.

What is claimed is:

1. A process for preparing a compound of Formula (I-rac):

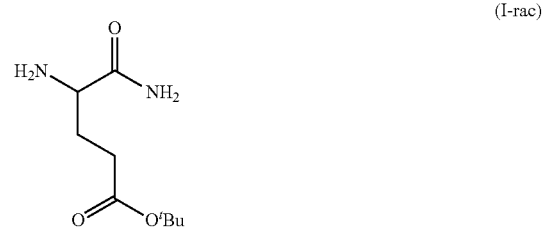 [SMILES: CC(C)(C)OC(=O)CCC(N)C(N)=O]

(I-rac)

or a salt, solvate, hydrate, enantiomer, or isotopologue thereof, comprising (a) contacting a compound of Formula (XI):

(XI)

or a solvate, hydrate, or isotopologue thereof, wherein R⁵ is —CONH₂, —CN, or —CO₂R⁶, and R⁶ is a $C_{1-10}$ alkyl, with tert-butyl acrylate in the presence of a base to provide a compound of Formula (XII):

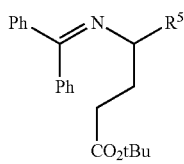

(XII)

or a solvate, hydrate, or isotopologue thereof;
  (b) transforming the compound of Formula (XII), or a solvate, hydrate, or isotopologue thereof, to a compound of Formula (XIII):

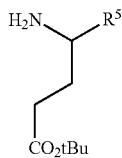

(XIII)

or a solvate, hydrate, or isotopologue thereof, in the presence of an acid;
  (c) when $R^5$ is not —$CONH_2$, transforming the $R^5$ group to —$CONH_2$ to provide a compound of Formula (I-rac), or a solvate, hydrate, or isotopologue thereof, wherein the —$NH_2$ group in the compound of Formula (XIII), or a solvate, hydrate, or isotopologue thereof, is optionally protected and deprotected in step (c);
  (d) optionally separating the compound of Formula (I-rac), or a solvate, hydrate, or isotopologue thereof, to provide a compound of Formula (I):

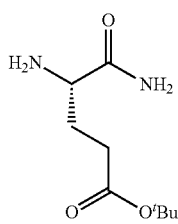

(I)

or a solvate, hydrate, or isotopologue thereof, via a chiral separation condition; and
  (e) optionally converting the compound of Formula (I), or a solvate, hydrate, or isotopologue thereof, to a salt of the compound.

2. A process for preparing a compound of Formula (I-rac):

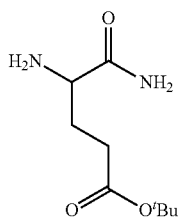

(I-rac)

or a salt, solvate, hydrate, enantiomer, or isotopologue thereof, comprising (b) transforming a compound of Formula (XII):

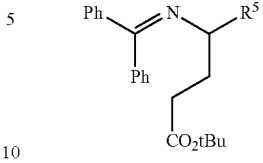

(XII)

or a solvate, hydrate, or isotopologue thereof, wherein $R^5$ is —$CONH_2$, —CN, or —$CO_2R^6$, and $R^6$ is a $C_{1-10}$ alkyl, to a compound of Formula (XIII):

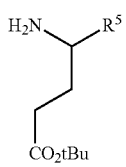

(XIII)

or a solvate, hydrate, or isotopologue thereof, in the presence of an acid;
  (c) when $R^5$ is not —$CONH_2$, transforming the $R^5$ group to —$CONH_2$ to provide a compound of Formula (I-rac), or a solvate, hydrate, or isotopologue thereof, wherein the —$NH_2$ group in the compound of Formula (XIII), or a solvate, hydrate, or isotopologue thereof, is optionally protected and deprotected in step (c);
  (d) optionally separating the compound of Formula (I-rac), or a solvate, hydrate, or isotopologue thereof, to provide a compound of Formula (I):

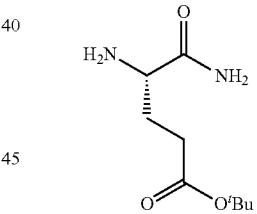

(I)

or a solvate, hydrate, or isotopologue thereof, via a chiral separation condition; and
  (e) optionally converting the compound of Formula (I), or a solvate, hydrate, or isotopologue thereof, to a salt of the compound.

3. The process of claim 1, wherein $R^5$ is —$CONH_2$.
4. The process of claim 1, wherein $R^5$ is —CN.
5. The process of claim 1, wherein $R^5$ is —$CO_2Me$.
6. The process of claim 1, wherein when $R^5$ is not —$CONH_2$, step (c) comprises (c1) protecting the —$NH_2$ group with a protecting group, (c2) transforming the $R^5$ group to —$CONH_2$; and (c3) deprotecting the protecting group of the —$NH_2$ group.
7. The process of claim 6, wherein the $R^5$ group is transformed to —$CONH_2$ directly.
8. The process of claim 6, wherein the $R^5$ group is transformed to a —COOH group, and then the —COOH group is transformed to —$CONH_2$.

9. The process of claim 6, wherein the protecting group for the —NH$_2$ group in step (c1) is benzyl (Bn), 4-methoxybenzyl (PMB), 3,4-dimethoxybenzyl (DMPM), benzyloxycarbonyl (Cbz), or p-methoxybenzyloxycarbonyl (Moz).

10. The process of claim 9, wherein the protecting group for the —NH$_2$ group in step (c1) is benzyl or Cbz.

11. The process of claim 6, wherein the deprotection in step (c3) occurs under a hydrogenation condition.

12. The process of claim 1, wherein the base in step (a) is triethylamine, diisopropylethylamine, pyridine, 4-dimethylaminopyridine, or 1,8-diazabicyclo[5.4.0]undec-7-ene (DBU).

13. The process of claim 12, wherein the base in step (a) is DBU.

14. The process of claim 1, wherein the base in step (a) is Cs$_2$CO$_3$.

15. The process of claim 1, wherein the acid in step (b) is formic acid, acetic acid, trifluoroacetic acid, benzoic acid, citric acid, sulfonic acid, benzenesulfonic acid, p-toluenesulfonic acid, camphorsulfonic acid, methanesulfonic acid, trifluoromethanesulfonic acid, hydrochloric acid, sulfuric acid, nitric acid, or phosphoric acid.

16. The process of claim 15, wherein the acid in step (b) is HCl, citric acid, or p-toluenesulfonic acid.

17. The process of claim 1, wherein step (d) comprises contacting the compound of Formula (I-rac), or a solvate, hydrate, or isotopologue thereof, with a chiral acid to provide a diastereomeric mixture of salts, and separating the resulted diastereomeric mixture of salts by selective crystallization.

18. The process of claim 17, wherein the chiral acid is tartaric acid, 2,3-dibenzoyl tartaric acid, mandelic acid, camphorsulfonic acid, N-Ac-N-leucine, or N-Ac-L-phenylalanine.

19. The process of claim 17, wherein the selective crystallization occurs in a solvent selected from MeOH, isopropanol, and n-propanol, or a mixture thereof.

20. The process of claim 1, wherein the compound is converted to a hydrochloride salt of the compound in step (e).

* * * * *